(12) United States Patent
Aguirre Ena et al.

(10) Patent No.: US 10,407,423 B2
(45) Date of Patent: Sep. 10, 2019

(54) COMPOUNDS AS INHIBITORS OF DNA METHYLTRANSFERASES

(71) Applicant: FUNDACIÓN PARA LA INVESTIGACIÓN MÉDICA APLICADA, Pamplona (ES)

(72) Inventors: Xabier Aguirre Ena, Pamplona (ES); Julen Oyarzabal Santamarina, Pamplona (ES); Felipe Prósper Cardoso, Pamplona (ES); Maria Obdulia Rabal Gracia, Pamplona (ES); Edurne San José Enériz, Pamplona (ES); Juan Antonio Sánchez Arias, Pamplona (ES)

(73) Assignee: FUNDACIÓN PARA LA INVESTIGACIÓN MÉDICA APLICADA, Pamplona (ES)

( * ) Notice: Subject to any disclaimer, the term of this patent is extended or adjusted under 35 U.S.C. 154(b) by 0 days.

(21) Appl. No.: 15/775,746

(22) PCT Filed: Nov. 15, 2016

(86) PCT No.: PCT/EP2016/077712
§ 371 (c)(1),
(2) Date: May 11, 2018

(87) PCT Pub. No.: WO2017/085053
PCT Pub. Date: May 26, 2017

(65) Prior Publication Data
US 2018/0362525 A1 Dec. 20, 2018

(30) Foreign Application Priority Data
Nov. 16, 2015 (EP) .................................... 15382565

(51) Int. Cl.
*C07D 471/04* (2006.01)
*A61K 35/02* (2015.01)
*A61P 35/02* (2006.01)

(52) U.S. Cl.
CPC ............ *C07D 471/04* (2013.01); *A61P 35/02* (2018.01)

(58) Field of Classification Search
CPC ............................... C07D 471/04; A61P 35/02
USPC ...................................................... 514/234.2
See application file for complete search history.

(56) References Cited

U.S. PATENT DOCUMENTS 5,360,799 A 11/1994 Bachy et al.
6,126,959 A * 10/2000 Levine ................. A61K 9/0034
424/434
2008/0306049 A1 12/2008 Kaplan et al.

FOREIGN PATENT DOCUMENTS

| CN | 1830978 A | 9/2006 |
| EP | 0587473 A1 | 3/1994 |
| EP | 0922044 B1 | 10/2001 |
| EP | 1238979 A1 | 9/2002 |
| WO | WO 2015/012704 A1 | 1/2015 |

OTHER PUBLICATIONS

International Search Report and Written Opinion dated Feb. 28, 2017 for PCT Application No. PCT/EP2016/077712, 11 pages.
Chambers, Richard D., et al., "Reactions involving fluoride ion. Part 42. Heterocyclic compounds from perfluoro-3,4-dimethylhexa-2,4-diene", Journal Chem. Soc Perkin Trans 1997, vol. 10, pp. 1457-1463.
Esteve, Pierre-Olivier, et al., "Direct interation between DNMT1 and G9a coordinates DNA and histone methylation during replication", Genes Dev Nov. 3, 2006, vol. 20, pp. 3089-3103.
Fahy, Jacques, et al., "DNA methyltransferase inhibitors in cancer: a chemical and therapeutic patent overview and selected clinical studies", Expert Opinion on Therapeutic Patents, vol. 22, No. 12, Dec. 1, 2012, pp. 1427-1442.
Green, et al., "Protective Groups in Organic Chemistry; Chapter 2: Protection for the Hydroxyl Group, Including 1,2- and 1,3-Diols", Wiley 3$^{rd}$ ed., 1999, pp. 17-200.
Green, et al., "Protective Groups in Organic Chemistry; Chapter 5: Protection for the Carboxyl Group", Wiley 3$^{rd}$ ed., 1999, pp. 369-451.
Lee, Senghee, et al., "DNA methyltransferase inhibition accelerates the immunomodulation and migration of human mesenchymal stem cells", Scientific Reports Jan. 26, 2015, vol. 5, No. 8020, pp. 1-10.
Neary, Robin, et al., "Epigenetics and the overhealing wound: the role of DNA methylation in fibrosis", Fibrogenesis & Tissue Repair 2015, vol. 8, No. 18, pp. 1-13.
Pierre, Fabrice, et al., "Discovery and SAR of 5-(3-Chlorophenylamino)benzo[c][2,6]naphthyridine-8-carboxylic Acid (CX-4945), the First Clinical State Inhibitor of Protein Kinase CK2 for the Treatment of Cancer", Journal of Med Chemistry 2011, Dec. 21, 2010, vol. 54, No. 2, pp. 635-654.

(Continued)

*Primary Examiner* — Niloofar Rahmani
(74) *Attorney, Agent, or Firm* — Squire Patton Boggs (US) LLP

(57) ABSTRACT

It relates to the compounds of formula (I), or their pharmaceutically or veterinary acceptable salts, or their stereoisomers or mixtures thereof, wherein A, $R_1$, $R_2$, and $R_3$ are as defined herein, which are inhibitors of one or more DNMTs selected from the group consisting of DNMT1, DNMT3A and DNMT3B. It also relates to pharmaceutical or veterinary compositions containing them, and to their use in medicine, in particular in the treatment and/or prevention of cancer, fibrosis and/or immunomodulation.

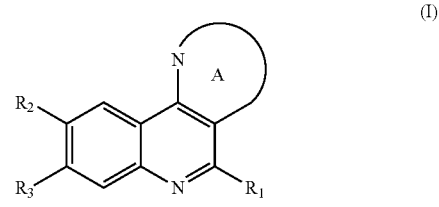

(I)

18 Claims, No Drawings

(56) References Cited

OTHER PUBLICATIONS

Shankar, Shilpa Rani, et al., G9a, a multipotent regulator of gene expression, Epigenetics Jan. 2013, vol. 8, No. 1, pp. 16-22.

Sharma, Shuikhar, et al., "Lysine methyltransferase G9a is not required for DNMT3A/3B anchoring to methylated nucleosomes and maintenance of DNA methylation in somatic cells", Epigenetics & Chromatin 2012, vol. 5, No. 3, pp. 1-12.

Tachibana, Makoto, et al., "G9a/GLP complexes independently medicate H3K9 and DNA methylation to silence transcription", The EMBO Journal Sep. 25, 2008, vol. 27, No. 20, pp. 2681-2690.

Vilas-Zornoza, Amaia, et al., "Frequent and simultaneous epigenetic inactivation of TP53 pathway genes in acute lymphoblastic leukemia", PLoS ONE Feb. 2011, vol. 6, No. 2, pp. e17012, 14 pages.

Wozniak, R.J., et al., "5-Aza-2'-deoxycytidine-mediated reductions in G9A histone methyltransferase and histone H3 K9 di-methylation levels are linked to tumor suppressor gene reactivation", Oncogene 2007, vol. 26, pp. 77-90.

* cited by examiner

COMPOUNDS AS INHIBITORS OF DNA METHYLTRANSFERASES

This application claims the benefit of European Patent Application EP15382565.8 filed on Nov. 16, 2015.

The present invention relates to 3,4-heterocyclo-quinoline compounds, which are inhibitors of DNA methyltransferases. It also relates to pharmaceutical or veterinary compositions containing them, and to their use in medicine, in particular as anticancer agents, antifibrotic and immunomodulator agents.

BACKGROUND ART

In recent years, it has been shown that cancer is a genetic and epigenetic disease, where epigenetic and genetic alterations interact reciprocally to drive cancer development. However, unlike genetic mutations, epigenetic changes are reversible, and as such, drugs that restore the epigenetic balance represent exciting potential therapeutic targets for cancer. Epigenetics refers to the heritable changes in gene expression patterns that occur independently of alterations in primary DNA sequence. The main epigenetic mechanisms are DNA methylation and covalent histone modifications, which play important roles in the regulation of transcription.

DNA methylation is an epigenetic modification that modulates gene expression without altering the DNA base sequence and plays a crucial role in cancer by silencing tumor suppressor genes. DNA methyltransferases (DNMTs) are the enzymes that catalyze DNA methylation. DNMT1 encodes the maintenance methyltransferase and DNMT3A and DNMT3B encode de novo methyltransferases.

DNMT1 and DNMT3A/3B are overexpressed in several types of cancer such as breast, gastric, pancreas, prostate, hepatocellular, ovarian, renal, retinoblastoma, glioma or diffuse large B-cell lymphoma. The DNA hypomethylating agents like Zebularine, decitabine and azacytidine inhibits cell proliferation and induce apoptosis in acute lymphoblastic leukemia, acute myeloid leukemia, hepatic carcinoma, lung, breast, gastric or cervical cancer among others (Vilas-Zornoza A. et al., PLoS ONE 2011, 6(2): p. e17012). Decitabine has been currently approved for myelodysplastic syndrome by the US Food and Drug Administration. On the other hand, DNA methylation plays a key role in the pathogenesis of fibrosis (Neary, R. et al, Fibrogenesis & Tissue Repair 2015, 8:18). Further, DNA methyltransferase inhibition also accelerates the immunomodulation and migration of human mesenchymal stem cells (Lee S. et al., Scientific Reports 2015, 5:8020).

However, many efforts are made to develop new non-nucleoside inhibitors to overcome the limits of these aza-nucleosides, such as chemical instability and incorporation into DNA for activity.

G9a, also known as EHMT2, is a histone methyltransferase that mono- and dimethylates Lysine 9 of histone H3 (H3K9me1 and H3K9me2, respectively). G9a expression is high in many cancers compared with normal tissue. Cancer transcriptome analysis has revealed high expression in many tumors including hepatocellular, colon, prostate, lung bladder and invasive transitional cell carcinomas and in B cell chronic lymphocytic leukemia (Shankar S R. et al., Epigenetics 2013, 8(1): p. 16-22). Knockdown of G9a in both bladder and lung cancer cell lines caused growth suppression and apoptosis. Studies on prostate cancer further corroborate its role in carcinogenesis, where downregulation of G9a causes centrosome disruption, chromosomal instability, inhibition of cell growth and increased cellular senescence in cancer cells. In aggressive lung cancer, high levels of G9a correlate with poor prognosis with increased cell migration and invasion in vitro and metastasis in vivo. G9a is also overexpressed in pancreatic adenocarcinoma and inhibition of G9a induces cellular senescence in this type of cancer. In Acute Myeloid Leukemia mouse models, loss of G9a significantly delays disease progression and reduces leukemia stem cells frequency.

Interestingly, DNA methyltransferase-1 (DNMT1) physically interacts with G9a to coordinate DNA and histone methylation during cell division (Esteve P O. et al., Genes Dev 2006, 20:3089-3103) promoting transcriptional silencing of target genes (Tachibana M. et al., EMBO J 2008, 27:2681-2690). In this sense, reduction of both DNA and H3K9 methylation levels leads to reactivation of tumor suppressor genes and inhibits cancer cell proliferation (Wozniak R J. et al., Oncogene 2007, 26, 77-90; Sharma S. et al., Epigenetics Chromatin 2012. 5, 3 (2012).

There is still a need of developing compounds which show improved activity in the treatment and/or prevention of cancer, fibrosis and immunomodulation.

SUMMARY OF THE INVENTION

Inventors have found new compounds having a 3,4-heterocycloquinoline core which are capable to inhibit one or more DNA methyltransferases (DNMTs, including DNMT1, DNMT3A and/or DNMT3B) as demonstrated by the examples of the invention. These compounds are therefore inhibitors of DNMTs and could be useful for the treatment and/or prevention of cancer, fibrosis and/or immunomodulation.

Further, some compounds of the invention are also capable to inhibit the histone methyltransferase G9a being dual inhibitors. Regarding their use in cancer, these compounds of the invention have the advantage that they are addressed to two different targets of those that, in in vitro tests, cell-based assays or in animal models, have proved useful for the treatment of cancer. The fact that these compounds of the present invention have an impact on two pathophysiological events, may lead to a more efficacious treatment.

Therefore, a first aspect of the invention relates to a compound of formula (I), or a pharmaceutically or veterinary acceptable salt thereof, or any stereoisomer or mixtures thereof, either of the compound of formula (I) or of any of its pharmaceutically or veterinary acceptable salts

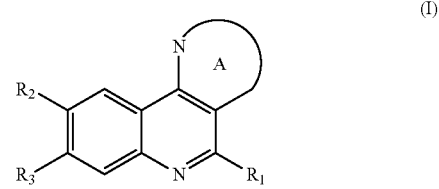

which is selected from the group consisting of compounds of formula (Ia), (Ib), (Ic), and (Id):

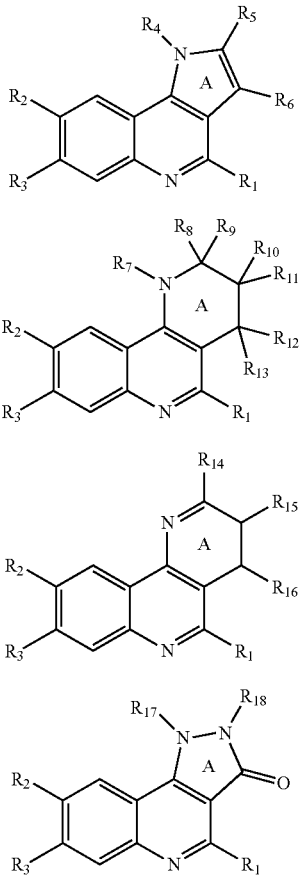

wherein

R$_1$ is selected from the group consisting of R$^a$, Cy$^1$, halogen, —NO$_2$, —CN, —OR$^b$, —OC(O)R$^{b'}$, —OC(O)OR$^{b'}$, —OC(O)NR$^b$R$^{b'}$, —NR$^b$R$^{b'}$, —NR$^b$C(O)R$^{b'}$, —NR$^b$C(O)OR$^{b'}$, —NR$^b$C(O)NR$^b$R$^{b'}$, —NR$^b$S(O)$_2$R$^{b'}$, —NR$^b$SO$_2$NR$^b$R$^{b'}$, —SR$^{b'}$, —S(O)R$^{b'}$, —S(O)OR$^{b'}$, —SO$_2$R$^{b'}$, —SO$_2$(OR$^{b'}$), —SO$_2$NR$^b$R$^{b'}$, —SC(O)NR$^b$R$^{b'}$, —C(O)R$^{b'}$, —C(O)OR$^{b'}$, —C(O)NR$^b$R$^{b'}$, —C(O)NR$^b$OR$^{b'}$, and —C(O)NR$^b$SO$_2$R$^{b'}$;

Cy$^1$ is a known ring system selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
(iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;

wherein Cy$^1$ is optionally substituted with:
a) one Cy$^2$ or one Cy$^3$, and/or
b) one or more substituents R$^c$, and/or
c) one or more substituents Z$^1$ optionally substituted with one or more substituents R$^c$ and/or one Cy$^2$;
wherein Cy$^2$ or Cy$^3$ are optionally substituted with one or more substituents independently selected from R$^c$, and Z$^2$ optionally substituted with one or more substituents R$^c$;

R$_2$ is selected from the group consisting of H, R$^g$, halogen, —NO$_2$, —CN, —OR$^{g'}$, —OC(O)R$^{g'}$, —OC(O)OR$^{g'}$, —OC(O)NR$^g$R$^{g'}$, —NR$^g$R$^{g'}$, —NR$^g$C(O)R$^{g'}$, —NR$^g$C(O)OR$^{g'}$, —NR$^g$C(O)NR$^g$R$^{g'}$, —NR$^g$S(O)$_2$R$^{g'}$, —NR$^g$SO$_2$NR$^g$R$^{g'}$, —SR$^{g'}$, —S(O)R$^{g'}$, —S(O)OR$^{g'}$, —SO$_2$R$^{g'}$, —SO$_2$(OR$^{g'}$), —SO$_2$NR$^g$R$^{g'}$, —SC(O)NR$^g$R$^{g'}$, —C(O)R$^{g'}$, —C(O)OR$^{g'}$, —C(O)NR$^g$R$^{g'}$, and —C(O)NR$^g$OR$^{g'}$, and —C(O)NR$^g$SO$_2$R$^{g'}$;

R$_3$ is selected from the group consisting of R$^d$, —OR$^d$, —NR$^d$R$^{g'}$, and —NR$^{a'}$COR$^d$; wherein R$_3$ contains at least one atom selected from N, O, S, and F;

R$_4$, R$_7$, R$_{17}$, R$_{18}$ are independently H or R$^d$;

R$_5$, R$_8$, R$_{10}$, R$_{14}$, R$_{15}$ are independently selected from the group consisting of H, R$^e$, OR$^f$, —NR$^f$R$^{g'}$, NR$^{a'}$COR$^f$, and R$^f$;

R$_6$, R$_9$, R$_{11}$, R$_{12}$, R$_{13}$, R$_{16}$ are independently selected from the group consisting of H, R$^a$, and one or more halogen atoms;

each R$^a$ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, wherein each R$^a$ is optionally substituted with one or more halogen atoms, each R$^{a'}$ is independently H or R$^a$;

each R$^b$ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, wherein any of these groups is optionally substituted with one or more halogen atoms, and Cy$^4$ optionally substituted with one or more substituents R$^c$;

each R$^{b'}$ is independently H or R$^b$;

each R$^c$ is independently selected from halogen, —NO$_2$, —CN, —OR$^{g'}$, —OC(Y)R$^{g'}$, —OC(Y)OR$^{g'}$, —OC(Y)NR$^g$R$^{g'}$, —NR$^g$R$^{g'}$, —NR$^g$C(Y)R$^{g'}$, —NR$^g$C(Y)OR$^{g'}$, —NR$^g$C(Y)NR$^g$R$^{g'}$, —NR$^g$S(O)$_2$R$^{g'}$, —NR$^g$SO$_2$NR$^g$R$^{g'}$, —SR$^{g'}$, —S(O)R$^{g'}$, —S(O)OR$^{g'}$, —SO$_2$R$^{g'}$, —SO$_2$(OR$^{g'}$), —SO$_2$NR$^g$R$^{g'}$, —SC(Y)NR$^g$R$^{g'}$, —C(Y)R$^{g'}$, —C(Y)OR$^{g'}$, —C(Y)NR$^g$R$^{g'}$, —C(Y)NR$^g$OR$^{g'}$, and —C(O)NR$^g$SO$_2$R$^{g'}$;

each R$^d$ is independently R$^e$ or R$^f$;

each R$^e$ is independently Cy$^5$ optionally substituted with:
a) one Cy$^7$; and/or
b) one or more substituents R$^c$, and/or
c) one or more substituents Z$^4$ optionally substituted with one or more substituents R$^c$ and/or one Cy$^7$;
wherein Cy$^7$ is optionally substituted with one or more substituents independently selected from R$^c$, and Z$^5$ optionally substituted with one or more substituents R$^c$; and each R$^f$ is independently Z$^3$ optionally substituted with one or more substituents R$^c$ and/or one Cy$^6$; wherein Cy$^6$ is optionally substituted with:
a) one Cy$^8$; and/or
b) one or more substituents R$^c$, and/or
c) one or more substituents Z$^6$ optionally substituted with one or more substituents R$^c$ and/or one Cy$^8$;
wherein Cy$^8$ is optionally substituted with one or more substituents independently selected from R$^c$, and Z$^7$ optionally substituted with one or more substituents R$^c$;

each R$^{f'}$ is independently H or R$^f$;

each $R^g$ is independently selected from the group consisting of $(C_1-C_6)$alkyl, $(C_2-C_6)$alkenyl, $(C_2-C_6)$alkynyl, $(C_2-C_6)$hydrocarbon chain having one or more double bonds and one or more triple bonds, and 3- to 7-membered saturated or partially unsaturated or aromatic carbocyclic or heterocyclic monocyclic ring, wherein each $R^g$ is optionally substituted with one or more halogen atoms, each $R^{g'}$ is independently H or $R^g$;

Y is O, S, or $NR^{g'}$;

$Z^1$-$Z^7$ are independently selected from the group consisting of $(C_1-C_{12})$alkyl, $(C_2-C_{12})$alkenyl, $(C_2-C_{12})$alkynyl, and $(C_2-C_6)$hydrocarbon chain having one or more double bonds and one or more triple bonds;

$Cy^2$, $Cy^7$ and $Cy^8$ are independently a known ring system selected from the group consisting of phenyl; 3- to 7-membered carbocyclic or heterocyclic monocyclic ring, saturated or partially unsaturated; and 5- or 6-membered heteroaromatic ring;

$Cy^3$, $Cy^4$, $Cy^5$ and $Cy^6$ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C_1-C_4)alkyl];

with the proviso that the compound of formula (I) is other than: 7,8-diethoxy-1,2-dihydro-4-methyl-3H-pyrrolo[3,2-c]quinolin-3-one; 7,8-diethoxy-1,2-dihydro-4-methyl-3H-pyrrolo[3,2-c]quinolin-3-one hydrochloride; 7-methoxy-1-(3-methoxyphenyl)-2,3,4-tris(trifluoromethyl)-1H-pyrrolo[3,2-c]quinoline; 8-fluoro-2,5-dihydro-4-methyl-7-(4-morpholinyl)-2-phenyl-3H-pyrazolo[4,3-c]quinolin-3-one; 8-fluoro-2,5-dihydro-4-methyl-2-phenyl-7-(1-piperazinyl)-3H-pyrazolo[4,3-c]quinolin-3-one; 2-(4-bromophenyl)-4-(butylamino)-1,2-dihydro-7,8-dimethoxy-3H-pyrazolo[4,3-c]quinolin-3-one; 2-(3-bromophenyl)-4-(butylamino)-1,2-dihydro-7,8-dimethoxy-3H-pyrazolo[4,3-c]quinolin-3-one; 4-(butylamino)-2-(4-chlorophenyl)-1,2-dihydro-7,8-dimethoxy-3H-pyrazolo[4,3-c]quinolin-3-one; 4-(butylamino)-2-(3-chlorophenyl)-1,2-dihydro-7,8-dimethoxy-3H-pyrazolo[4,3-c]quinolin-3-one; 4-(butylamino)-2-(4-fluorophenyl)-1,2-dihydro-7,8-dimethoxy-3H-pyrazolo[4,3-c]quinolin-3-one; 4-(butylamino)-2-(3-fluorophenyl)-1,2-dihydro-7,8-dimethoxy-3H-pyrazolo[4,3-c]quinolin-3-one; 4-(cyclopentylamino)-2-(3,5-difluorophenyl)-1,2-dihydro-7,8-dimethoxy-3H-pyrazolo[4,3-c]quinolin-3-one; 2-(4-bromophenyl)-4-(cyclopentylamino)-1,2-dihydro-7,8-dimethoxy-3H-pyrazolo[4,3-c]quinolin-3-one; 2-(3-bromophenyl)-4-(cyclopentylamino)-1,2-dihydro-7,8-dimethoxy-3H-pyrazolo[4,3-c]quinolin-3-one; 2-(4-chlorophenyl)-4-(cyclopentylamino)-1,2-dihydro-7,8-dimethoxy-3H-pyrazolo[4,3-c]quinolin-3-one; 2-(3-chlorophenyl)-4-(cyclopentylamino)-1,2-dihydro-7,8-dimethoxy-3H-pyrazolo[4,3-c]quinolin-3-one; 4-(cyclopentylamino)-2-(4-fluorophenyl)-1,2-dihydro-7,8-dimethoxy-3H-pyrazolo[4,3-c]quinolin-3-one; and 4-(cyclopentylamino)-2-(3-fluorophenyl)-1,2-dihydro-7,8-dimethoxy-3H-pyrazolo[4,3-c]quinolin-3-one.

A second aspect of the invention relates to a compound of formula (I), or a pharmaceutically or veterinary acceptable salt thereof, or any stereoisomer or mixtures thereof, either of the compound of formula (I) or of any of its pharmaceutically or veterinary acceptable salts

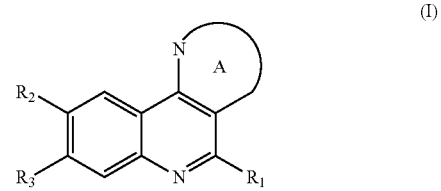

(I)

which is selected from the group consisting of compounds of formula (Ib), (Ia), (Ic), and (Id):

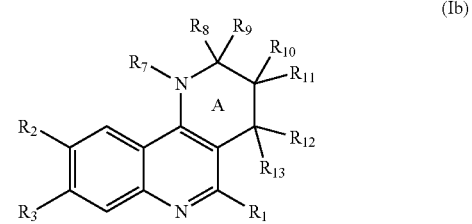

(Ib)

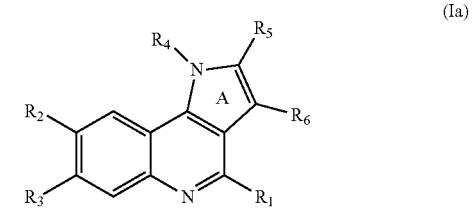

(Ia)

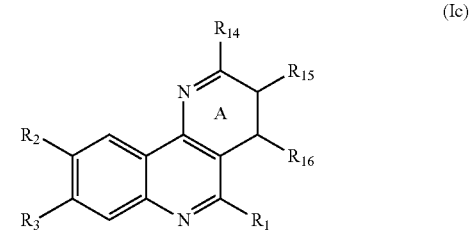

(Ic)

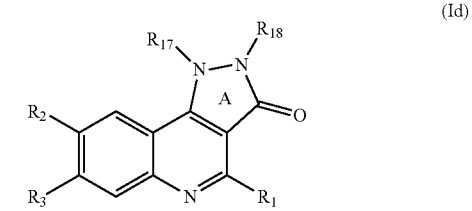

(Id)

wherein $R_1$ is $Cy^1$ and is attached to the quinoline through a carbon atom;

$Cy^1$ is a known ring system selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
(iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;
wherein $Cy^1$ is optionally substituted with:
a) one $Cy^2$ or one $Cy^3$, and/or
b) one or more substituents $R^c$, and/or
c) one or more substituents $Z^1$ optionally substituted with one or more substituents $R^c$ and/or one $Cy^2$;
wherein $Cy^2$ or $Cy^3$ are optionally substituted with one or more substituents independently selected from $R^c$, and $Z^2$ optionally substituted with one or more substituents $R^c$;
$R_2$ is selected from the group consisting of H, $R^g$, halogen, $-NO_2$, $-CN$, $-OR^{g'}$, $-OC(O)R^{g'}$, $-OC(O)OR^{g'}$, $-OC(O)NR^{g'}R^{g'}$, $-NR^{g'}R^{g'}$, $-NR^{g'}C(O)R^{g'}$, $-NR^{g'}C(O)OR^{g'}$, $-NR^{g'}C(O)NR^{g'}R^{g'}$, $-NR^{g'}S(O)_2R^{g'}$, $-NR^{g'}SO_2NR^{g'}R^{g'}$, $-SR^{g'}$, $-S(O)R^{g'}$, $-S(O)OR^{g'}$, $-SO_2R^{g'}$, $-SO_2(OR^{g'})$, $-SO_2NR^{g'}R^{g'}$, $-SC(O)NR^{g'}R^{g'}$, $-C(O)R^{g'}$, $-C(O)OR^{g'}$, $-C(O)NR^{g'}R^{g'}$, and $-C(O)NR^{g'}OR^{g'}$, and $-C(O)NR^{g'}SO_2R^{g'}$;
$R_3$ is $-OR^d$;
$R_4$, $R_7$, $R_{17}$, $R_{18}$ are independently H or $R^d$;
$R_5$, $R_8$, $R_{10}$, $R_{14}$, $R_{15}$ are independently selected from the group consisting of H, $R^e$, $OR^f$, $-NR^{f'}R^{g'}$, $NR^{a'}COR^f$, and $R^f$;
$R_6$, $R_9$, $R_{11}$, $R_{12}$, $R_{13}$, $R_{16}$ are independently selected from the group consisting of H, $R^a$, and one or more halogen atoms;
each $R^a$ is independently selected from the group consisting of $(C_1-C_6)$alkyl, $(C_2-C_6)$alkenyl, $(C_2-C_6)$alkynyl, $(C_2-C_6)$hydrocarbon chain having one or more double bonds and one or more triple bonds, wherein each $R^a$ is optionally substituted with one or more halogen atoms,
each $R^{a'}$ is independently H or $R^a$;
each $R^c$ is independently selected from halogen, $-NO_2$, $-CN$, $-OR^{g'}$, $-OC(Y)R^{g'}$, $-OC(Y)OR^{g'}$, $-OC(Y)NR^{g'}R^{g'}$, $-NR^{g'}R^{g'}$, $-NR^{g'}C(Y)R^{g'}$, $-NR^{g'}C(Y)OR^{g'}$, $-NR^{g'}C(Y)NR^{g'}R^{g'}$, $-NR^{g'}S(O)_2R^{g'}$, $-NR^{g'}SO_2NR^{g'}R^{g'}$, $-SR^{g'}$, $-S(O)R^{g'}$, $-S(O)OR^{g'}$, $-SO_2R^{g'}$, $-SO_2(OR^{g'})$, $-SO_2NR^{g'}R^{g'}$, $-SC(Y)NR^{g'}R^{g'}$, $-C(Y)R^{g'}$, $-C(Y)OR^{g'}$, $-C(Y)NR^{g'}R^{g'}$, $-C(Y)NR^{g'}OR^{g'}$, and $-C(O)NR^{g'}SO_2R^{g'}$;
each $R^d$ is independently $R^e$ or $R^f$;
each $R^e$ is independently $Cy^5$ optionally substituted with:
d) one $Cy^7$; and/or
e) one or more substituents $R^c$, and/or
f) one or more substituents $Z^4$ optionally substituted with one or more substituents $R^c$ and/or one $Cy^7$;
wherein $Cy^7$ is optionally substituted with one or more substituents independently selected from $R^c$, and $Z^5$ optionally substituted with one or more substituents $R^c$; and
each $R^f$ is independently $Z^3$ optionally substituted with one or more substituents $R^c$ and/or one $Cy^6$; wherein $Cy^6$ is optionally substituted with:
d) one $Cy^8$; and/or
e) one or more substituents $R^c$, and/or
f) one or more substituents $Z^6$ optionally substituted with one or more substituents $R^c$ and/or one $Cy^8$;
wherein $Cy^8$ is optionally substituted with one or more substituents independently selected from $R^c$, and $Z^7$ optionally substituted with one or more substituents $R^c$;
each $R^{f'}$ is independently H or $R^f$;
each $R^g$ is independently selected from the group consisting of $(C_1-C_6)$alkyl, $(C_2-C_6)$alkenyl, $(C_2-C_6)$alkynyl, $(C_2-C_6)$hydrocarbon chain having one or more double bonds and one or more triple bonds, and 3- to 7-membered saturated or partially unsaturated or aromatic carbocyclic or heterocyclic monocyclic ring, wherein each $R^g$ is optionally substituted with one or more halogen atoms,
each $R^{g'}$ is independently H or $R^g$;
Y is O, S, or $NR^{g'}$;
$Z^1$-$Z^7$ are independently selected from the group consisting of $(C_1-C_{12})$alkyl, $(C_2-C_{12})$alkenyl, $(C_2-C_{12})$alkynyl, and $(C_2-C_6)$hydrocarbon chain having one or more double bonds and one or more triple bonds;
$Cy^2$, $Cy^7$ and $Cy^8$ are independently a known ring system selected from the group consisting of phenyl; 3- to 7-membered carbocyclic or heterocyclic monocyclic ring, saturated or partially unsaturated; and 5- or 6-membered heteroaromatic ring;
$Cy^3$, $Cy^5$ and $Cy^6$ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or $C[N(C_1-C_4)alkyl]$.

A third aspect of the invention relates to a pharmaceutical or veterinary composition which comprises an effective amount of a compound of formula (I) as defined above, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

A fourth aspect of the invention relates to a compound of formula (I) or a pharmaceutical or veterinary composition as defined above, for use in the treatment and/or prevention of cancer, fibrosis and/or immunomodulation. Thus, the third aspect of the invention relates to the use of a compound of formula (I) as defined above, for the manufacture of a medicament for the treatment and/or prevention of cancer, fibrosis and/or immunomodulation; and may also be formulated as a method for the treatment and/or prevention of cancer, fibrosis and/or immunomodulation, comprising administering an effective amount of the previously defined compound of formula (I) as defined above, and one or more pharmaceutically or veterinary acceptable excipients or carriers, in a subject in need thereof, including a human.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "carbocyclic" ring system refers to a known ring system wherein all the ring members contain carbon atoms. The term "heterocyclic" ring system refers to a known ring system wherein one or more of the ring members, preferably 1, 2, 3, or 4 ring members, are selected from NH, N, O, and S, where chemically possible. The remaining ring members of the heterocyclic ring are independently selected from C, CH, CH$_2$, O, N, NH, and S. Unless otherwise specified, the "heterocyclic" ring system may be attached to the rest of the molecule through a C or a N atom of the ring system. Both the carbocyclic and heterocyclic rings can be saturated, partially unsaturated, or aromatic and may be unsubstituted or substituted as described herein, being the substituents placed on any available position. Thus, in a ring member of a carbocyclic ring that is CH or CH$_2$ or in a ring member of a heterocyclic ring that is CH, CH$_2$ or NH, one or more of the H atoms of these ring members may be substituted by another moiety as herein disclosed.

For the purposes of the present invention, in "fused" rings the fusion occurs through one bond which is common to two adjoining rings; in "bridged-fused" rings the fusion occurs through a sequence of atoms (bridgehead) which is common to two rings; and in "spiro-fused" rings, the fusion occurs through only one atom (spiro atom), preferably a carbon atom, which is common to two adjoining rings (including bridged rings).

The term "heteroaromatic" ring refers to a known aromatic ring system, wherein one or more of the ring members, preferably 1, 2, 3, or 4 ring members, are selected from NH, N, O, and S, where chemically possible. The remaining ring members of the heteroaromatic ring are independently selected from C, CH, O, N, NH, and S. The heteroaromatic ring may be unsubstituted or substituted as described herein, being the substituents placed on any available position. Thus, in a ring member of the heteroaromatic ring which is CH or NH the H atom may be substituted by another moiety, as herein disclosed.

The present invention also includes the tautomeric forms of the compounds of formula (I). The term "tautomeric isomers" means isomers, the structures of which differ in the position of an atom, generally a hydrogen atom, and of one or more multiple bonds, and which are capable of easily and reversibly changing from one to another. The tautomers are used indistinctly in the present application. Thus, as an example, a hydroxyphenyl group has to be considered equivalent to its tautomeric form: cyclohexa-2,4-dienone. As further example, a compound of formula (I) which is a compound of formula (Id) can exist as different tautomers, as shown below, when R$_{17}$ is H or when R$_{18}$ is H: All tautomers are to be considered equivalent for the purposes of the invention:

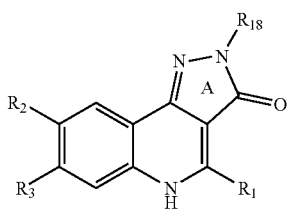

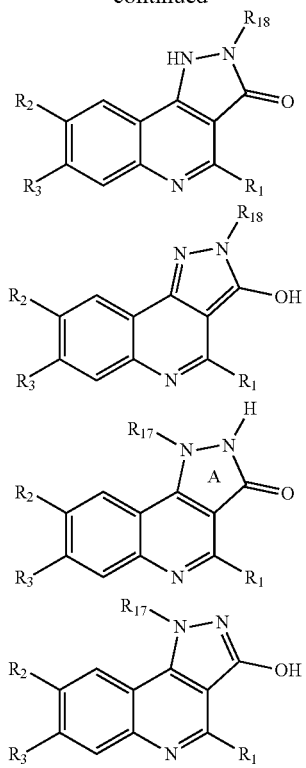

(Id) R$_{17}$ = H  (Id) R$_{18}$ = H

The term "known ring system" as used herein refers to a ring system which is chemically feasible and is known in the art and so intends to exclude those ring systems that are not chemically possible.

For the purposes of the present invention, in all saturated or partially unsaturated rings, one or two members of the rings are optionally C(O) and/or C(NH) and/or C[N(C$_1$-C$_4$) alkyl].

The term (C$_1$-C$_n$)alkyl refers to a saturated branched or linear hydrocarbon chain which contains from 1 to n carbon atoms and only single bonds. The term (C$_2$-C$_n$)alkenyl refers to an unsaturated branched or linear hydrocarbon chain which comprises from 2 to n carbon atoms and at least one or more double bonds. The term (C$_2$-C$_n$)alkynyl refers to a saturated branched or linear hydrocarbon chain which comprises from 2 to n carbon atoms and at least one or more triple bonds. For the purposes of the invention, the (C$_2$-C$_n$) hydrocarbon chain having one or more double bonds and one or more triple bonds is a branched or linear hydrocarbon chain which contains from 2 to n carbon atoms.

A halogen substituent means fluoro, chloro, bromo or iodo.

In the embodiments of the invention referring to the compounds of formula (I) or formula (II), where the substitution or unsubstitution of a certain group is not specified, e.g. either by indicating a certain substitution for that group or by indicating that the group is unsubstituted, it has to be understood that the possible substitution of this group is the one as in the definition of the formula (I) or formula (II). Further, the expression "substituted as defined herein", "substituted as previously defined" or any equivalent expression has to be understood that the possible substitution of this group is the one as in the definition of the formula (I) or formula (II).

"Protective group" (PG) refers to a grouping of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

In the first aspect of the invention related to the compounds of formula (I), the compound of the invention is other than the ones listed in table 1:

TABLE 1

| Compd. Number | Compound name (CAS Registry Number) | Chemical formula | Bibliographic references |
|---|---|---|---|
| 1 (Ia) | 7,8-diethoxy-1,2-dihydro-4-methyl-3H-pyrrolo[3,2-c]quinolin-3-one (1348739-57-0) and its hydrochloride salt (1348643-38-8) | | No references |
| 2 (Ia) | 7-methoxy-1-(3-methoxy-phenyl)-2,3,4-tris(trifluoro-methyl)-1H-pyrrolo[3,2-c]quinoline (192521-71-4) | | J. Chem. Soc., Perkin Trans. 1, 1997, (10), 1457-1463. |
| 3 (Ia) | 8-fluoro-2,5-dihydro-4-methyl-7-(4-morpholinyl)-2-phenyl-3H-pyrazolo[4,3-c]quinolin-3-one (1092483-70-9) | | US20080306049 |
| 4 (Id) | 8-fluoro-2,5-dihydro-4-methyl-2-phenyl-7-(1-piperazinyl)-3H-pyrazolo[4,3-c]quinolin-3-one (1092483-69-6) | | US20080306049 |

TABLE 1-continued

| Compd. Number | Compound name (CAS Registry Number) | Chemical formula | Bibliographic references |
|---|---|---|---|
| 5 (Id) | 2-(4-bromophenyl)-4-(butylamino)-1,2-dihydro-7,8-dimethoxy-3H-pyrazolo[4,3-c]quinolin-3-one (910045-56-6) | | CN1830978 |
| 6 (Id) | 2-(3-bromophenyl)-4-(butylamino)-1,2-dihydro-7,8-dimethoxy-3H-pyrazolo[4,3-c]quinolin-3-one (910045-55-5) | | CN1830978 |
| 7 (Id) | 4-(butylamino)-2-(4-chlorophenyl)-1,2-dihydro-7,8-dimethoxy-3H-pyrazolo[4,3-c]quinolin-3-one (910045-54-4) | | CN1830978 |
| 8 (Id) | 4-(butylamino)-2-(3-chlorophenyl)-1,2-dihydro-7,8-dimethoxy-3H-pyrazolo[4,3-c]quinolin-3-one (910045-53-3) | | CN1830978 |
| 9 (Id) | 4-(butylamino)-2-(4-fluorophenyl)-1,2-dihydro-7,8-dimethoxy-3H-pyrazolo[4,3-c]quinolin-3-one (910045-52-2) | | CN1830978 |

TABLE 1-continued

| Compd. Number | Compound name (CAS Registry Number) | Chemical formula | Bibliographic references |
|---|---|---|---|
| 10 (Id) | 4-(butylamino)-2-(3-fluorophenyl)-1,2-dihydro-7,8-dimethoxy-3H-pyrazolo[4,3-c]quinolin-3-one (910045-51-1) | | CN1830978 |
| 11 (Id) | 4-(cyclopentylamino)-2-(3,5-difluorophenyl)-1,2-dihydro-7,8-dimethoxy-3H-pyrazolo[4,3-c]quinolin-3-one (910045-50-0) | | CN1830978 |
| 12 (Id) | 2-(4-bromophenyl)-4-(cyclopentylamino)-1,2-dihydro-7,8-dimethoxy-3H-pyrazolo[4,3-c]quinolin-3-one (910045-49-7) | | CN1830978 |
| 13 (Id) | 2-(3-bromophenyl)-4-(cyclopentylamino)-1,2-dihydro-7,8-dimethoxy-3H-pyrazolo[4,3-c]quinolin-3-one (910045-48-6) | | CN1830978 |

TABLE 1-continued

| Compd. Number | Compound name (CAS Registry Number) | Chemical formula | Bibliographic references |
|---|---|---|---|
| 14 (Id) | 2-(4-chlorophenyl)-4-(cyclopentylamino)-1,2-dihydro-7,8-dimethoxy-3H-pyrazolo[4,3-c]quinolin-3-one (910045-47-5) | | CN1830978 |
| 15 (Id) | 2-(3-chlorophenyl)-4-(cyclopentylamino)-1,2-dihydro-7,8-dimethoxy-3H-pyrazolo[4,3-c]quinolin-3-one (910045-46-4) | | CN1830978 |
| 16 (Id) | 4-(cyclopentylamino)-2-(4-fluorophenyl)-1,2-dihydro-7,8-dimethoxy-3H-pyrazolo[4,3-c]quinolin-3-one (910045-45-3) | | CN1830978 |
| 17 (Id) | 4-(cyclopentylamino)-2-(3-fluorophenyl)-1,2-dihydro-7,8-dimethoxy-3H-pyrazolo[4,3-c]quinolin-3-one (910045-44-2) | | CN1830978 |

As can be seen in the table above the cited compounds are either commercial products with no associated bibliographic references or are disclosed in the references US20080306049 (Therapeutic pyrazoloquinoline derivatives); Chambers R D., et al., Journal of the Chemical Society, Perkin Transactions 1: Organic and Bio-Organic Chemistry (1997), (10), 1457-1463; and CN1830978 (Pyrazolo [4,3c]-quinolin-3-one compound, prepn. method and use thereof). None of these documents describes the ability of these compounds to inhibit the histone methyltransferase G9a and/or the DNA methyltransferases (DNMT1, DNMT3A or DNMT3B), nor their use in the treatment and/or prevention of cancer, fibrosis and/or immunomodulation.

There is no limitation on the type of salt of the compounds of the invention that can be used, provided that these are pharmaceutically or veterinary acceptable when they are used for therapeutic purposes. The term "pharmaceutically or veterinary acceptable salts", embraces salts commonly used to form alkali metal salts and to form addition salts of free acids or free bases.

The preparation of pharmaceutically or veterinary acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically or veterinary acceptable base or acid in water or in an organic solvent or in a mixture of them. The compounds of formula (I) and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically or veterinary acceptable solvents such as water, ethanol and the like are equivalent to the unsolvated form for the purposes of the invention.

Some compounds of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

In all embodiments of the invention referring to the compounds of formula (I), the pharmaceutically or veterinary acceptable salts thereof and the stereoisomers or mixtures thereof, either of any of the compounds of formula (I) or of any of their pharmaceutically acceptable salts are always contemplated even if they are not specifically mentioned.

In one embodiment, optionally in combination with one or more features of the various embodiments described above or below, the invention relates to a compound of formula (I) as previously described, which is a compound of formula (Ia).

In another embodiment, optionally in combination with one or more features of the various embodiments described above or below, the invention relates to a compound of formula (I) as previously described, which is a compound of formula (Ib).

In another embodiment, optionally in combination with one or more features of the various embodiments described above or below, the invention relates to a compound of formula (I) as described in the first aspect, wherein $R_1$ is selected from the group consisting of $R^a$, $Cy^1$, $-OR^b$, $-NR^{b'}R^{b'}$, $-NR^{b'}C(O)R^{b'}$, $-NR^{b'}S(O)_2R^{b'}$, $-SO_2NR^{b'}R^{b'}$, and $-C(O)NR^{b'}R^{b'}$; wherein $Cy^1$ is optionally substituted as previously defined.

In another embodiment, optionally in combination with one or more features of the various embodiments described above or below, the invention relates to a compound of formula (I) as described in the first aspect, wherein $R_1$ is $Cy^1$ optionally substituted as previously defined. More particularly, $Cy^1$ is a known ring system selected from the group consisting of:
  (i) phenyl;
  (ii) 5- or 6-membered heteroaromatic ring;
  (iii) 3- to 7-membered carbocyclic or heterocyclic monocyclic ring, which is saturated or partially unsaturated;
  (iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
and even more particularly, $R_1$ is $Cy^1$ optionally substituted as previously defined, wherein $Cy^1$ is a known ring system selected from the group consisting of (i), (ii), and (iii), as defined above.

In another embodiment, optionally in combination with one or more features of the various embodiments described above or below, the invention relates to a compound of formula (I) as described in the first aspect, wherein $R_1$ is $Cy^1$ optionally substituted as previously defined and is attached to the quinoline through a carbon atom.

In another embodiment, optionally in combination with one or more features of the various embodiments described above or below, the invention relates to a compound of formula (I) as previously described, wherein $R_1$ is selected from the group consisting of phenyl, 5- to 6-membered heteroaromatic monocyclic ring, and 4- to 6-membered saturated carbocyclic or heterocyclic monocyclic ring, being $R_1$ optionally substituted as previously defined. More particularly, $R_1$ is a 5- to 6-membered heteroaromatic monocyclic ring attached to the quinoline through a carbon atom and optionally substituted as previously defined, and even more particularly, $R_1$ is selected from the group consisting of 2-thiophene, 3-thiophene, 2-pyrrol, 3-pyrrol, 2-furan and 3-furan. In a more particular embodiment, $R_1$ is selected from the group consisting of 2-thiophene, 3-thiophene, 2-pyrrol, 3-pyrrol, 2-furan and 3-furan, wherein $R_1$ is optionally substituted with one or more groups $(C_1-C_6)$alkyl.

In another embodiment, optionally in combination with one or more features of the various embodiments described above or below, the invention relates to a compound of formula (I) as previously described, wherein $R_1$ is selected from the group consisting of the following moieties:

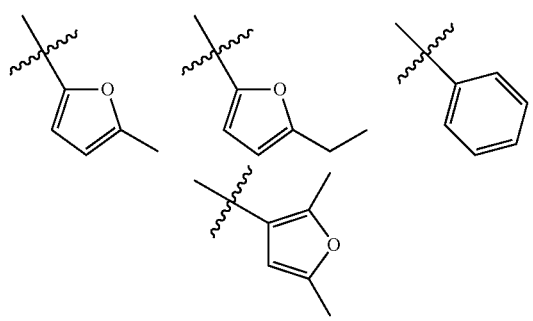

In another embodiment, optionally in combination with one or more features of the various embodiments described above or below, the invention relates to a compound of formula (I) as previously described, wherein $R_2$ is selected from H, halogen, —CN and —OR$^{g'}$, more particularly, $R_2$ is selected from H, halogen and —OR$^{g'}$; even more particularly, $R_2$ is H or —OR$^g$; and even more particularly $R_2$ is —OR$^g$ wherein R$^g$ is $(C_1\text{-}C_6)$alkyl optionally substituted with one or more halogen atoms. Even more particularly, $R_2$ is —OCH$_3$.

In another embodiment, optionally in combination with one or more features of the various embodiments described above or below, the invention relates to a compound of formula (I) as described in the first aspect, wherein $R_3$ is selected from the group consisting of —OR$^d$ and —NR$^d$R$^{g'}$. More particularly, $R_3$ is —OR$^d$, and even more particularly R$^d$ in $R_3$ is a moiety which contains at least one N atom.

In another embodiment, optionally in combination with one or more features of the various embodiments described above or below, the invention relates to a compound of formula (I) as previously described, wherein R$^d$ in $R_3$ is $Z^3$, wherein $Z^3$ is $(C_1\text{-}C_6)$alkyl substituted with one or more substituents as previously defined, more particularly in the latter embodiment, $Z^3$ is $(C_1\text{-}C_6)$alkyl substituted with Cy$^6$, wherein Cy$^6$ is optionally substituted as previously defined; even more particularly, in the latter embodiment, Cy$^6$ is a 3- to 7-membered carbocyclic or heterocyclic monocyclic ring, saturated or partially unsaturated.

In another embodiment, optionally in combination with one or more features of the various embodiments described above or below, the invention relates to a compound of formula (I) as previously described, wherein $R_3$ is a moiety of formula (XL):

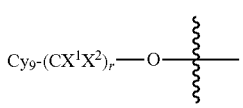

(XL)

wherein

Cy$_9$ is a 3- to 7-membered saturated or partially unsaturated or aromatic carbocyclic or heterocyclic monocyclic ring or a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring, and Cy$_9$ is optionally substituted with one or more substituents selected from halogen and $(C_1\text{-}C_3)$alkyl optionally substituted with one or more halogen atoms, $X^1$ and $X^2$ are independently H or halogen, and
r is a value selected from 0 to 6.

More particularly, $R_3$ is a moiety of formula (XL) wherein Cy$_9$ is a 3- to 7-membered saturated heterocyclic monocyclic ring or a 3- to 7-membered saturated carbocyclic or heterocyclic monocyclic ring, which is spiro-fused to a 3- to 7-membered saturated carbocyclic or heterocyclic monocyclic ring, and Cy$_9$ is optionally substituted as previously defined, $X^1$ and $X^2$ are H, and r is a value selected from 0 to 6.

In another embodiment, optionally in combination with one or more features of the various embodiments described above or below, the invention relates to a compound of formula (I) as previously described, wherein $R_3$ is selected from the group consisting of the following moieties:

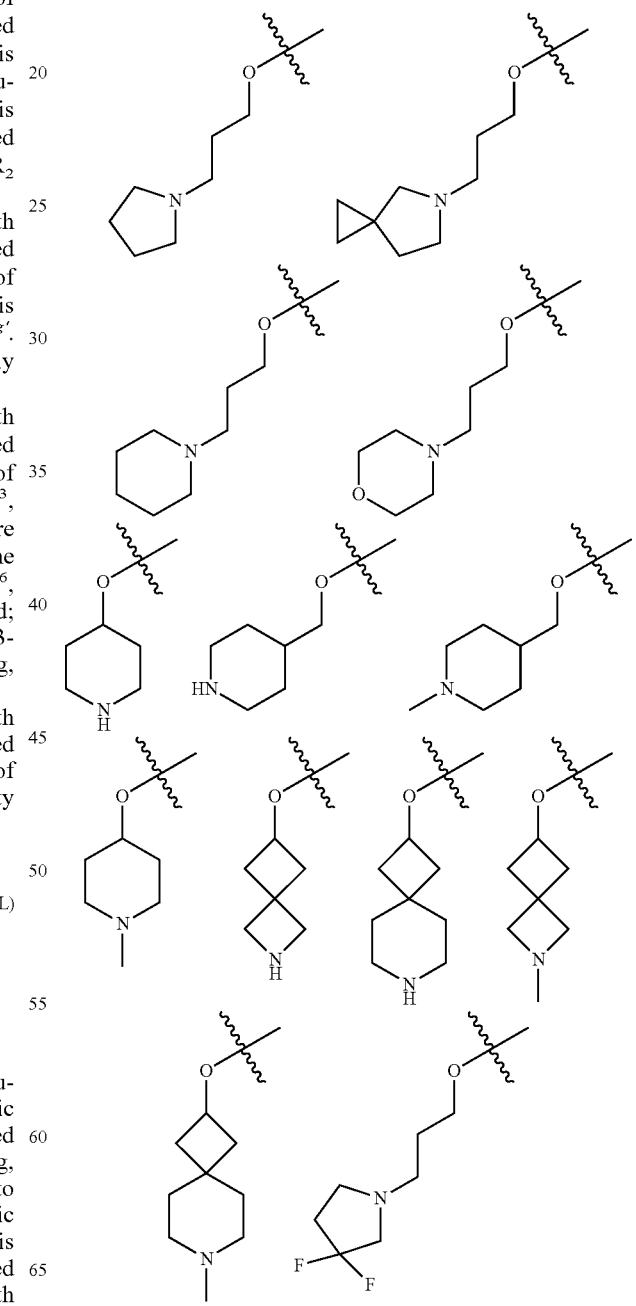

-continued

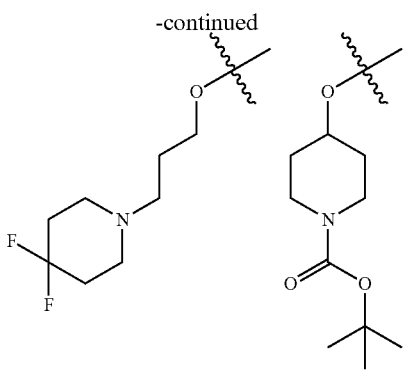

In another embodiment, optionally in combination with one or more features of the various embodiments described above or below, the invention relates to a compound of formula (I) as previously described, wherein $R_5$, $R_8$, $R_{10}$, $R_{14}$, $R_{15}$ are independently selected from the group consisting of H, $R^e$, and $R^f$.

In another embodiment, optionally in combination with one or more features of the various embodiments described above or below, the invention relates to a compound of formula (I) as previously described, wherein $R_8$ is H and $R_{10}$ is $R^e$ or $R^f$, or alternatively, $R_8$ is $R^e$ or $R^f$, and $R_{10}$ is H.

In another embodiment, optionally in combination with one or more features of the various embodiments described above or below, the invention relates to a compound of formula (I) as previously described, wherein $R_{14}$ is H and $R_{15}$ is $R^e$ or $R^f$, or alternatively, $R_{14}$ is $R^e$ or $R^f$, and $R_{15}$ is H.

In another embodiment, optionally in combination with one or more features of the various embodiments described above or below, the invention relates to a compound of formula (I) as previously described, wherein $R_6$, $R_9$, $R_{11}$, $R_{12}$, $R_{13}$, and $R_{16}$ are H.

In another embodiment, optionally in combination with one or more features of the various embodiments described above or below, the invention relates to a compound of formula (I) as previously described, wherein $R_4$ and $R_7$ are H.

In another embodiment, optionally in combination with one or more features of the various embodiments described above or below, the invention relates to a compound of formula (I) as previously described, wherein $R_{17}$ is H and $R_{18}$ is $R^d$, or alternatively, $R_{17}$ is $R^d$ and $R_{18}$ is H.

In another embodiment, optionally in combination with one or more features of the various embodiments described above or below, the invention relates to a compound of formula (I) as previously described, wherein $R_4$-$R_{18}$ are H.

In another embodiment, optionally in combination with one or more features of the various embodiments described above or below, the invention relates to a compound of formula (I) as previously described, wherein one of $R_4$-$R_6$ is other than H and the others of $R_4$-$R_6$ are H, or wherein one of $R_7$-$R_{13}$ is other than H and the others of $R_7$-$R_{13}$ are H, or wherein one of $R_{14}$-$R_{16}$ is other than H and the others of $R_{14}$-$R_{16}$ are H, or wherein one of $R_{17}$ and $R_{18}$ is other than H and the other of $R_{17}$ and $R_{18}$ is H.

In another embodiment, optionally in combination with one or more features of the various embodiments described above or below, the invention relates to a compound of formula (I) as previously described, wherein $R_6$, $R_9$, $R_{11}$-$R_{13}$ and $R_{16}$ are H; one of $R_4$-$R_5$ is other than H and the other of $R_4$-$R_5$ is H; one of $R_7$, $R_8$ and $R_{10}$ is other than H and the others of $R_7$, $R_8$ and $R_{10}$ are H; one of $R_{14}$-$R_{15}$ is other than H and the other of $R_{14}$-$R_{15}$ is H; and one of $R_{17}$ and $R_{18}$ is other than H and the other of $R_{17}$ and $R_{18}$ is H. In a more particular embodiment, $R_4$, $R_6$, $R_7$, $R_9$-$R_{13}$ and $R_{15}$-$R_{17}$ are H; and $R_5$, $R_8$, $R_{14}$ and $R_{18}$ are other than H.

More particularly, in the latter two embodiments, the substituents $R_4$-$R_{18}$ that are other than H are independently a ($C_1$-$C_{12}$)alkyl optionally substituted with one o more substituents selected from the group consisting of:
halogen,
—$NR^{g'}R^{g'}$,
—$NR^{g'}C(O)R^{g'}$, and
$Cy^6$ optionally substituted with one o more substituents selected from the group consisting of:
halogen,
—$NR^{g'}R^{g'}$,
—$NR^{g'}C(O)R^{g'}$,
—$C(O)R^{g'}$,
—($C_1$-$C_6$)alkyl optionally substituted with one or more halogen atoms; and
a 3- to 7-membered carbocyclic or heterocyclic monocyclic ring, which is saturated or partially unsaturated;
wherein $Cy^6$ is a 3- to 7-membered carbocyclic or heterocyclic saturated or partially unsaturated monocyclic ring; or a 3- to 7-membered saturated carbocyclic or heterocyclic monocyclic ring, which is spiro-fused to a 3- to 7-membered saturated carbocyclic or heterocyclic monocyclic ring, and each $R^{g'}$ is independently selected from H or ($C_1$-$C_6$)alkyl optionally substituted with one or more halogen atoms.

Even more particularly, in this embodiment, the substituents $R_4$-$R_{18}$ that are other than H, preferably $R_5$, $R_8$, $R_{14}$ and $R_{18}$, are independently a ($C_1$-$C_{12}$)alkyl substituted with $Cy^6$ optionally substituted with one o more substituents selected from the group consisting of:
halogen,
—$C(O)R^{g'}$,
—($C_1$-$C_6$)alkyl optionally substituted with one or more halogen atoms; and
a 3- to 7-membered saturated carbocyclic monocyclic ring;
wherein $Cy^6$ is a 3- to 7-membered carbocyclic or heterocyclic saturated or partially unsaturated monocyclic ring; or a 3- to 7-membered saturated carbocyclic or heterocyclic monocyclic ring, which is spiro-fused to a 3- to 7-membered saturated carbocyclic or heterocyclic monocyclic ring, and $R^{g'}$ is H or ($C_1$-$C_6$)alkyl optionally substituted with one or more halogen atoms.

Even more particularly, in this embodiment, the substituents $R_4$-$R_{18}$ that are other than H, preferably $R_5$, $R_8$, $R_{14}$ and $R_{18}$, are selected from the group consisting of methyl and a moiety selected from the following ones:

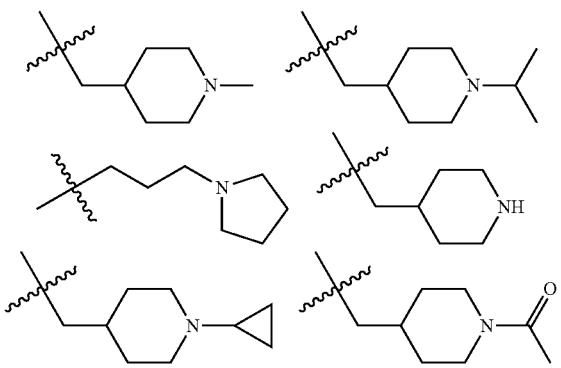

-continued

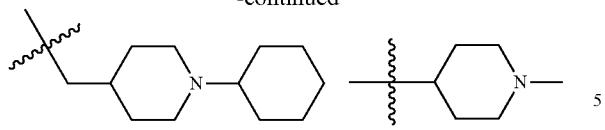

The embodiments defined above apply to all the compounds of formula (I), i.e., defined in any of the aspects and embodiments of the invention, when possible.

In another embodiment of the invention, the compound of formula (I) is selected from the group consisting of:

1-01

1-02

1-03

1-04

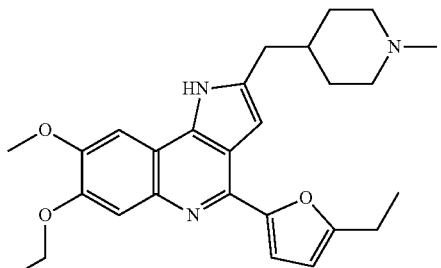

1-05

1-06

In another embodiment of the invention, the compound of formula (I) is selected from the group consisting of:

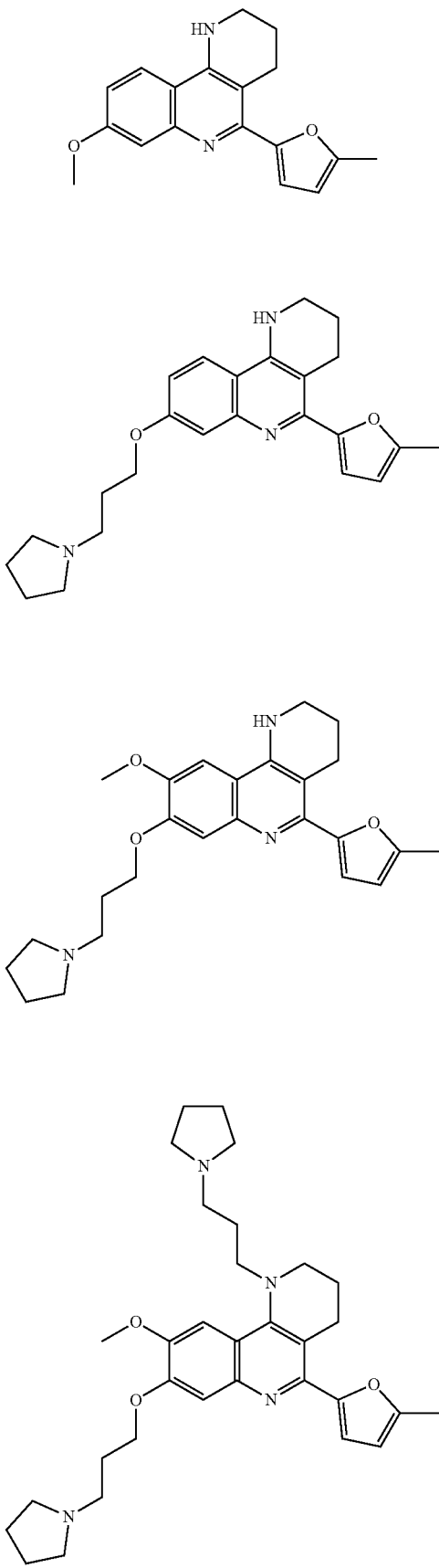
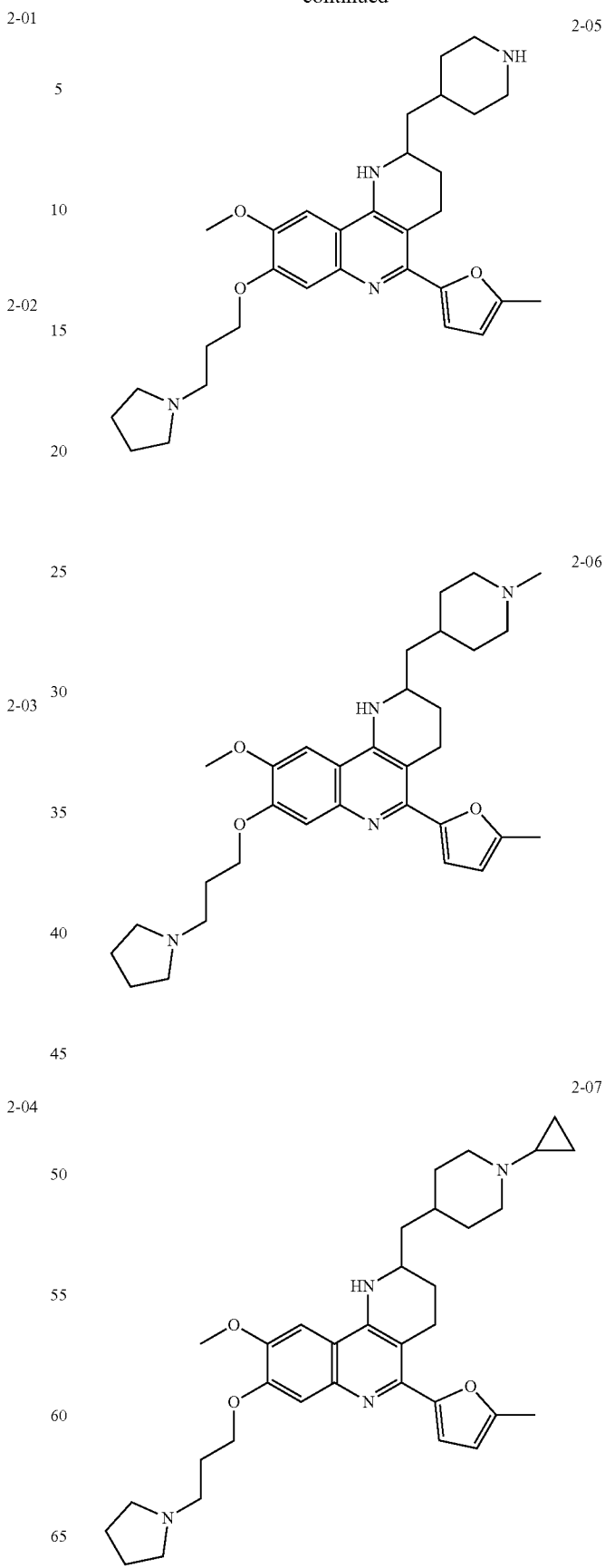

2-08
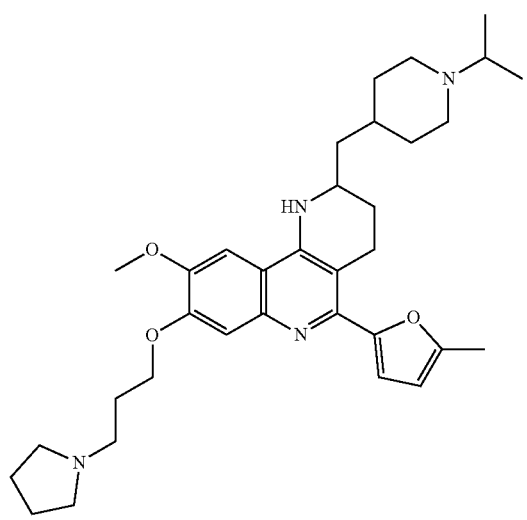
2-09
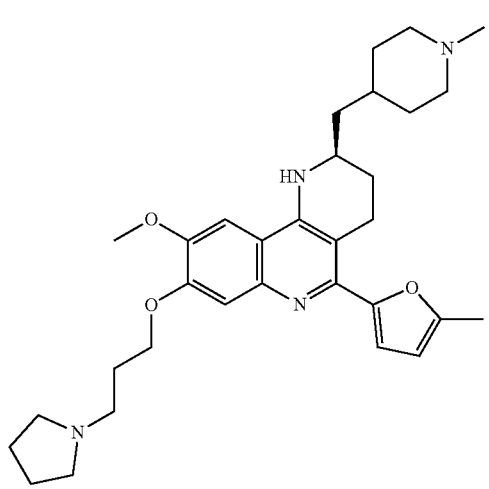
2-10
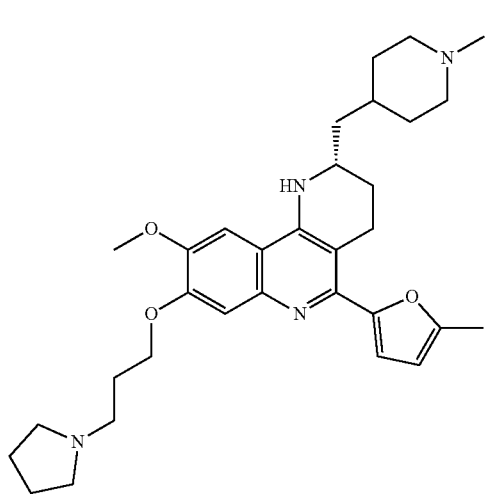
2-11
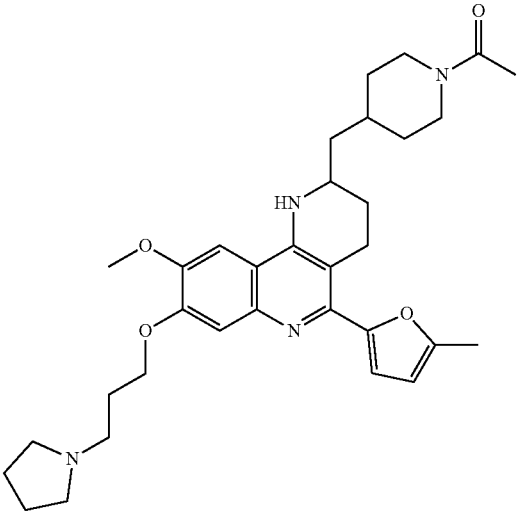
2-12
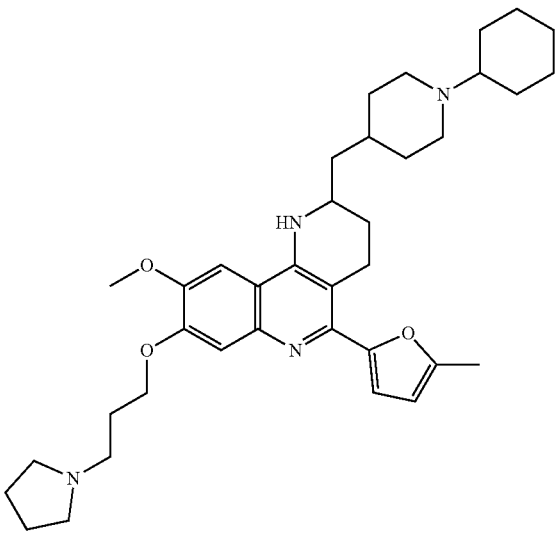
2-13
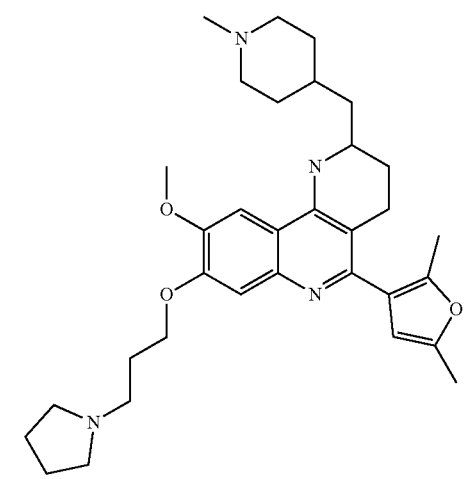
In another embodiment of the invention, the compound of formula (I) is selected from the group consisting of:

3-01
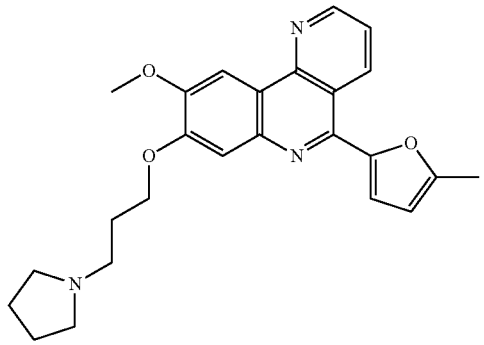
3-02
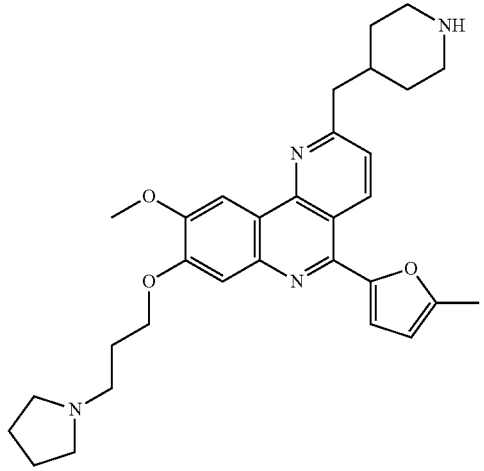
3-03
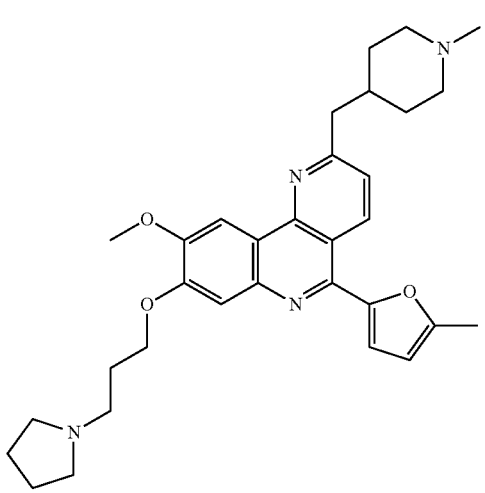
3-04
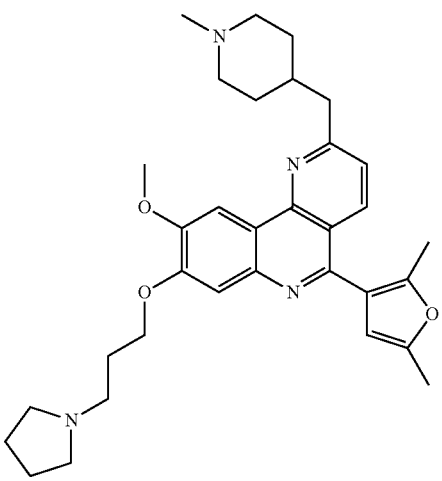
In another embodiment of the invention, the compound of formula (I) is selected from the group consisting of:
4-01
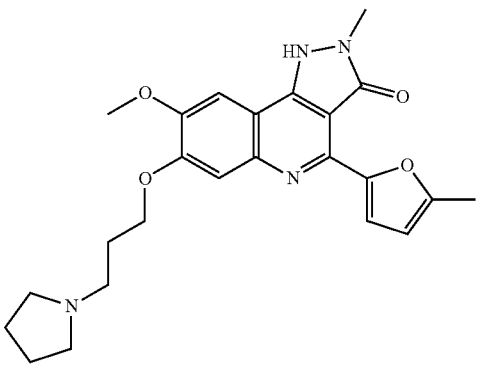
4-02
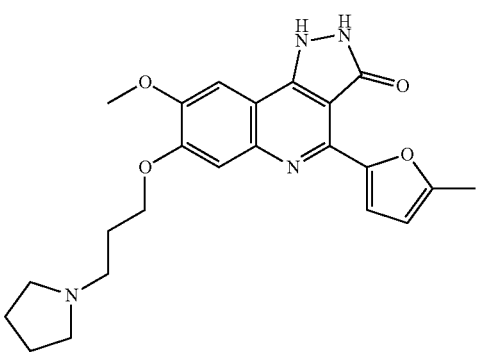

4-03

[Chemical structure of compound 4-03]

4-04

[Chemical structure of compound 4-04]

4-05

[Chemical structure of compound 4-05]

The inventors have found that compounds of formula (II) also comprising a 3,4-heterocyclo-quinoline are also inhibitors of DNMT. Thus, the present invention also relates to a compound of formula (II), or a pharmaceutically or veterinary acceptable salt thereof, or any stereoisomer or mixtures thereof, either of the compound of formula (I) or of any of its pharmaceutically or veterinary acceptable salts

[Chemical structure of formula (II)]

(II)

which is selected from the group consisting of compounds of formula (IIa), and (IIb):

[Chemical structure of formula (IIa)]

(IIa)

[Chemical structure of formula (IIb)]

(IIb)

wherein $R_1'$ is selected from the group consisting of $R^h$, $Cy^{1'}$, halogen, —$NO_2$, —CN, —$OR^{i'}$, —$OC(O)R^{i'}$, —$OC(O)OR^{i'}$, —$OC(O)NR^{i'}R^{i'}$, —$NR^{i'}R^{i'}$, —$NR^{i'}C(O)R^{i'}$, —$NR^{i'}C(O)OR^{i'}$, —$NR^{i'}C(O)NR^{i'}R^{i'}$, —$NR^{i'}S(O)_2R^{i'}$, —$NR^{i'}SO_2NR^{i'}R^{i'}$, —$SR^{i'}$, —$S(O)R^{i'}$, —$S(O)OR^{i'}$, —$SO_2R^{i'}$, —$SO_2(OR^{i'})$, —$SO_2NR^{i'}R^{i'}$, —$SC(O)NR^{i'}R^{i'}$, —$C(O)R^{i'}$, —$C(O)OR^{i'}$, —$C(O)NR^{i'}R^{i'}$, —$C(O)NR^{i'}OR^{i'}$, and —$C(O)NR^{i'}SO_2R^{i'}$;

$Cy^{1'}$ is a known ring system selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
(iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;

wherein $Cy^{1'}$ is optionally substituted with:
a) one $Cy^{2'}$ or one $Cy^{3'}$, and/or
b) one or more substituents $R^j$, and/or
c) one or more substituents $Z^{1'}$ optionally substituted with one or more substituents $R^j$ and/or one $Cy^{2'}$;

wherein $Cy^{2'}$ or $Cy^{3'}$ are optionally substituted with one or more substituents independently selected from $R^j$, and $Z^{2'}$ optionally substituted with one or more substituents $R^j$;

$R_2$' is selected from the group consisting of R″, halogen, —NO$_2$, —CN, —OR‴, —OC(O)R‴, —OC(O)OR‴, —OC(O)NR″R‴, —NR″R‴, —NR″C(O)R‴, —NR″C(O)OR‴, —NR″C(O)NR″R‴, —NR″S(O)$_2$R‴, —NR″SO$_2$NR″R‴, —SR‴, —S(O)R‴, —S(O)OR‴, —SO$_2$R‴, —SO$_2$(OR‴), —SO$_2$NR″R‴, —SC(O)NR″R‴, —C(O)R‴, —C(O)OR‴, —C(O)NR″R‴, and —C(O)NR″OR‴, and —C(O)NR‴SO$_2$R‴;

$R_3$' is selected from the group consisting of $R^k$, —OR$^k$, —NR$^k$R″, and —NR$^{h'}$COR$^k$; wherein $R_3$' contains at least one atom selected from N, O, S, and F;

$R_4$' and $R_6$' are independently selected from the group consisting of H, R$^l$, OR$^m$, —NR$^{m'}$R″, NR$^{h'}$COR$^m$, and R$^m$;

$R_5$' and $R_7$' are independently selected from the group consisting of H, R$^h$, and one or more halogen atoms;

each R$^h$ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, wherein each R$^h$ is optionally substituted with one or more halogen atoms, each R$^{h'}$ is independently H or R$^h$;

each R$^i$ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, wherein any of these groups is optionally substituted with one or more halogen atoms, and Cy$^{4'}$ optionally substituted with one or more substituents R$^j$;

each R$^{i'}$ is independently H or R$^i$;

each R$^j$ is independently selected from halogen, —NO$_2$, —CN, —OR″, —OC(Y)R″, —OC(Y)OR″, —OC(Y)NR″R‴, —NR″R‴, —NR″C(Y)R‴, —NR″C(Y)OR‴, —NR″C(Y)NR″R‴, —NR″S(O)$_2$R‴, —NR″SO$_2$NR″R‴, —SR‴, —S(O)R‴, —S(O)OR‴, —SO$_2$R‴, —SO$_2$(OR‴), —SO$_2$NR″R‴, —SC(Y)NR″R‴, —C(Y)R‴, —C(Y)OR‴, —C(Y)NR″R‴, —C(Y)NR″OR‴, and —C(O)NR‴SO$_2$R‴;

each R$^k$ is independently R$^l$ or R$^m$;

each R$^l$ is independently Cy$^{5'}$ optionally substituted with:
a) one Cy$^{7'}$; and/or
b) one or more substituents R$^j$, and/or
c) one or more substituents Z$^{4'}$ optionally substituted with one or more substituents R$^j$ and/or one Cy$^{7'}$;
wherein Cy$^{7'}$ is optionally substituted with one or more substituents independently selected from R$^j$, and Z$^{5'}$ optionally substituted with one or more substituents R$^j$; and each R$^m$ is independently Z$^{3'}$ optionally substituted with one or more substituents R$^j$ and/or one Cy$^{6'}$; wherein Cy$^{6'}$ is optionally substituted with:
a) one Cy$^{8'}$; and/or
b) one or more substituents R$^j$, and/or
c) one or more substituents Z$^{6'}$ optionally substituted with one or more substituents R$^j$ and/or one Cy$^{8'}$;
wherein Cy$^{8'}$ is optionally substituted with one or more substituents independently selected from R$^j$, and Z$^{7'}$ optionally substituted with one or more substituents R$^j$;

each R$^{m'}$ is independently H or R$^m$;

each R″ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, and 3- to 7-membered saturated or partially unsaturated or aromatic carbocyclic or heterocyclic monocyclic ring, wherein each R″ is optionally substituted with one or more halogen atoms, each R″′ is independently H or R″;

Y is O, S, or NR‴;

Z$^{1'}$-Z$^{7'}$ are independently selected from the group consisting of (C$_1$-C$_{12}$)alkyl, (C$_2$-C$_{12}$)alkenyl, (C$_2$-C$_{12}$)alkynyl, and (C$_2$-C$_6$)hydrocarbon chain having one or more double bonds and one or more triple bonds;

Cy$^{2'}$, Cy$^{7'}$ and Cy$^{8'}$ are independently a known ring system selected from the group consisting of phenyl; 3- to 7-membered carbocyclic or heterocyclic monocyclic ring, saturated or partially unsaturated; and 5- or 6-membered heteroaromatic ring;

Cy$^{3'}$, Cy$^{4'}$, Cy$^{5'}$ and Cy$^{6'}$ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C$_1$-C$_4$)alkyl].

In one embodiment, optionally in combination with one or more features of the various embodiments described above or below, the invention relates to a compound of formula (II), wherein $R_1$' is selected from the group consisting of R$^h$, Cy$^{1'}$, —OR$^i$, —NR$^i$R$^{i'}$, —NR$^{i'}$C(O)R$^{i'}$, —NR$^{i'}$S(O)$_2$R$^{i'}$, —SO$_2$NR$^i$R$^{i'}$, and —C(O)NR$^i$R$^{i'}$; wherein Cy$^{1'}$ is optionally substituted as previously defined. More particularly, $R_1$' is Cy$^{1'}$ optionally substituted as previously defined. Even more particularly, Cy$^{1'}$ is a known ring system selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
wherein Cy$^{1'}$ is optionally substituted as previously defined.

In another embodiment, optionally in combination with one or more features of the various embodiments described above or below, the invention relates to a compound of formula (II), wherein $R_2$' is selected from halogen, —CN and —OR″. More particularly, $R_2$' is —OR″.

In another embodiment, optionally in combination with one or more features of the various embodiments described above or below, the invention relates to a compound of formula (II), wherein $R_3$' is selected from the group consisting of —OR$^k$ and —NR$^k$R″. More particularly, $R_3$' is —OR$^k$. Even more particularly, R$^k$ is a moiety which contains at least one N atom.

In another embodiment, optionally in combination with one or more features of the various embodiments described above or below, the invention relates to a compound of formula (II), wherein R$^k$ in $R_3$' is Z$^{3'}$, wherein Z$^{3'}$ is (C$_1$-C$_6$)alkyl substituted with one or more substituents as previously defined.

Further, the embodiments defined above for the group $R_5$ in a compound of formula (I) also apply to the groups $R_4$' and $R_6$' in a compound of formula (II), and the embodiments defined above for the group $R_6$ in a compound of formula (I) also apply to the groups $R_5$' and $R_7$' in a compound of formula (II).

Processes for the preparation of compounds of formula (I) are also part of the invention as well as intermediates used in these processes.

For example, a compound of formula (I) which is a compound of formula (Ia) wherein $R_6$ is H (i.e., a compound (Ia')) can be obtained from a compound of formula (III):

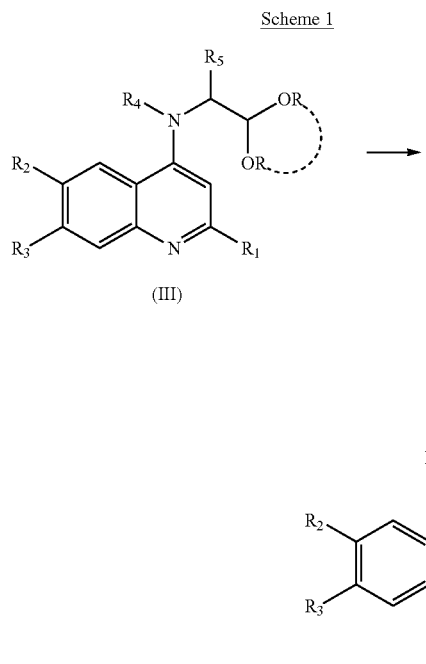

Scheme 1

(III)

(Ia')

wherein $R_1$-$R_5$ are as previously defined, and R is ($C_1$-$C_6$)alkyl or alternatively, the two adjacent groups —OR form a 5- or 6-membered ring together with the atom to which they are attached.

This conversion may be carried out in the presence of $BF_3.Et_2O$, in the presence of a suitable solvent, such as e.g. dichloromethane (DCM), at a suitable temperature, preferably cooling, particularly at about 0° C. Alternatively, this conversion can also be carried out in the presence of $TiCl_4$, in the presence of a suitable solvent, such as e.g. dichloroethane or dichloromethane (DCM), at a suitable temperature, preferably heating, particularly at about 60° C., and then reacting the intermediate obtained with $(HCHO)_n$ or acetone, in the presence of AcOH or HCOOH and a reducing agent such as $NaBH_3CN$, in the presence of a suitable solvent such as methanol or isopropanol, at a suitable temperature, preferably heating, particularly at about 50-60° C.

A compound of formula (III) can be obtained from a quinoline of formula (VII) which is converted into a quinoline of formula (V), that is subsequently reacted with a compound of formula (IV) as shown in the scheme below:

Scheme 2

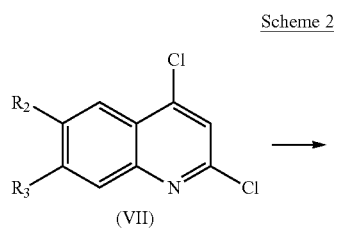

(VII)

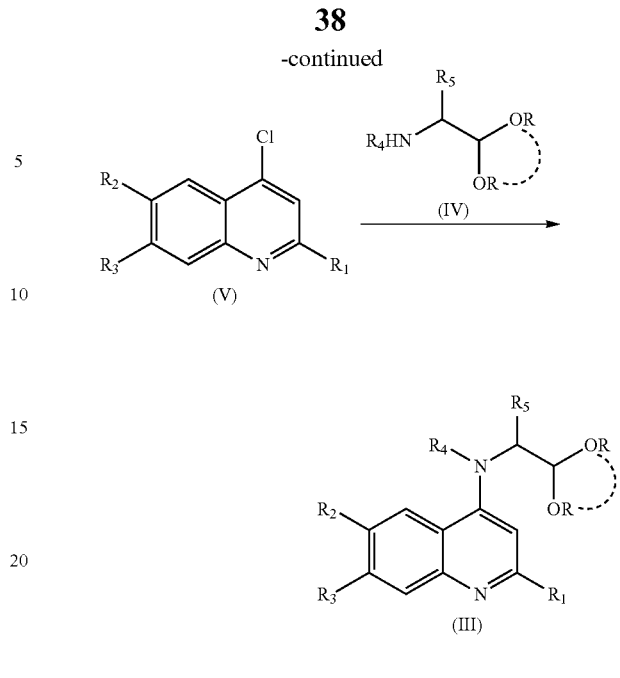

(V)

(III)

wherein $R_1$-$R_5$ are as previously defined, and R is ($C_1$-$C_6$)alkyl or alternatively, the two adjacent groups —OR form a 5- or 6-membered ring together with the atom to which they are attached For example, when $R_1$ is $R^a$ or $Cy^1$, the first conversion may be carried out with a boronic derivative of formula $R_1B(OR')_2$ (VIa), wherein $R_1$ is $R^a$ or $Cy^1$, and R' is H, ($C_1$-$C_6$)alkyl or, alternatively, two R' groups together with the B atom to which they are attached may form a cycle, in the presence of a palladium catalyst, such as e.g. Tetrakis (triphenyl-phosphine)palladium(0) ($Pd(PPh_3)_4$) and a base, such as e.g. $K_2CO_3$ or $Na_2CO_3$, in a suitable solvent, such as e.g. dioxane optionally mixed with water, at a suitable temperature, preferably heating, particularly at about 80-110° C.

When $R_1$ is —$OR^b$, the first conversion may be carried out with an alcohol of formula $R^bOH$ (VIb) in the presence of a metal such as e.g. Na, in a suitable solvent such as e.g. MeOH.

When $R_1$ is —$NR^{b'}R^{b'}$, the first conversion may be carried out with an amine of formula $HNR^{b'}R^{b'}$ (VIc) in the presence of a palladium catalyst such as Tris(dibenzylideneacetone) dipalladium(0) ($Pd_2(dba)_3$), an organophosphorus compound, such as e.g. Biphenyl-2-yl-dicyclohexyl-phosphane, (2,2'-bis(diphenylphosphino)-1,1'-binaphthyl) (BINAP), and a base, such as e.g. $Cs_2CO_3$, in a suitable solvent such as dioxane at a suitable temperature preferably heating.

The second conversion from (V) to (III) may be carried out in the presence of a palladium catalyst, such as e.g. Bis(dibenzylideneacetone)palladium(0) ($Pd(dba)_2$) or Tris (dibenzylideneacetone)dipalladium(0) ($Pd_2(dba)_3$), an organophosphorus compound, such as e.g. Biphenyl-2-yl-dicyclohexyl-phosphane, (2,2'-bis(diphenylphosphino)-1,1'-binaphthyl) (BINAP), and a base, such as e.g. $Cs_2CO_3$. The reaction is performed in a suitable solvent, such as e.g. dioxane, at a suitable temperature, preferably heating.

A compound of formula (VII) can be obtained from a compound of formula (X) which is first converted into a compound of formula (IX), which is and subsequently reacted with a compound of formula (VIII) as shown in the scheme below:

Scheme 3

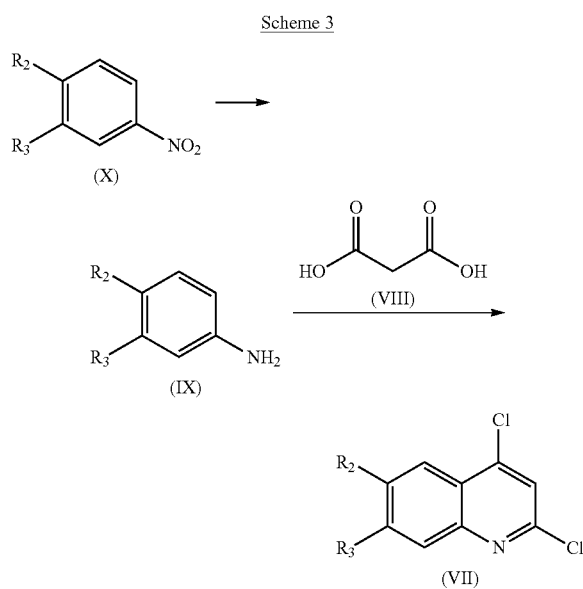

The reduction of the compound of formula (X) may be carried out by hydrogenation, e.g. in the presence of Pd/C in a suitable solvent such as methanol, whereas the conversion of a compound of formula (IX) into a compound of formula (VII) is carried out in the presence of a halogenating agent, such as e.g. POCl$_3$, at a suitable temperature, preferably heating.

A compound of formula (I) which is a compound of formula (Ib) wherein R$_{12}$ and R$_{13}$ are H (i.e. a compound of formula (Ib')), can be obtained from a compound of formula (V) which is reacted with a compound of formula (XII) to give a quinoline of formula (XI), and then subsequently converting the quinoline of formula (XI) into a compound of formula (Ib') as shown in the scheme below:

Scheme 4

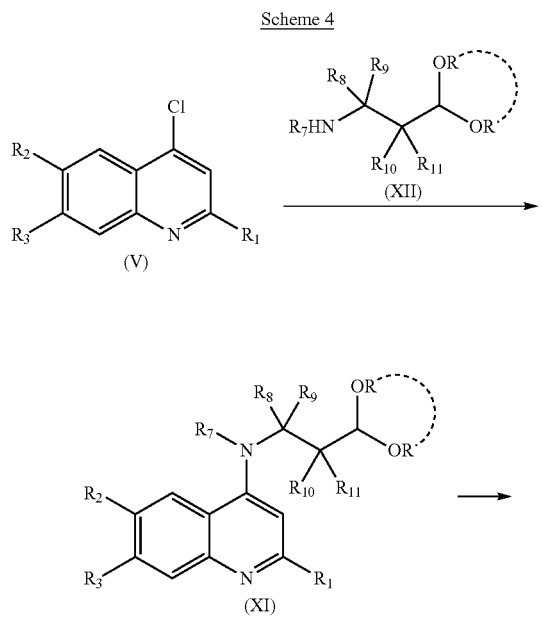

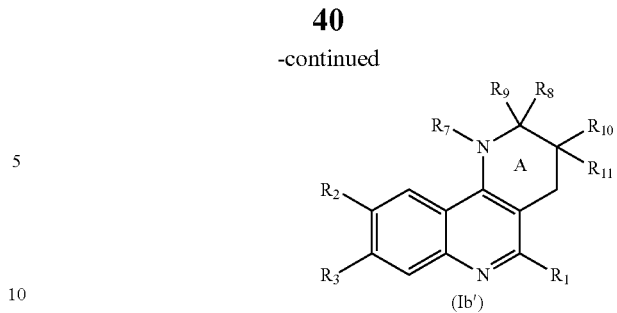

wherein R$_1$-R$_3$, R$_7$ R$_{11}$ are as previously defined, and R is (C$_1$-C$_6$)alkyl or alternatively, the two adjacent groups —OR form a 5- or 6-membered ring together with the atom to which they are attached.

The first conversion may be carried out in the same conditions as the ones described for the conversion of a compound of formula (V) into a compound of formula (III). The second conversion may be carried out in the presence of TiCl$_4$, in the presence of a suitable solvent, such as e.g. dichloromethane (DCM) or dichloroethane, at a suitable temperature, preferably heating, particularly at about 60° C., and then if necessary optionally either hydrogenating the intermediate obtained, e.g. in the presence of Pd/C in a suitable solvent such as methanol, or alternatively hydrogenating the intermediate obtained, and then reacting it with (HCHO)$_n$, (1-ethoxycyclo-propyl)-trimethyl-silane, acetone or cyclohexanone, in the presence of AcOH and a reducing agent such as NaBH$_3$CN, in the presence of a suitable solvent such as methanol, isopropanol or tert-butanol, at a suitable temperature, preferably heating, particularly at about 50-60° C., or alternatively hydrogenating the intermediate obtained, and then reacting it with an acyl chloride such as e.g. acetyl chloride, in the presence of a base such as e.g Et$_3$N (triethylamine), in a suitable solvent such as e.g. dichloromethane (DCM).

Alternatively, a compound of formula (I) which is a compound of formula (Ib) wherein R$_7$ is H (i.e. a compound of formula (Ib'')), can also be obtained from a compound of formula (XIII) which is first converted into a compound of formula (Ib''') and then to a compound of formula (Ib''):

Scheme 5

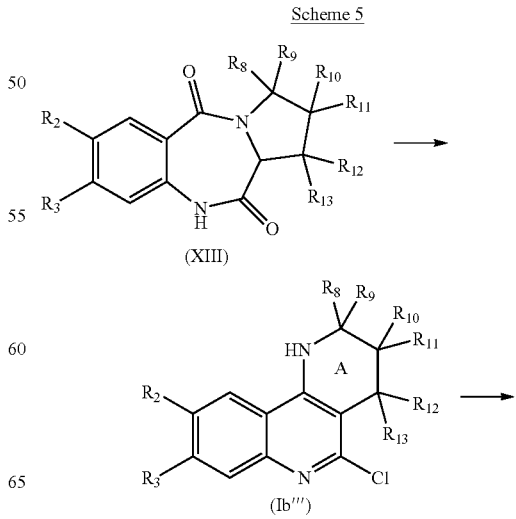

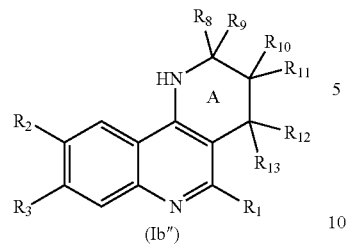

(Ib''')

wherein $R_1$-$R_3$, $R_8$-$R_{13}$ are as previously defined.

The conversion of a compound of formula (XIII) into a compound of formula (Ib''') is carried out in the presence of a halogenating agent, such as e.g. POCl$_3$, optionally in the presence of a catalytic amount of pyridine at a suitable temperature, preferably heating.

When $R_1$ is $R^a$ or $Cy^1$, the conversion of a compound of formula (Ib''') into a compound of formula (Ib'') may be carried out with a boronic derivative of formula $R_1B(OR')_2$ (VIa), wherein $R_1$ is $R^a$ or $Cy^1$, and R' is H, $(C_1$-$C_6)$alkyl or, alternatively, two R' groups together with the B atom to which they are attached may form a cycle, in the same conditions as the ones described for the conversion of a compound of formula (VII) into a compound of formula (V).

When $R_1$ is —$OR^b$, the second conversion may be carried out with an alcohol of formula $R^bOH$ (VIb) in the same conditions described for the conversion of a compound of formula (VII) into a compound of formula (V).

When $R_1$ is —$NR^{b'}R^{b'}$, the second conversion may be carried out with an amine of formula $HNR^{b'}R^{b'}$ (VIc) in the same conditions described for the conversion of a compound of formula (VII) into a compound of formula (V)

A compound of formula (XIII) can be obtained from a compound of formula (XV) which is first converted into a compound of formula (XIV), and then reacting the latter with a compound of formula (XXV) as shown in the scheme below:

Scheme 6

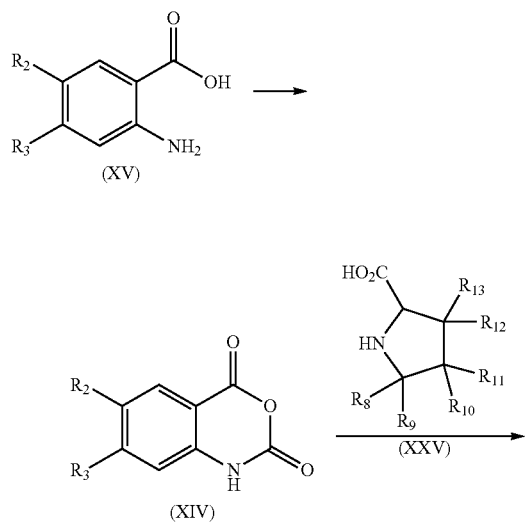

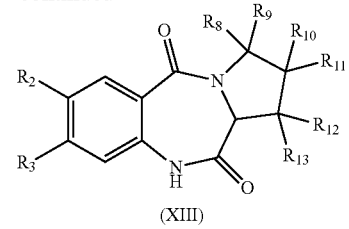

(XIII)

The conversion of a compound of formula (XV) into a compound of formula (XIV) is carried out in the presence of (CCl$_3$CO)$_2$CO at a suitable temperature, preferably heating, whereas the conversion of a compound of formula (XIV) into a compound of formula (XIII) is carried out by reaction with a compound of formula (XXV) in a suitable solvent such as DMF at a suitable temperature, preferably heating.

A compound of formula (I) which is a compound of formula (Ic), wherein $R_{16}$ is H (i.e. a compound of formula (Ic')), can be obtained from a compound of formula (V) which is reacted with a compound of formula (XVII) to give a quinoline of formula (XVI), and then subsequently converting the quinoline of formula (XVI) into a compound of formula (Ic') as shown in the scheme below:

Scheme 7

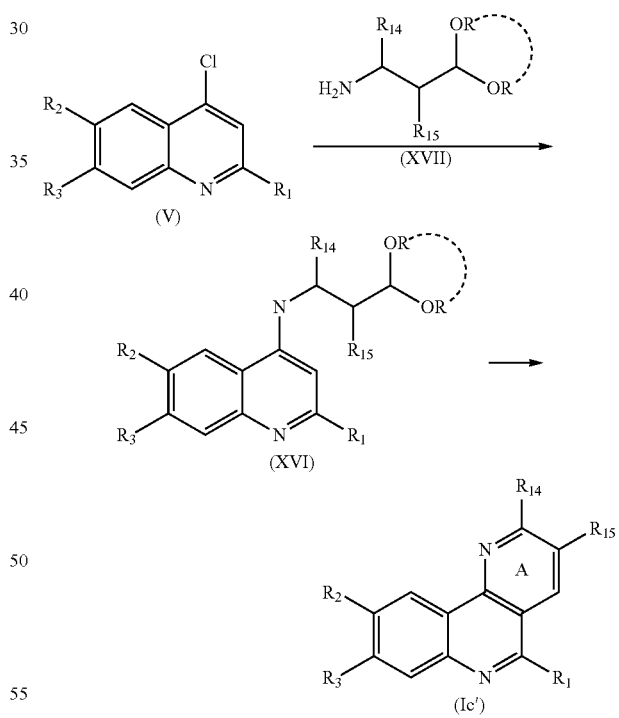

wherein $R_1$-$R_3$, $R_{14}$, and $R_{15}$ are as previously defined, and R is $(C_1$-$C_6)$alkyl, or alternatively, the two adjacent groups —OR form a 5- or 6-membered ring together with the atom to which they are attached.

The first conversion may be carried out in the same conditions as the ones described for the conversion of a compound of formula (V) into a compound of formula (III). The second conversion may be carried out in the presence of TiCl$_4$, in the presence of a suitable solvent, such as e.g. dichloromethane (DCM) or dichloroethane, at a suitable temperature, preferably heating, particularly at about 60° C., and then if necessary optionally reacting the intermediate obtained with (HCHO)$_n$, in the presence of AcOH and a reducing agent such as NaBH$_3$CN, in the presence of a suitable solvent such as methanol, at a suitable temperature, preferably heating, particularly at about 50-60° C.

Further, a compound of formula (I) which is a compound of formula (Id) can be obtained from a compound of formula (XIX) which is converted into a compound of formula (XVIII) that is subsequently converted into a quinoline of formula (Id) as shown in the scheme below:

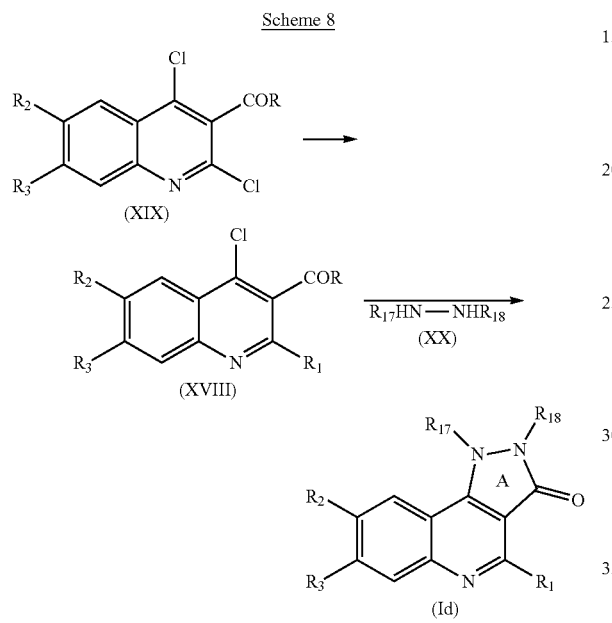

wherein $R_1$-$R_3$, $R_{17}$ and $R_{18}$ are as previously defined and R is (C$_1$-C$_6$)alkyl.

For example, when $R_1$ is $R^a$ or Cy$^1$, the first conversion may be carried out with a boronic derivative of formula $R_1$B(OR')$_2$ (VIa), wherein $R_1$ is $R^a$ or Cy$^1$, and R' is H, (C$_1$-C$_6$)alkyl or, alternatively, two R' groups together with the B atom to which they are attached may form a cycle, in the same conditions as the ones described for the conversion of a compound of formula (VII) into a compound of formula (V).

When $R_1$ is —OR$^b$, the first conversion may be carried out with an alcohol of formula R$^b$OH (VIb) in the same conditions as the ones described for the conversion of a compound of formula (VII) into a compound of formula (V).

When $R_1$ is —NR$^b$R$^{b'}$, the first conversion may be carried out with an amine of formula HNR$^b$R$^{b'}$ (VIc) in the same conditions as the ones described for the conversion of a compound of formula (VII) into a compound of formula (V).

The second conversion may be carried out in the presence of a base such as N,N-diisopropylethylamine (DIEA) in the presence of a suitable solvent such as ethanol and at a suitable temperature, preferably heating. If necessary, after this reaction additional reaction steps may be subsequently performed such as reacting the intermediate obtained a) with tert-butyl 4-methylsulfonyloxy-piperidine-1-carboxylate or tert-butyl 4-(methylsulfonyloxymethyl)piperidine-1-carboxylate, in the presence of a base such as K$_2$CO$_3$ and a suitable solvent, such as dimethylformamide (DMF), at a suitable temperature, preferably heating, b) adding HCl/ EtOAc, and c) adding (HCHO)$_n$, in the presence of AcOH and a reducing agent such as NaBH(OAc)$_3$, in the presence of a solvent such as methanol, and at a suitable temperature, preferably heating.

A compound of formula (XIX) can be obtained from a compound of formula (XXIV) following the route of synthesis as shown in the scheme below:

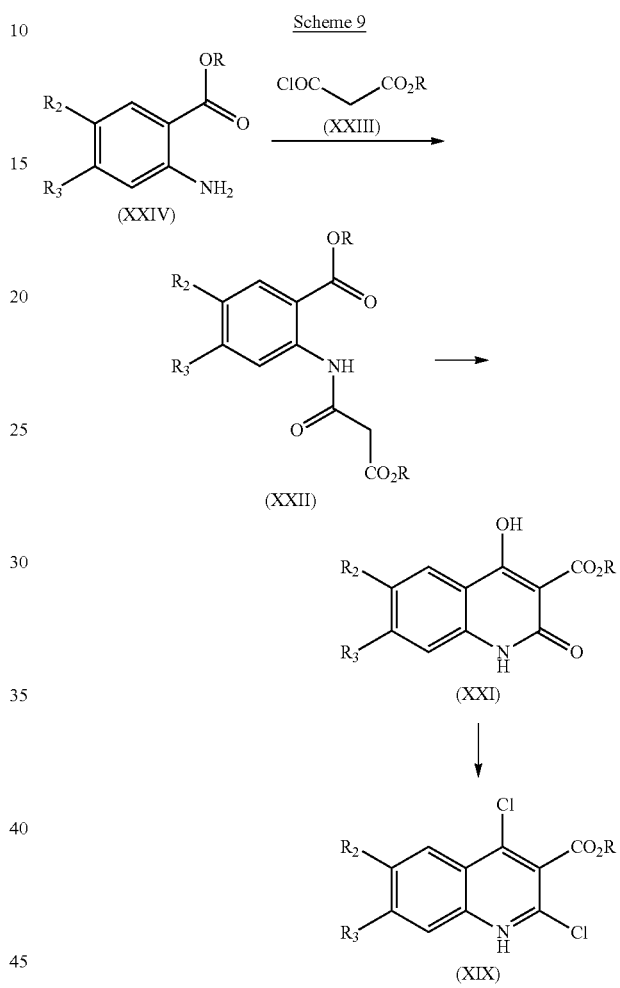

The compound of formula (XXIV) may be reacted with a compound of formula (XXIII) in the presence of a base, such as pyridine and optionally 4-Dimethylaminopyridine (DMAP) in a suitable solvent such as DCM. The compound of formula (XXII) may be converted into a compound of formula XXI in the presence of potassium bis(trimethylsilyl) amide (KHMDS), in a suitable solvent such as tetrahydrofuran, at a suitable temperature. And the compound of formula (XXI) may be converted into a compound of formula (XIX) in the presence of POCl$_3$, and preferably heating.

Alternatively, the reactions described above can be carried out in a different order. Compounds of formula (I) may be converted into other compounds of formula (I). The compounds of formulas (IV), (VI), (VIII), (X), (XII), (XV), (XVII), (XX), (XXIII)-(XV) are commercially available or can be obtained by conventional synthetic processes.

A compound of formula (II) which is a compound of formula (IIa), wherein $R_5'$ is H (i.e., a compound of formula (IIa')), can be obtained from a compound of formula (XXVII):

Scheme 10

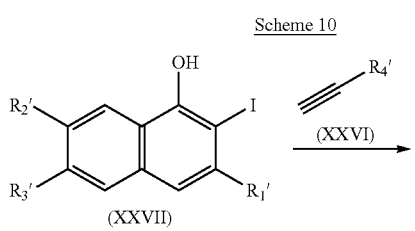

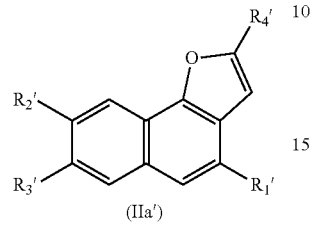

wherein $R_1'$-$R_4'$ are as previously defined.

This conversion may be carried out in the presence of a palladium catalyst, such as e.g. Tetrakis(triphenyl-phosphine)palladium(0) (Pd(PPh$_3$)$_4$) and CuI, in a suitable solvent, such as e.g. acetonitrile optionally mixed with triethylamine, at a suitable temperature, preferably heating.

A compound of formula (XXVII) can be obtained from a compound of formula (XXXI) following the route of synthesis as shown in the scheme below:

Scheme 11

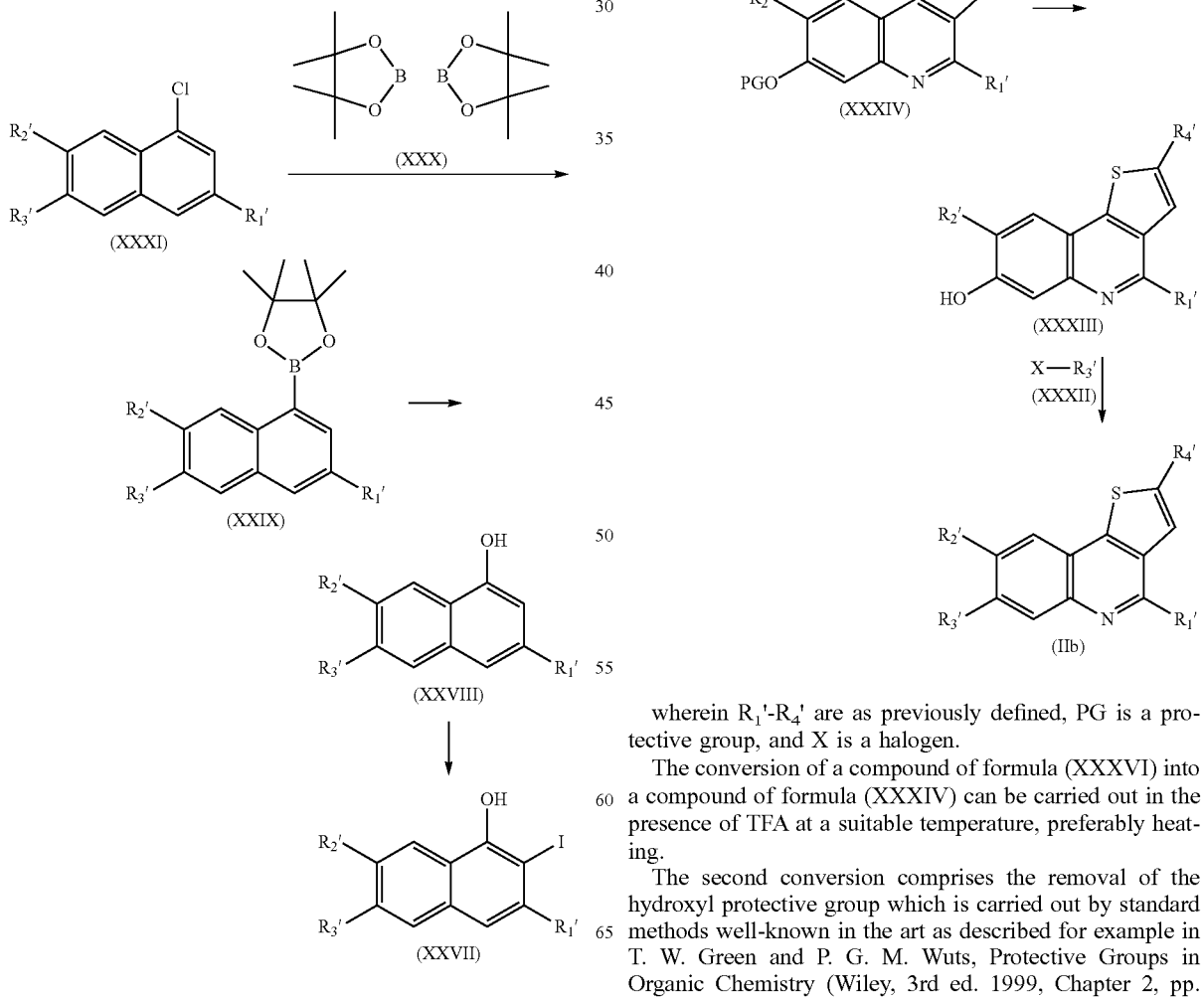

The first conversion can be carried out in the presence of a palladium catalyst base such as [1,1'-Bis(diphenylphosphino)ferrocene]dichloropalladium (Pd(dppf)Cl$_2$) and KOAc in the presence of a suitable solvent such as dioxane and at a suitable temperature, preferably heating. The compound of formula (XXIX) may be converted into a compound of formula (XXVIII) in the presence of H$_2$O$_2$ in a suitable solvent such as dichloromethane (DCM). And the third conversion can be carried out in the presence of KI, and I$_2$ in an aqueous solution of NaOH.

A compound of formula (II) which is a compound of formula (IIb) can be obtained from a compound of formula (XXXVI):

Scheme 12

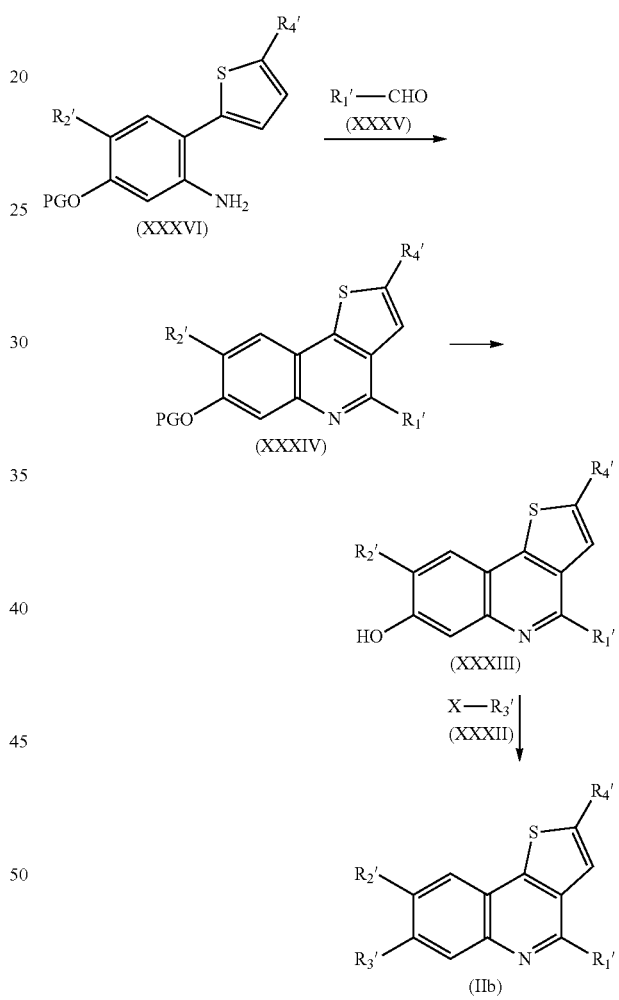

wherein $R_1'$-$R_4'$ are as previously defined, PG is a protective group, and X is a halogen.

The conversion of a compound of formula (XXXVI) into a compound of formula (XXXIV) can be carried out in the presence of TFA at a suitable temperature, preferably heating.

The second conversion comprises the removal of the hydroxyl protective group which is carried out by standard methods well-known in the art as described for example in T. W. Green and P. G. M. Wuts, Protective Groups in Organic Chemistry (Wiley, 3rd ed. 1999, Chapter 2, pp.

17-200). Representative hydroxy protective groups include those where the hydroxy group is either acylated or alkylated such as benzyl, and trityl ethers as well as alkyl ethers, tetrahydropyranyl ethers, trialkylsilyl ethers and allyl ethers. When the hydroxyl protective group is benzyl the deprotection may be carried out by hydrogenation, e.g. in the presence of Pd/C in a suitable solvent such as methanol.

Finally, the third conversion can be carried out with an alkyl halide of formula (XXXII) in the presence of a base such as $Cs_2CO_3$, in a suitable solvent such as DMF and at a suitable temperature, preferably heating.

A compound of formula (XXXVI) can be obtained from a compound of formula (XXXIX) following the route of synthesis as shown in the scheme below:

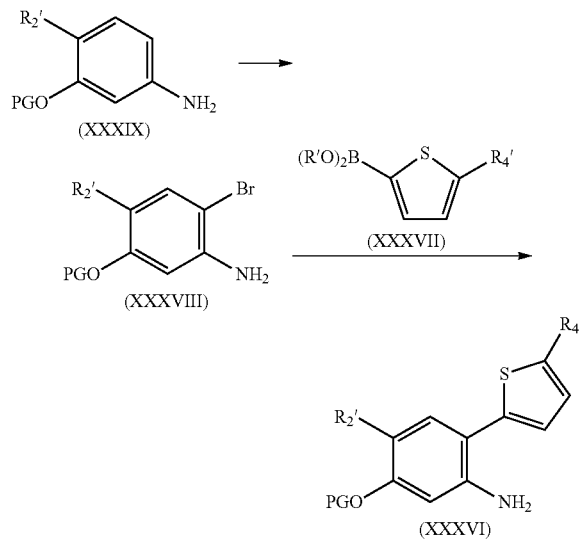

wherein $R_2'$ and $R_4'$ are as previously defined and R' is H, $(C_1-C_6)$alkyl or, alternatively, two R' groups together with the B atom to which they are attached may form a cycle.

The conversion of a compound of formula (XXXIX) into a compound of formula (XXXVIII) may be carried out with a brominating agent such as N-bromosuccinimide (NBS) in a suitable solvent such as acetonitrile, whereas the conversion of a compound of formula (XXXVIII) into a compound of formula (XXXVI) is carried out in the presence of a palladium catalyst, such as e.g. Tetrakis(triphenyl-phosphine)palladium(0) $(Pd(PPh_3)_4)$ and a base, such as e.g. $K_2CO_3$ or $Na_2CO_3$, in a suitable solvent, such as e.g. dioxane optionally mixed with water, at a suitable temperature, preferably heating.

Compounds of formula (I) may be converted into other compounds of formula (I). The compounds of formulas (XXVI), (XXX)-(XXXII), (XXXV), (XXXVII), and (XXXIX) are commercially available or can be obtained by conventional synthetic processes.

The present invention also relates to a pharmaceutical or veterinary composition comprising an effective amount of a compound of formula (I) or formula (II) as defined above, or a pharmaceutically or veterinary acceptable salt thereof, or any stereoisomer either of the compound of formula (I) or formula (II) or of their pharmaceutically or veterinary acceptable salts, together with pharmaceutically or veterinary acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration. For example, a dose of from about 0.01 to about 300 mg/kg may be used.

The expression "pharmaceutically or veterinary acceptable excipients or carriers" refers to pharmaceutically or veterinary acceptable materials, compositions or vehicles. Each component must be pharmaceutically or veterinary acceptable in the sense of being compatible with the other ingredients of the pharmaceutical or veterinary composition. It must also be suitable for use in contact with the tissue or organ of humans and animals without excessive toxicity, irritation, allergic response, immunogenicity or other problems or complications commensurate with a reasonable benefit/risk ratio.

The election of the pharmaceutical or veterinary formulation will depend upon the nature of the active compound and its route of administration. Any route of administration may be used, for example oral, parenteral and topical administration.

For example, the pharmaceutical or veterinary composition may be formulated for oral administration and may contain one or more physiologically compatible carriers or excipients, in solid or liquid form. These preparations may contain conventional ingredients such as binding agents, fillers, lubricants, and acceptable wetting agents.

The pharmaceutical or veterinary composition may be formulated for parenteral administration in combination with conventional injectable liquid carriers, such as water or suitable alcohols. Conventional pharmaceutical or veterinary excipients for injection, such as stabilizing agents, solubilizing agents, and buffers, may be included in such compositions. These pharmaceutical or veterinary compositions may be injected intramuscularly, intraperitoneally, or intravenously.

The pharmaceutical composition may be formulated for topical administration. Formulations include creams, lotions, gels, powders, solutions and patches wherein the compound is dispersed or dissolved in suitable excipients.

The pharmaceutical compositions may be in any form, including, among others, tablets, pellets, capsules, aqueous or oily solutions, suspensions, emulsions, or dry powdered forms suitable for reconstitution with water or other suitable liquid medium before use, for immediate or retarded release.

The appropriate excipients and/or carriers, and their amounts, can readily be determined by those skilled in the art according to the type of formulation being prepared.

As mentioned above, the compounds of the invention having the to 3,4-heterocycloquinoline core and being substituted as previously defined, are inhibitors of DNMTs. For the purposes of the invention, this means that the compounds as defined above are capable of inhibiting one or more DNMTs selected from the group consisting of DNMT1, DNMT3A and DNMT3B, particularly DNMT1, with an $IC_{50}$ value ≤10 μM, preferably ≤1 μM, more preferably ≤500 nM, when the inhibition of DNMTs is measured in enzymatic assays as the ones described in the present invention.

In one embodiment, optionally in combination with one or more features of the various embodiments described above or below, the invention relates to a compound of formula (I) or formula (II) which is additionally inhibitor of G9a. For the purposes of the invention, this means that the compound as defined above is capable of inhibiting G9a with an $IC_{50}$ value ≤10 μM, preferably ≤1 μM, more preferably ≤500 nM, when the inhibition of G9a is measured in enzymatic assays as the ones described in the present invention, and also capable of inhibiting one or more DNMTs as mentioned above.

Thus, the invention relates to a compound of formula (I) or a compound of formula (II) or a pharmaceutical composition comprising the compound of formula (I) or formula (II) as defined above, for use as a medicament.

Moreover, the invention relates to a compound of formula (I) or a compound of formula (II) or a pharmaceutical composition comprising the compound of formula (I) or formula (II) as defined above, for use in the treatment of cancer, fibrosis and/or immunomodulation; in particular cancer, fibrosis and/or immunomodulation mediated by the inhibition of one or more DNMTs selected from the group consisting of DNMT1, DNMT3A and DNMT3B, particularly DNMT1.

Thus, this aspect of the invention relates to the use of a compound of formula (I) or a compound of formula (II) or a pharmaceutical composition comprising the compound of formula (I) or formula (II) as defined above, for the manufacture of a medicament for the treatment and/or prevention of cancer, fibrosis and/or immunomodulation; in particular cancer, fibrosis and/or immunomodulation mediated by the inhibition of one or more DNMTs selected from the group consisting of DNMT1, DNMT3A and DNMT3B, particularly DNMT1.

It may also be formulated as a method for the treatment and/or prevention of cancer, fibrosis and/or immunomodulation; in particular cancer, fibrosis and/or immunomodulation mediated by the inhibition of one or more DNMTs selected from the group consisting of DNMT1, DNMT3A and DNMT3B, particularly DNMT1, comprising administering an effective amount of the previously defined compound of formula (I) or a compound of formula (II) or a pharmaceutical composition comprising the compound of formula (I) or formula (II) as defined above, and one or more pharmaceutically or veterinary acceptable excipients or carriers, in a subject in need thereof, including a human.

In one embodiment, optionally in combination with one or more features of the various embodiments described above or below, cancer, fibrosis and/or immunomodulation are mediated by the dual inhibition of histone methyltransferase G9a and of one or more DNMTs selected from the group consisting of DNMT1, DNMT3A and DNMT3B, particularly DNMT1.

For the purposes of the invention, the term "treatment" of the disease refers to stopping or delaying of the disease progress, when the drug is used in the subject exhibiting symptoms of disease onset. The term "prevention" refers to stopping or delaying of symptoms of disease onset, when the drug is used in the subject exhibiting no symptoms of disease onset but having high risk of disease onset.

In one embodiment, optionally in combination with one or more features of the various embodiments described above or below, the cancer is selected from the group consisting of a hematogical cancer and a solid tumor. More particularly, the hematogical cancer is selected from the group consisting of leukemia including Acute Lymphocytic Leukemia (ALL) and acute myeloid leukemia, lymphoma including Diffuse Large B-cell lymphoma (DLBCL) and mantle cell lymphoma and multiple myeloma; and the solid tumor is selected from the group consisting of bladder cancer, breast cancer, cervical cancer, colorectal cancer, glioblastoma, hepatocarcinoma, lung cancer including small-cell lung cancer, non small-cell lung cancer, melanoma, pancreatic cancer, prostate cancer and renal cancer.

In another embodiment, optionally in combination with one or more features of the various embodiments described above or below, the cancer is selected from the group consisting of Acute Lymphocytic Leukemia (ALL), Diffuse Large B-cell lymphoma (DLBCL), bladder cancer, breast cancer, cervical cancer, colorectal cancer, glioblastoma, hepatocarcinoma, melanoma, pancreatic cancer, prostate cancer, renal cancer, small-cell lung cancer, non small-cell lung cancer, acute myeloid leukemia, mantle cell lymphoma and multiple myeloma.

Throughout the description and claims the word "comprise" and variations of thereof, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

General Procedure for Preparative HPLC Purification Method:

The HPLC measurement was performed using Gilson 281 from 233 pump (binary), an autosampler, and a UV detector. The fractions was detected by LC-MS. The MS detector was configured with an electrospray ionization source. The source temperature was maintained at 300-350° C.

HPLC Methods (Purification Methods):

Method 1:

Reverse phase HPLC was carried out on Luna C18 (100×30 mm; 4 μm). Solvent A: water with 0.075% trifluoroacetic acid; Solvent B: acetonitrile with 0.075% trifluoroacetic acid. Gradient: At room temperature, 20% of B to 40% of B within 6 minutes at 25 mL/min; then 40% B at 25 mL/min over 2 minutes, UV detector.

Method 2:

Reverse phase HPLC was carried out on Luna C18 (100×30 mm; 4 μm). Solvent A: water with 0.075% trifluoroacetic acid; Solvent B: acetonitrile with 0.075% trifluoroacetic acid. Gradient: At room temperature, 25% of B to 45% of B within 6 minutes at 20 mL/min; then 40% B at 25 mL/min over 3 minutes, UV detector.

Method 3:

Reverse phase HPLC was carried out on Luna C18 (100×30 mm; 5 μm). Solvent A: water with 0.1% trifluoroacetic acid; Solvent B: acetonitrile. Gradient: At room temperature, 5% of B to 40% of B within 12 minutes at 20 mL/min; then 100% B at 20 mL/min over 4 minutes, UV detector.

Method 4:

Reverse phase HPLC was carried out on Luna C18 (100×30 mm; 5 μm). Solvent A: water with 0.1% trifluoroacetic acid; Solvent B: acetonitrile. Gradient: At room temperature, 15% of B to 35% of B within 12 minutes at 20 mL/min; then 100% B at 20 mL/min over 3 minutes, UV detector.

Method 5:

Reverse phase HPLC was carried out on Luna C18 (100×30 mm; 5 μm). Solvent A: water with 0.1% trifluoroacetic acid; Solvent B: acetonitrile. Gradient: At room temperature, 7% of B to 40% of B within 12 minutes at 20 mL/min; then 100% B at 20 mL/min over 4 minutes, UV detector.

Method 6:

Reverse phase HPLC was carried out on Luna C18 (100×30 mm; 4 μm). Solvent A: water with 0.075% trifluoroacetic acid; Solvent B: acetonitrile with 0.075% trifluoroacetic acid. Gradient: At room temperature, 20% of B to 45% of B within 6 minutes at 25 mL/min; then 40% B at 25 mL/min over 3 minutes, UV detector.

Method 7:

Reverse phase HPLC was carried out on Luna C18 (100×30 mm; 5 μm). Solvent A: water with 0.1% trifluoroacetic acid; Solvent B: acetonitrile. Gradient: At room temperature, 20% of B to 50% of B within 30 minutes at 80 mL/min; then 100% B at 80 mL/min over 5 minutes, UV detector.

Method 8:

Reverse phase HPLC was carried out on Luna C18 (100×30 mm; 5 μm). Solvent A: water with 0.1% trifluoroacetic acid; Solvent B: acetonitrile. Gradient: At room temperature, 10% of B to 30% of B within 12 minutes at 20 mL/min; then 100% B at 20 mL/min over 3 minutes, UV detector.

Method 9:

Reverse phase HPLC was carried out on Luna C18 (100×30 mm; 4 μm). Solvent A: water with 0.05% hydrochloridric acid; Solvent B: acetonitrile. Gradient: At room temperature, 1% of B to 30% of B within 12 minutes at 20 mL/min; then 100% B at 20 mL/min over 4 minutes, UV detector.

Method 10:

Reverse phase HPLC was carried out on Luna C18 (100×30 mm; 5 μm). Solvent A: water with 0.05% hydrochloridric acid; Solvent B: acetonitrile. Gradient: At room temperature, 1% of B to 30% of B within 12 minutes at 25 mL/min; then 100% B at 25 mL/min over 4 minutes, UV detector.

Method 11:

Reverse phase HPLC was carried out on Luna C18 (100×30 mm; 5 μm). Solvent A: water with 0.1% trifluoroacetic acid; Solvent B: methanol. Gradient: At room temperature, 30% of B to 60% of B within 12 minutes at 25 mL/min; then 100% B at 25 mL/min over 4 minutes, UV detector.

Method 12:

Reverse phase HPLC was carried out on Luna C18 (100×30 mm; 5 μm). Solvent A: water with 0.1% trifluoroacetic acid; Solvent B: acetonitrile. Gradient: At room temperature, 5% of B to 45% of B within 12 minutes at 20 mL/min; then 100% B at 20 mL/min over 2 minutes, UV detector.

Method 13:

Reverse phase HPLC was carried out on Luna C18 (100×30 mm; 5 μm). Solvent A: water with 0.1% trifluoroacetic acid; Solvent B: acetonitrile. Gradient: At room temperature, 30% of B to 55% of B within 12 minutes at 20 mL/min; then 100% B at 20 mL/min over 2 minutes, UV detector.

Method 14:

Reverse phase HPLC was carried out on Luna C18 (100×30 mm; 5 μm). Solvent A: water with 0.1% trifluoroacetic acid; Solvent B: acetonitrile. Gradient: At room temperature, 20% of B to 30% of B within 12 minutes at 20 mL/min; then 100% B at 20 mL/min over 2 minutes, UV detector.

Method 15:

Reverse phase HPLC was carried out on Luna C18 (100×30 mm; 5 μm). Solvent A: water with 0.1% trifluoroacetic acid; Solvent B: acetonitrile. Gradient: At room temperature, 20% of B to 35% of B within 12 minutes at 20 mL/min; then 100% B at 20 mL/min over 5 minutes, UV detector.

Method 16:

Reverse phase HPLC was carried out on Luna C18 (100×30 mm; 5 μm). Solvent A: water with 0.1% trifluoroacetic acid; Solvent B: acetonitrile. Gradient: At room temperature, 10% of B to 30% of B within 12 minutes at 20 mL/min; then 100% B at 20 mL/min over 5 minutes, UV detector.

General Procedure for HPLC Analysis

HPLC-analysis was performed using a Shimadzu LC-20AB or LC-20AD with a Luna-C18(2) column (2.0×50 mm, 5 μm) at 40° C. and UV detection.

Method 1:

Solvent A: water with 0.056% TFA; Solvent B: acetonitrile with 0.056% TFA. Gradient: After 0.01 minutes at the initial condition of 100% A, solvent B was increased to 60% over 4 minutes, maintained at 60% for 0.8 minutes, then a linear gradient to initial conditions was applied for 0.02 minutes and maintained for 0.68 minutes to re-equilibrate the column, giving a cycle time of 5.90 minutes. Flow rate was 0.8 mL/min from 0.01 to 5.21 minutes, increased to 1.2 mL/min in 0.02 minutes and maintained until the end of the run.

Method 2:

Solvent A: water with 0.056% TFA; Solvent B: acetonitrile with 0.056% TFA. Gradient: After 0.1 minutes at the initial condition of 90% A and 10% B, solvent B was increased to 80% over 4 minutes, maintained at 80% for 0.9 minutes, then a linear gradient to initial conditions was applied for 0.02 minutes and maintained for 0.58 minutes to re-equilibrate the column, giving a cycle time of 5.50 minutes. Flow rate was 0.8 mL/min from 0.01 to 4.90 minutes, increased to 1.2 mL/min in 0.03 minutes and maintained until the end of the run.

Method 3:

Solvent A: water with 0.037% TFA; Solvent B: acetonitrile with 0.018% TFA. Gradient: After 0.01 minutes at the initial condition of 90% A and 10% B, solvent B was increased to 80% over 4 minutes, maintained at 80% for 0.9 minutes, then a linear gradient to initial conditions was applied for 0.02 minutes and maintained for 0.58 minutes to re-equilibrate the column, giving a cycle time of 5.50 minutes. Flow rate was 0.8 mL/min from 0.01 to 4.90 minutes, increased to 1.2 mL/min in 0.03 minutes and maintained until the end of the run.

Protocol for SFC Separation Method:

SFC separation was performed using Gilson 281 semi-preparative HPLC system with a chiralcel OD-H column (250×30 mm, 5 μm). Solvent A: n-Hexane; Solvent B: ethanol (0.1% $NH_3.H_2O$). Mobile phase 25% of B and 75% of A at 25 g/min. UV detector at 220 nm. 10 mg per injection.

The following abbreviations have been used in the examples: HPLC: High-performance liquid chromatography; TLC: thin layer chromatography; MW: microwaves; calc.: calculated; conc.: concentrated; rt: room temperature; Rt: Retention time; Boc: tert-butoxycarbonyl; DMAP: 4-Dimethylaminopyridine; DCM: dichloromethane; DIAD:

Diisopropyl azodicarboxylate; DMF: dimethylformamide; DMSO: dimethylsulfoxide; eq: equivalent; ESI-MS: electrospray ionization mass spectrometry; Et$_3$N: triethylamine; TFA: trifluoroacetic acid; THF: tetrahydrofuran; DEAD: diethylazodicarboxylate; BINAP: 2,2'bis(diphenylphospinio)-1,1'-binaphthyl; EtOAc: ethyl acetate; EtOH: ethanol; MeOH: methanol; MTBE: Methyl tert-butyl ether; Ph: phenyl; AcOH: acetic acid.

Preparation of Reagent R-03b: tert-butyl 4-(2-amino-3,3-diethoxy-propyl)piperidine-1-carboxylate A mixture of tert-butyl 4-formylpiperidine-1-carboxylate (7.46 g, 35.00 mmol) and 1,1-diethoxy-2-nitro-ethane (4.97 g, 30.43 mmol) in TEA (3.70 g, 36.52 mmol) was stirred at 18° C. for 8 hours. Then a solution of DMAP (372 mg, 3.03 mmol) in Ac$_2$O (4.66 g, 45.65 mmol) was added and the resulting mixture was stirred at 18° C. for 7 hours. The reaction was quenched with water and then extracted with EtOAc. The combined organic phase was washed with saturated brine, dried with anhydrous Na$_2$SO$_4$, filtered and concentrated in vacuum. The residue was purified by column chromatography to give intermediate tert-butyl 4-[(E)-3,3-diethoxy-2-nitro-prop-1-enyl]piperidine-1-carboxylate (4.68 g, 43%) as a yellow liquid. A stirred suspension of this intermediate (3.00 g, 8.37 mmol) in absolute EtOH (80 mL) and CHCl$_3$ (6 mL) containing PtO$_2$ (475.2 mg, 2.09 mmol) was placed under H$_2$ (50 Psi) at 15° C. After stirring for 40 hours, the mixture was filtered through Celite and washed with EtOH. The filtrate was concentrated to dryness to give the desired tert-butyl 4-(2-amino-3,3-diethoxy-propyl)piperidine-1-carboxylate (3.35 g, 99% crude) as a yellow syrup which was used for next step without further purification. ESI-MS (M+1): 331.3 calc. for C$_{17}$H$_{34}$N$_2$O$_4$: 330.3.

Preparation of Reagent R-04b: tert-butyl 4-[2-amino-3-(1,3-dioxolan-2-yl)propyl]piperidine-1-carboxylate To a solution of commercially available 2-(2-bromoethyl)-1,3-dioxolane (40.73 g, 225 mmol) in anhydrous DMSO (350 mL) was added a solution of NaNO$_2$ (27.95 g, 405 mmol) in anhydrous DMSO (350 mL) slowly at 0° C. and the resulting mixture was stirred at 18° C. for 6 hours under N$_2$. Then, the reaction mixture was poured into water and extracted with MTBE. The combined organic phase was washed with brine, dried with anhydrous Na$_2$SO$_4$, filtered and concentrated in vacuum. The crude product was purified by silica gel column chromatography to give intermediate 2-(2-nitroethyl)-1,3-dioxolane (12.50 g, 38%) as a yellow liquid. A mixture of this intermediate (3.97 g, 27 mmol) and tert-butyl 4-formylpiperidine-1-carboxylate (6.61 g, 31) in TEA (3.00 g, 30 mmol) was stirred at 18° C. for 8 hours. Then a solution of DMAP (330 mg, 2.70 mmol) in Ac$_2$O (4.13 g, 40 mmol) was added and the reaction mixture was stirred at 18° C. for 7 hours. The reaction was quenched with water and then extracted with EtOAc. The combined organic phase was washed with saturated brine, dried with anhydrous Na$_2$SO$_4$, filtered and concentrated in vacuum. The residue was purified by silica gel column chromatography to afford intermediate tert-butyl 4-[(Z)-3-(1,3-dioxolan-2-yl)-2-nitro-prop-1-enyl]piperidine-1-carboxylate (5.64 g, 61%) as a yellow liquid. Finally, a stirred suspension of this intermediate (2.50 g, 7.30 mmol) in absolute EtOH (100 mL) and CHCl$_3$ (8 mL) containing PtO$_2$ (414 mg, 1.83 mmol) was placed under H$_2$ (50 Psi) at 18° C. After 15 hours, the mixture was filtered through Celite and washed with EtOH. The filtrate was concentrated to dryness to give desired reagent R-04b (2.02 g, 88% crude) as a yellow syrup which was used for next step without further purification. ESI-MS (M+1): 315.3 calc. for C$_{16}$H$_{30}$N$_2$O$_4$: 314.2.

Preparation of Reagent tert-butyl 4-methylsulfonyloxypiperidine-1-carboxylate

To a mixture of commercially available tert-butyl 4-hydroxypiperidine-1-carboxylate (1.00 g, 4.97 mmol) and MsCl (854 mg, 7.46 mmol) in DCM (20 mL) was added Et$_3$N (1.01 g, 9.94 mmol) in one portion at 0° C. under N$_2$. The mixture was stirred at 25° C. for 2 hours. Then, the mixture was poured into ice-water (w/w=1/1) and extracted with DCM. The combined organic phase was washed with saturated brine, dried with anhydrous Na$_2$SO$_4$, filtered and concentrated under vacuum to afford tert-butyl 4-methylsulfonyloxypiperidine-1-carboxylate (1.30 g, 94%) as a white solid. $^1$H NMR (400 MHz, CDCl$_3$): δ (ppm) 4.91-4.85 (m, 1H), 3.70-3.68 (m, 2H), 3.33-3.27 (m, 2H), 3.04 (s, 3H), 1.97-1.94 (m, 2H), 1.83-1.80 (m, 2H), 1.46 (s, 9H).

Preparation of Reagent tert-butyl 4-(methylsulfonyloxymethyl)piperidine-1-carboxylate To a mixture of commercially available tert-butyl 4-(hydroxymethyl)piperidine-1-carboxylate (1.00 g, 4.64 mmol) and MsCl (797 mg, 6.96 mmol) in DCM (30 mL) was added Et$_3$N (939 mg, 9.28 mmol) in one portion at 0° C. under N$_2$ and the mixture was stirred at 25° C. for 2 hours. Then, the solution was extracted with DCM. The combined organic phase was washed with saturated brine, dried with anhydrous Na$_2$SO$_4$, filtered and concentrated in vacuum to afford tert-butyl 4-(methylsulfonyloxymethyl)piperidine-1-carboxylate (1.30 g, 95%) as a white solid. $^1$H NMR (400 MHz, CDCl$_3$): δ (ppm) 4.12 (br s, 2H), 4.08-4.04 (m, 2H), 2.99 (s, 3H), 2.72-2.66 (m, 2H), 1.91-1.88 (m, 1H), 1.73-1.70 (m, 2H), 1.43 (s, 9H), 1.23-1.17 (m, 2H).

Synthetic Route 1

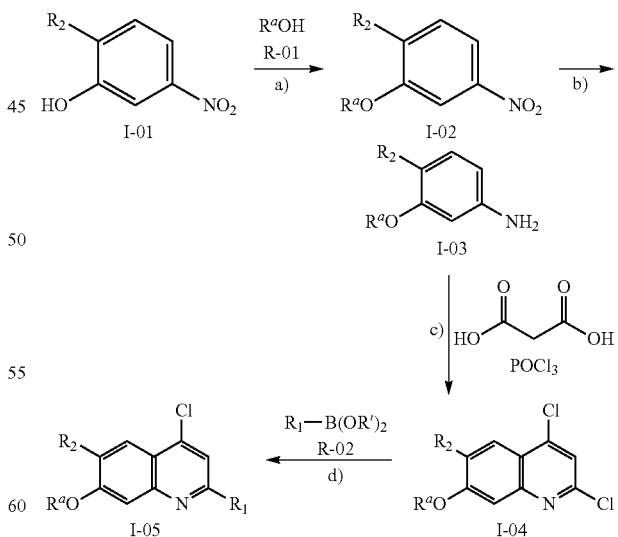

Conditions: a) PPh$_3$ (2.0 eq), 3-pyrrolidin-1-yl-propan-1-ol (R-01a, 1.0 eq), DEAD (2.0 eq), THF, 0° C., then rt, 5 h; b) Pd/C, MeOH, H$_2$, rt, 3 h; c) POCl$_3$, malonic acid (1.1 eq), rt, 4 h, then 90° C., overnight; d) Pd(PPh$_3$)$_4$ (0.1-0.3 eq), Na$_2$CO$_3$ or K$_2$CO$_3$ (2.0-3.0 eq), R-02 (1.0-1.1 eq), 1,4-dioxane/H$_2$O (15:1 or 10:1), 110° C., MW, 4 h or 80° C. conventional heating, 12 h.

In the scheme above $R_2$ is H or $O(C_1-C_6)$alkyl, $R^a$ is a hydrocarbon chain which contains nitrogen and/or oxygen atoms, $R_1$ is aryl or heteroaryl and R' is H, $(C_1-C_6)$alkyl or, alternatively, two R' groups together with the B atom to which they are attached may form a cycle.

Preparation of Intermediate I-02a: 1-[3-(2-methoxy-5-nitro-phenoxy)propyl]-pyrrolidine To a solution of commercially available 2-methoxy-5-nitro-phenol (1-01a, 19.6 g, 0.12 mol) in THF (200 mL), $PPh_3$ (61 g, 0.23 mol), commercially available 3-pyrrolidin-1-yl-propan-1-ol (R-01a, 15 g, 0.12 mol) and DEAD (40 g. 0.23 mol) were added at 0° C., the solution was stirred at room temperature for 5 hours. The reaction mixture was concentrated and extracted with AcOEt. The combined organic layers were washed with brine, dried over anhydrous $Na_2SO_4$, filtered and concentrated to give the crude product which was purified by column chromatography to give intermediate I-02a (14 g, 44%) as a yellow solid. ESI-MS (M+1): 281 calc. for $C_{14}H_{20}N_2O_4$: 280.1.

Preparation of Intermediate I-02b: 1-[3-(3-nitrophenoxy)propyl]pyrrolidine

Intermediate I-02b was obtained in an analogous manner to intermediate I-02a starting from commercially available 3-nitrophenol (I-01b). The crude product was purified by column chromatography to obtain intermediate I-02b as a yellow solid (37% yield). ESI-MS (M+1): 251 calc. for $C_{13}H_{18}N_2O_3$: 250.1.

Preparation of Intermediate I-03a: 4-methoxy-3-(3-pyrrolidin-1-ylpropoxy)aniline To a solution of intermediate I-02a (14 g, 0.05 mol) in MeOH (200 mL) was added Pd/C (3 g). The solution was stirred at room temperature for 3 hours in $H_2$ atmosphere. Then, the solution was filtrated and concentrated to give intermediate I-03a (12 g, 96%) as a yellow oil. ESI-MS (M+1): 251 calc. for $C_{14}H_{22}N_2O_2$: 250.1.

Preparation of Intermediate I-03b: 3-(3-pyrrolidin-1-ylpropoxy)aniline

Intermediate I-03b was obtained in an analogous manner to intermediate I-03a starting from intermediate I-02b (96% yield). ESI-MS (M+1): 221 calc. for $C_{13}H_{20}N_2O$: 220.1.

Preparation of Intermediate I-04a: 2,4-dichloro-6-methoxy-7-(3-pyrrolidin-1-ylpropoxy)quinoline To a solution of intermediate I-03a (12.4 g, 0.049 mol) in $POCl_3$ (200 mL) was added malonic acid (5.67, 0.055 mol) at room temperature. After stirring at room temperature for 4 hours, the solution was heated at 90° C. overnight. Then, the solution was concentrated and poured into ice-water and extracted with EtOAc. The combined organic layers were washed with brine, dried over anhydrous $Na_2SO_4$, filtered and concentrated to give intermediate I-04a (10 g, 58%) as a pale yellow solid. ESI-MS (M+1): 355 calc. for $C_{17}H_{20}Cl_2N_2O_2$: 354.1.

Preparation of Intermediate I-04b: 2,4-dichloro-7-(3-pyrrolidin-1-ylpropoxy)quinoline Intermediate I-04b was obtained in an analogous manner to intermediate I-04a starting from intermediate I-03b (34% yield). ESI-MS (M+1): 325 calc. for $C_{16}H_{18}Cl_2N_2O$. 324.1.

Preparation of Intermediate I-05a: 4-chloro-6-methoxy-2-(5-methyl-2-furyl)-7-(3-pyrrolidin-1-ylpropoxy)quinoline To a solution of intermediate I-04a (600 mg, 1.7 mmol) in 1,4-dioxane/$H_2O$ (15:1, 16 mL) were added $Na_2CO_3$ (0.54 g, 5.1 mmol), $Pd(PPh_3)_4$ (0.22 g, 0.17 mmol) and 4,4,5,5-tetramethyl-2-(5-methyl-2-furyl)-1,3,2-dioxaborolane (R-02a, 0.39 g, 1.87 mmol). The solution was stirred at 110° C. for 4 hours under Microwave. Then, the mixture was quenched with water and extracted with EtOAc. The combined organic phase was washed with brine, dried over anhydrous $Na_2SO_4$ and concentrated to give the crude product which was purified by prep-HPLC (General procedure, Method 1) to give intermediate I-05a (400 mg, 59%) as a yellow solid. ESI-MS (M+1): 401.2 calc. for $C_{22}H_{25}ClN_2O_3$: 400.1.

Preparation of Intermediate I-05b: 4-chloro-2-(5-methyl-2-furyl)-7-(3-pyrrolidin-1-ylpropoxy)quinoline Intermediate I-05b was obtained in an analogous manner to intermediate I-05a starting from intermediate I-04b. The crude product was purified by prep-TLC to obtain intermediate I-05b as a yellow solid (88% yield). ESI-MS (M+1): 371 calc. $C_{21}H_{23}ClN_2O_2$: 370.1.

Preparation of Compound I-05c: 4-chloro-2-(5-ethyl-2-furyl)-6-methoxy-7-(3-pyrrolidin-1-ylpropoxy)quinoline Intermediate I-05c was obtained in an analogous manner to intermediate I-05a using reagent 2-(5-ethyl-2-furyl)-4,4,5,5-tetramethyl-1,3,2-dioxaborolane (R-02b). The crude product was purified by column chromatography to obtain intermediate I-05c as a brown oil (85% yield). ESI-MS (M+1): 414.3 calc for $C_{23}H_{27}ClN_2O_3$: 414.2.

Preparation of Intermediate I-05d: 4-chloro-6-methoxy-2-phenyl-7-(3-pyrrolidin-1-ylpropoxy)quinoline A mixture of phenylboronic acid (R-02c, 539 mg, 4.42 mmol), intermediate I-04a (1.56 g, 4.42 mmol), $K_2CO_3$ (1.22 g, 8.84 mmol) and $Pd(PPh_3)_4$ (1.53 g, 1.33 mmol) in $H_2O$/1,4-dioxane (1:10, 11 mL) was degassed and purged with $N_2$ for 3 times. Then, the mixture was stirred at 80° C. for 12 hours under $N_2$ atmosphere. The reaction mixture was concentrated under vacuum to give the crude product which was purified by column chromatography to afford intermediate I-05d (1.00 g, 57%) as a yellow solid. ESI-MS (M+1): 397.2 calc for $C_{23}H_{25}ClN_2O_2$: 396.1.

Preparation of Intermediate I-05e: 4-chloro-2-(2,5-dimethyl-3-furyl)-6-methoxy-7-(3-pyrrolidin-1-yl-propoxy)quinoline A mixture of intermediate I-04a (500 mg, 1.41 mmol), 2-(2,5-dimethyl-3-furyl)-4,4,5,5-tetramethyl-1,3,2-dioxaborolane (R-02d, 313 mg, 1.41 mmol), $Pd(PPh_3)_4$ (163 mg, 141.00 μmol) and $K_2CO_3$ (390 mg, 2.82 mmol) in dioxane (20 mL)/$H_2O$ (2 mL) was degassed and purged with $N_2$ for 3 times. Then, the mixture was stirred at 110° C. for 16 hours under $N_2$ atmosphere. The mixture was cooled to 20° C. and concentrated in reduced pressure at 40° C. The residue was poured into water (100 mL) and extracted with ethyl acetate (100 mL×3). The combined organic phase was washed with brine (100 mL×2), dried with anhydrous Na$_2$SO$_4$, filtered and concentrated in vacuum. The residue was purified by column chromatography (SiO$_2$, Petroleum ether/Ethyl acetate=50/1 to 1:1, DCM/MeOH=50/1 to 1:1) to give 1-05e (400 mg, 68% yield) as a yellow solid. ESI-MS (M+1): 415.2 calc for C$_{23}$H$_{27}$ClN$_2$O$_3$: 414.2.

Synthetic Route 2

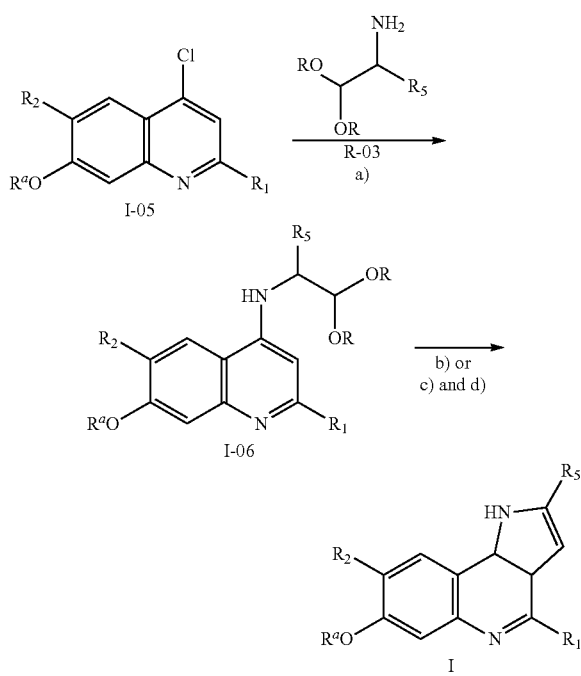

Conditions: a) R-03 (5-0-8.0 eq), Cs$_2$CO$_3$ (2.0-2.5 eq), BINAP (0.1-0.4 eq), Pd(dba)$_2$ or Pd$_2$(dba)$_3$ (01.-0.2 eq), 1,4-dioxane, 110-130° C., 12-40 h; b) BF$_3$•Et$_2$O (1.0 eq), DCM, 0° C., 1 h; c) TiCl$_4$ (2.5 eq), ClCH$_2$CH$_2$Cl, 60° C., 6-10 h; d) (HCHO)$_n$ or acetone (2-8.0 eq), AcOH (8.0-10 eq) or HCOOH (0.2 eq), NaBH$_3$CN (2-8.0 eq), MeOH or i-PrOH, 50-60° C., 6-10 h.

In the scheme above, R$_2$ is H or O(C$_1$-C$_6$)alkyl, R$^a$ is a hydrocarbon chain which contains nitrogen and/or oxygen atoms, R$_1$ is aryl or heteroaryl, R$_5$ is H, a cycle (Cy) or a hydrocarbon chain which optionally contains nitrogen oxygen and/or fluor atoms, and R is (C$_1$-C$_6$)alkyl, or alternatively, the two adjacent groups —OR form a 5- or 6-membered ring together with the atom to which they are attached.

Preparation of Intermediate I-06a: N-(2,2-dimethoxyethyl)-6-methoxy-2-(5-methyl-2-furyl)-7-(3-pyrrolidin-1-ylpropoxy)quinolin-4-amine To a mixture of intermediate I-05a (250 mg, 623 μmol) and 2,2-dimethoxyethanamine (R-03a, 328 mg, 3.12 mmol) in 1,4-dioxane (20 mL), was added Cs$_2$CO$_3$ (406 mg, 1.25 mmol), Pd(dba)$_2$ (36 mg, 62 μmol) and BINAP (39 mg, 62 μmol) in one portion at 25° C. under N$_2$. The mixture was stirred at 25° C. for 10 minutes and then, heated to 110° C. and stirred for 12 hours. The mixture was concentrated in vacuum and the residue was purified by prep-TLC to afford intermediate I-06a (100 mg, 34%) as yellow solid. ESI-MS (M+1): 470.3 calc. for C$_{26}$H$_{35}$N$_3$O$_5$: 469.2.

Preparation of Compound 1-01: 8-methoxy-4-(5-methyl-2-furyl)-7-(3-pyrrolidin-1-ylpropoxy)-1H-pyrrolo[3,2-c]quinoline To a mixture of intermediate I-06a (40 mg, 85 μmol) in DCM (2 mL), was added BF$_3$.Et$_2$O (12 mg, 85 μmol) in one portion at 0° C. under N$_2$ and the mixture was stirred at 0° C. for 1 hour. Then, mixture was purified by prep-HPLC (General procedure, Method 2) to afford compound 1-01 (5.00 mg 15%) as yellow solid. ESI-MS (M+1): 406.2 calc. for C$_{24}$H$_{27}$N$_3$O$_3$: 405.2.

Preparation of Intermediate I-06b: tert-butyl 4-[3,3-diethoxy-2-[[6-methoxy-2-(5-methyl-2-furyl)-7-(3-pyrrolidin-1-ylpropoxy)-4-quinoyl]amino]propyl] piperidine-1-carboxylate To a solution of intermediate I-05a (400 mg, 997 μmol) and tert-butyl 4-(2-amino-3,3-diethoxy-propyl)piperidine-1-carboxylate (R-03b, 2.64 g, 7.98 mmol) in 1,4-dioxane (60 mL) were successively added Pd$_2$(dba)$_3$ (182 mg, 199 μmol), Cs$_2$CO$_3$ (812 mg, 2.49 mmol) and BINAP (248 mg, 399 μmol). The resulting mixture was stirred at 130° C. for 40 hours under N$_2$. Then, the mixture was diluted with water, and extracted with EtOAc. The combined organic layer was washed with brine, dried by Na$_2$SO$_4$, filtered and concentrated to give crude product which was purified by column chromatography to give intermediate I-06b (450 mg, 65%) as a yellow solid. ESI-MS (M+1): 695.5 calc. for C$_{39}$H$_{58}$N$_4$O$_7$: 694.4.

Preparation of Compound 1-02: 8-methoxy-4-(5-methyl-2-furyl)-2-[(1-methyl-4-piperidyl)methyl]-7-(3-pyrrolidin-1-ylpropoxy)-1H-pyrrolo[3,2-c]quinoline To a solution of intermediate I-06b (440 mg, 633 μmol) in ClCH$_2$CH$_2$Cl (50 mL) was added TiCl$_4$ (300 mg, 1.58 mmol) slowly. The resulting mixture was stirred at 60° C. for 10 hours under N$_2$. Then, the reaction was quenched by adding NH$_3$.H$_2$O (8 mL, 25%) and Na$_2$SO$_4$ (9.0 g) and the resulting mixture was stirred at 15° C. for 1 hour. The solution was filtered and concentrated to afford the desired intermediate 8-methoxy-4-(5-methyl-2-furyl)-2-(4-piperidylmethyl)-7-(3-pyrrolidin-1-ylpropoxy)-1H-pyrrolo[3,2-c]quinoline (175 mg, 55%) as a yellow solid. To a mixture of this intermediate (170 mg, 338 μmol) and (HCHO)$_n$ (243 mg, 2.7 mmol) in MeOH (40 mL) were added AcOH (162 mg, 2.7 mmol) and NaBH$_3$CN (170 mg, 2.7 mmol) in one portion at 16° C. under N$_2$. Then, the mixture was stirred at 50° C. for 10 hours. The mixture was cooled to 16° C., filtered and concentrated in vacuum. The residue was purified by prep-HPLC (General procedure, Method 1) to afford the desired compound 1-02 (14.3 mg, 8.2%) as a yellow solid. ESI-MS (M+1): 517.4 calc. for C$_{31}$H$_{40}$N$_4$O$_3$: 516.3. HPLC analytical method 1, Rt=2.85 min.

Preparation of Compound 1-03: 2-[(1-isopropyl-4-piperidyl)methyl]-8-methoxy-4-(5-methyl-2-furyl)-7-(3-pyrrolidin-1-ylpropoxy)-1H-pyrrolo[3,2-c]quinoline To a solution of intermediate I-06b (440 mg, 633 μmol) in ClCH$_2$CH$_2$Cl (50 mL) was added TiCl$_4$ (300 mg, 1.58 mmol) slowly. The resulting mixture was stirred at 60° C. for 10 hours under N$_2$. Then, the reaction was quenched by adding NH$_3$.H$_2$O (8 mL, 25%) and Na$_2$SO$_4$ (9.0 g) and the resulting mixture was stirred at 15° C. for 1 hour. The solution was filtered and concentrated to afford the desired intermediate 8-methoxy-4-(5-methyl-2-furyl)-2-(4-piperidylmethyl)-7-(3-pyrrolidin-1-ylpropoxy)-1H-pyrrolo[3,2-c]quinoline (175 mg, 55%) as a yellow solid. To a mixture of this intermediate (24 mg, 48 μmol), acetone (15.3 mg, 262

µmol), CH$_3$COOH (262 ug, 4.38 µmol) and NaBH$_3$CN (16.5 mg, 262 µmol) in i-PrOH (5 mL) was degassed and purged with N$_2$ for 3 times. Then, the mixture was stirred at 60° C. for 6 hours under N$_2$ atmosphere. The reaction mixture was concentrated under vacuum to give the crude product which was purified by prep-HPLC (General procedure, Method 3) to obtain compound 1-03 (12.2 mg, 47%) as a yellow gum. ESI-MS (M+1): 545.4 calc. for C$_{33}$H$_{44}$N$_4$O$_3$: 544.3. HPLC analytical method 2, Rt=1.48 min.

Following the same synthetic route for compound 1-02 and using the same reagents unless otherwise indicated in the table below, the following compounds were obtained:

| Example | Prep-HPLC Method | [M + 1]$^+$ | Intermediate/reagent |
|---|---|---|---|
| 1-04 | 4 | 531.4 | I-05c/tert-butyl 4-(2-amino-3,3-diethoxy-propyl)piperidine-1-carboxylate (R-03b) |
| 1-05 | 5 | 513.4 | I-05d/tert-butyl 4-(2-amino-3,3-diethoxy-propyl)piperidine-1-carboxylate (R-03b) |
| 1-06 | 12 | 531.4 | I-05e/tert-butyl 4-(2-amino-3,3-diethoxy-propyl)piperidine-1-carboxylate (R-03b) |

Synthetic Route 3

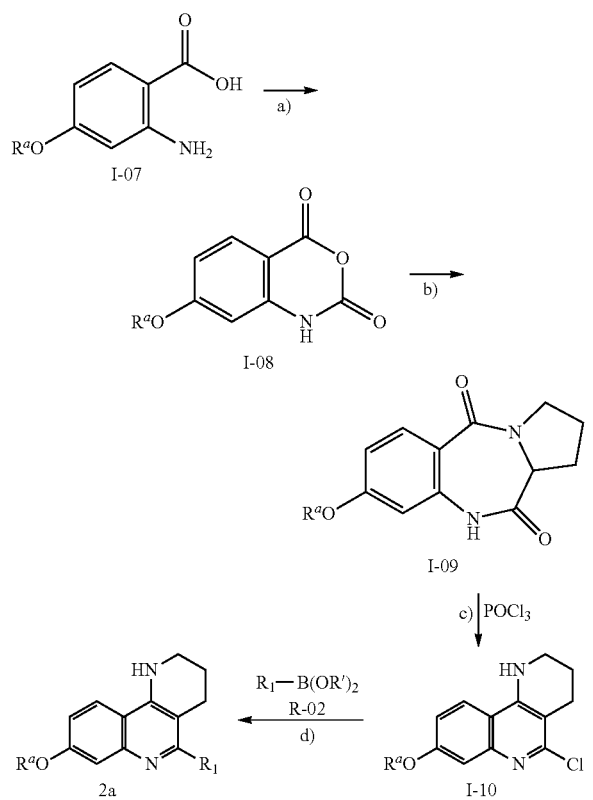

Conditions: a) (CCl$_3$CO)$_2$CO (0.67 eq), 80° C., 4 h; b) pyrrolidine-2-carboxylic acid (2.0 eq), DMF, 140° C., 6 h; c) POCl$_3$, pyridine (cat), 120° C., 12 h; d) R-02 (1.0 eq), Na$_2$CO$_3$ (2.0 eq), Pd(PPh$_3$)$_4$ (cat), 1,4-dioxane/H$_2$O (15:1), 110° C., MW, 4 h.

In the scheme above R$^a$ is a hydrocarbon chain which contains nitrogen and/or oxygen atoms, R$_1$ is aryl or heteroaryl, and R' is H, (C$_1$-C$_6$)alkyl or, alternatively, two R' groups together with the B atom to which they are attached may form a cycle.

Preparation of Intermediate I-08a: 7-methoxy-1H-3,1-benzoxazine-2,4-dione

To a solution of commercially available 2-amino-4-methoxy-benzoic acid (I-07a, 1.67 g, 10 mmol) in THF (50 mL) was added (CCl$_3$CO)$_2$CO (1.99 g, 6.7 mmol) slowly and the solution was heated to 80° C. for 4 hours. Then, the solution was concentrated and extracted with EtOAc. The combined organic layer was washed with brine, dried over anhydrous Na$_2$SO$_4$ and concentrated to give the crude product which was purified by prep-HPLC (General procedure, Method 6) to give intermediate I-08a (1.7 g, 88%) as yellow solid. ESI-MS (M+1): 194 calc. for C$_9$H$_7$NO$_4$: 193.0.

Preparation of Intermediate I-09a: 3-methoxy-6a,7,8,9-tetrahydro-5H-pyrrolo[2,1-c][1,4]benzodiazepine-6,11-dione To a solution of intermediate I-08a (1.94 g, 10 mmol) in DMF (50 mL) was added pyrrolidine-2-carboxylic acid (2.30 g, 20 mmol) slowly and the solution was heated to 140° C. for 6 hours. Then, the solution was concentrated and extracted with EtOAc. The combined organic layer was washed with brine, dried over anhydrous Na$_2$SO$_4$ and concentrated to give intermediate I-09a (1.5 g, 61%) as white solid which was used in the next step without further purification.

Preparation of Intermediate I-10a: 5-chloro-8-methoxy-1,2,3,4-tetrahydrobenzo[h][1,6]naphthyridine To a solution of intermediate I-09a (246 mg, 1 mmol) in POCl$_3$ (20 mL) was added pyridine (1 mL, catalyst) and the solution was heated to 120° C. for 12 hours. Then, the solution was quenched with water and extracted with EtOAc. The combined organic layer was washed with brine, dried over anhydrous Na$_2$SO$_4$ and concentrated to give the crude product which was purified by prep-HPLC (General Procedure, Method 6) to give intermediate I-10a (150 mg, 61%) as white solid. ESI-MS (M+1): 249.1 calc. for C$_{13}$H$_{13}$ClN$_2$O: 248.1.

Preparation of Compound 2-01: 8-methoxy-5-(5-methyl-2-furyl)-1,2,3,4-tetrahydrobenzo[h][1,6] naphthyridine To a solution of intermediate I-10a (124 mg, 0.5 mmol) in 1,4-dioxane/H$_2$O (15:1, 16 mL) was added Na$_2$CO$_3$ (106 mg, 1 mmol), Pd(PPh$_3$)$_4$ (20 mg, catalyst) and 4,4,5,5-tetramethyl-2-(5-methylfuran-2-yl)-1,3,2-dioxaborolane (R-02a) (104 mg, 0.5 mmol). The solution was heated to 110° C. for 4 hours under Microwave. Then, the mixture was quenched with water and extracted with EtOAc. The organic layer was washed with brine, dried over anhydrous Na$_2$SO$_4$ and concentrated to give the crude product which was purified by prep-HPLC (General procedure, Method 6) to give the compound 2-01 (30 mg, 20%) as a yellow solid. ESI-MS (M+1): 295.1 calc. for C$_{18}$H$_{18}$N$_2$O$_2$: 294.1.

Preparation of Compound 2-02: 5-(5-methyl-2-furyl)-8-(3-pyrrolidin-1-ylpropoxy)-1,2,3,4-tetrahydrobenzo[h][1,6]naphthyridine To a solution of compound 2-01 (0.3 g, 1.02 mmol) in DCM (10 mL) was added BBr$_3$ (2.5 g, 10.2 mmol) and the solution was stirred at room temperature for 2 hours. Then, the mixture was concentrated and extracted with EtOAc. The combined organic layers were washed with brine, dried over anhydrous Na$_2$SO$_4$ and concentrated to give the crude product which was purified by column chromatography to give intermediate 5-(5-methyl-2-furyl)-1,2,3,4-tetrahydrobenzo[h][1,6]naphthyridin-8-ol (100 mg, 35%) as pale yellow solid. To a solution of this intermediate (100 mg, 0.36 mmol) and 1-(3-chloropropyl)pyrrolidine (264 mg, 1.79 mmol) in DMF (5 mL) was added Cs$_2$CO$_3$ (232 mg, 0.07 mmol) and KI (6 mg, 0.003 mmol) and the solution was heated to 110° C. for 2 hours. Then, the mixture was quenched with water and extracted with EtOAc. The organic layer was washed with brine, dried over anhydrous Na$_2$SO$_4$ and concentrated to give the crude product which was purified by prep-HPLC (General procedure, Method 1) to obtain pure compound 2-02 (12.8 mg, 9%) as a yellow solid. ESI-MS (M+1): 392 calc. for C$_{24}$H$_{29}$N$_3$O$_2$: 391.2.

Synthetic Route 4

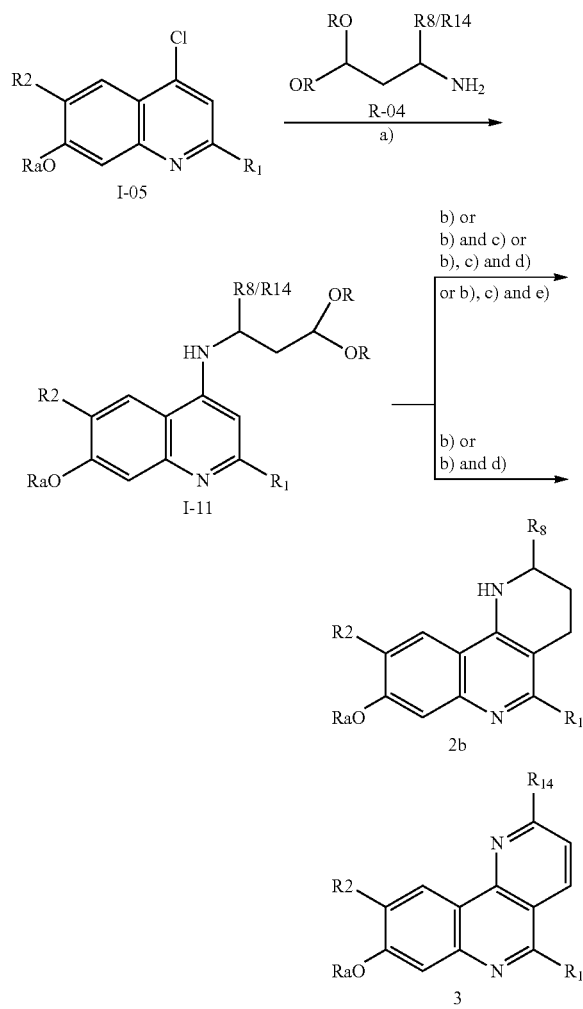

Conditions: a) R-04 (1-0-4.0 eq), Cs$_2$CO$_3$ (2.0-2.5 eq), Pd(dba)$_2$ or Pd$_2$(dba)$_3$ (0.1-0.2 eq), BINAP (0.1-0.4 eq), 1,4-dioxane, 110-120° C., 12-16 h; b) TiCl$_4$ (0.1-2.5 eq), DCM or ClCH$_2$CH$_2$Cl, 60° C., 2-12 h; c) Pd/C, H$_2$, MeOH, 15-20° C., 2 h; d) (HCHO)$_n$, (1-ethoxycyclopropyl)-trimethyl-silane, acetone or cyclohexanone (6.0-8.0 eq), NaBH$_3$CN (3.0-8.0 eq), AcOH (6.0-8.0 eq) or HCOOH (3 eq), MeOH, t-BuOH or i-PrOH, 50-70° C., 2-20 h; e) acetyl chloride (1.4 eq), Et$_3$N (3.0 eq), DCM, 25° C., 2 h.

In the scheme above R$_2$ is H or O(C$_1$-C$_6$)alkyl, R$^a$ is a hydrocarbon chain which contains nitrogen and/or oxygen atoms, R$_1$ is aryl or heteroaryl, R$_8$ and R$_{14}$ are H, a cycle (Cy) or a hydrocarbon chain which optionally contains nitrogen oxygen and/or fluor atoms, R is (C$_1$-C$_6$)alkyl, or alternatively, the two adjacent groups —OR form a 5- or 6-membered ring together with the atom to which they are attached.

Preparation of Intermediate I-11a: N-(3,3-diethoxypropyl)-6-methoxy-2-(5-methyl-2-furyl)-7-(3-pyrrolidin-1-ylpropoxy)quinolin-4-amine To a mixture of intermediate I-05a (300 mg, 748 μmol) and 3,3-diethoxypropan-1-amine (R-04a, 110 mg, 748 μmol) in 1,4-dioxane (10 mL), was added Pd(dba)$_2$ (43 mg, 74 μmol), BINAP (47 mg, 75 μmol) and Cs$_2$CO$_3$ (487 mg, 1.50 mmol) in one portion at 25° C. under N$_2$. The mixture was stirred at 25° C. for 10 minutes and then heated to 110° C. and stirred for 12 hours. Then, the mixture was concentrated in vacuum and the residue was purified by prep-TLC to afford intermediate I-11a (250 mg, 65%) as yellow solid. ESI-MS (M+1): 512.3 calc. for C$_{29}$H$_{41}$N$_3$O$_5$: 511.3.

Preparation of Compounds 2-03: 9-methoxy-5-(5-methyl-2-furyl)-8-(3-pyrrolidin-1-ylpropoxy)-1,2,3,4-tetrahydrobenzo[h][1,6]naphthyridine and 3-01: 9-methoxy-5-(5-methyl-2-furyl)-8-(3-pyrrolidin-1-yl propoxy)benzo[h]-[1,6]naphthyridine To a mixture of intermediate I-11a (80 mg, 156 μmol) in DCM (10 mL), was added TiCl$_4$ (3 mg, 15.6 μmol) in one portion at 25° C. under N$_2$ and the mixture was stirred at 25° C. for 12 hours. Then, the mixture was concentrated in reduced pressure at 45° C. and the residue was purified by prep-HPLC (General procedure, Method 2) to afford compound 2-03 (10 mg, 15%) as yellow solid [ESI-MS (M+1): 422 calc. for C$_{25}$H$_{31}$N$_3$O$_3$: 421.2] and compound 3-01 (15 mg, 23%) as yellow solid [ESI-MS (M+1): 418.1 calc. for C$_{25}$H$_{27}$N$_3$O$_3$: 417.2]

Preparation of Compound 2-04: 9-methoxy-5-(5-methyl-2-furyl)-8-(3-pyrrolidin-1-ylpropoxy)-1-(3-pyrrolidin-1-yl propyl)-3,4-dihydro-2H-benzo[h][1,6]naphthyridine To a solution of compound 2-03 (135 mg, 0.32 mmol) and 1-(3-chloropropyl)pyrrolidine (264 mg, 1.79 mmol) in DMF (5 mL) was added Cs$_2$CO$_3$ (20 mg, 0.064 mmol) and KI (6 mg, 0.003 mmol) and the solution was heated to 110° C. for 2 hours. Then, the mixture was quenched with water and extracted with EtOAc. The organic layer was washed with brine, dried over anhydrous Na$_2$SO$_4$ and concentrated to give the crude product which was purified by prep-HPLC (General procedure, Method 1) to obtained pure compound 2-04 (7.4 mg, 4%) as a yellow solid. ESI-MS (M+1): 533 calc. for C$_{32}$H$_{44}$N$_4$O$_3$: 532.3.

Preparation of Intermediate I-11b: tert-butyl 4-[3-(1,3-dioxolan-2-yl)-2-[[6-methoxy-2-(5-methyl-2-furyl)-7-(3-pyrrolidin-1-ylpropoxy)-4-quinolyl]amino]propyl]piperidine-1-carboxylate A mixture of intermediate I-05a (3 g, 7.48 mmol), tert-butyl 4-[2-amino-3-(1,3-dioxolan-2-yl)propyl]piperidine-1-carboxylate (R-04b, 9.41 g, 29.92 mmol), Cs$_2$CO$_3$ (6.1 g, 18.71 mmol), Pd$_2$(dba)$_3$ (1.37 g, 1.50 mmol) and BINAP (1.86 g, 2.99 mmol) in dioxane (100 mL) was degassed and purged with N$_2$ for 3 times. Then, the mixture was stirred at 120° C. for 16 hours under $N_2$ atmosphere. The solution was concentrated in vacuum and the residue was purified by silica gel column chromatography followed by prep-HPLC (General procedure, Method 7) to give intermediate I-11b (2 g, 39%) as a brown solid. ESI-MS (M+1): 679.5 calc. for $C_{38}H_{54}N_4O_7$: 678.4.

Preparation of Compound 2-05: 9-methoxy-5-(5-methyl-2-furyl)-2-(4-piperidylmethyl)-8-(3-pyrrolidin-1-ylpropoxy)-1,2,3,4-tetrahydrobenzo[h][1,6]naphthyridine To a solution of intermediate I-11b (100 mg, 0.14 mmol) in $ClCH_2CH_2Cl$ (10 mL) was added $TiCl_4$ (70 mg, 0.37 mmol) and the mixture was stirred at 60° C. for 2 hours. Then, the reaction mixture was poured into water (50 mL) and $NH_3.H_2O$ (25%, 5 mL). The mixture was filtered through a Celite pad and the filtrate was extracted with DCM. The combined organic phase was dried over $Na_2SO_4$ and concentrated in vacuum to give crude intermediate 9-methoxy-5-(5-methyl-2-furyl)-2-(4-piperidylmethyl)-8-(3-pyrrolidin-1-ylpropoxy)-1,2-dihydrobenzo[h][1,6]naphthyridine which was purified by prep-HPLC (General procedure, Method 8) to obtain pure intermediate (50 mg, 66%) as a yellow solid. To a solution of this intermediate (50 mg, 97 µmol) in MeOH (40 mL) was added Pd/C (10%, 0.1 g) under $N_2$ atmosphere. The suspension was degassed and purged with $H_2$ for 3 times. The mixture was stirred under $H_2$ (15 Psi) at 15° C. for 2 hours. Then, the reaction mixture was filtered through a Celite pad and the filtrate was concentrated in vacuum to give crude product. The crude product was purified by prep-HPLC (General procedure, Method 9) to obtain compound 2-05 (5 mg, 10%) as a yellow solid. ESI-MS (M+1): 519.4 calc. for $C_{31}H_{42}N_4O_3$: 518.3.

Preparation of Compound 2-06: 9-methoxy-5-(5-methyl-2-furyl)-2-[(1-methyl-4-piperidyl)methyl]-8-(3-pyrrolidin-1-ylpropoxy)-1,2,3,4-tetrahydrobenzo[h][1,6]naphthyridine To a mixture of compound 2-05 (26.0 mg, 50 µmol) and $(HCHO)_n$ (12.1 mg, 401 µmol) in MeOH (30 mL) were added $NaBH_3CN$ (25.2 mg, 401 µmol) and AcOH (24.1 mg, 401 µmol) in one portion at 16° C. under $N_2$. The mixture was stirred at 50° C. for 2 hours. Then, the reaction mixture was cooled to 16° C., filtered and concentrated in vacuum. The residue was purified by prep-HPLC (General procedure, Method 1) to afford the desired compound 2-06 (5.8 mg, 22%) as yellow solid. ESI-MS (M+1): 533.4 calc. for $C_{32}H_{44}N_4O_3$: 532.3. HPLC analytical method 1, Rt=2.70 min.

Preparation of Compound 2-07: 2-[(1-cyclopropyl-4-piperidyl)methyl]-9-methoxy-5-(5-methyl-2-furyl)-8-(3-pyrrolidin-1-ylpropoxy)-1,2,3,4-tetrahydrobenzo[h][1,6]naphthyridine To a solution of compound 2-05 (40 mg, 77 µmol) in t-BuOH (5 mL) (1-ethoxycyclopropyl)-trimethyl-silane (73 mg, 462 µmol), $NaBH_3CN$ (29 mg, 462 µmol) and AcOH (28 mg, 462 µmol) were added. The mixture was stirred at 60° C. for 40 hours. Then, the reaction mixture was concentrated in vacuum to give a residue which was purified by prep-HPLC (General procedure, Method 10) to give compound 2-07 (8.5 mg, 20%) as a yellow solid. ESI-MS (M+1): 559.5 calc. for $C_{34}H_{46}N_4O_3$: 558.3.

Preparation of Compound 2-08: 2-[(1-isopropyl-4-piperidyl)methyl]-9-methoxy-5-(5-methyl-2-furyl)-8-(3-pyrrolidin-1-ylpropoxy)-1,2,3,4-tetrahydrobenzo[h][1,6]naphthyridine To a solution of compound 2-05 (40 mg, 77 µmol) in i-PrOH (5 mL) acetone (27 mg, 462 µmol), $NaBH_3CN$ (29 mg, 462 µmol) and AcOH (28 mg, 462 µmol) were added. The mixture was stirred at 60° C. for 16 hours. Then, the reaction mixture was concentrated in vacuum to give a residue which was purified by prep-HPLC (General procedure, Method 9) to give pure compound 2-08 (5 mg, 12%) as a yellow solid. ESI-MS (M+1): 561.5 calc. for $C_{34}H_{48}N_4O_3$: 560.3.

Preparation of Compounds 2-09 and 2-10: (2R)-9-methoxy-5-(5-methyl-2-furyl)-2-[(1-methyl-4-piperidyl)methyl]-8-(3-pyrrolidin-1-ylpropoxy)-1,2,3,4-tetrahydrobenzo[h][1,6]naphthyridine and (2S)-9-methoxy-5-(5-methyl-2-furyl)-2-[(1-methyl-4-piperidyl)methyl]-8-(3-pyrrolidin-1-ylpropoxy)-1,2,3,4-tetrahydrobenzo[h][1,6]naphthyridine Compound 2-06 (100 mg) was purified by SFC (General method described above) to afford compound 2-09 (25.7 mg, 48 µmol) as a white solid and compound 2-10 (19.6 mg, 37 µmol) as a white solid (stereochemistry randomly assigned).
2-08: ESI-MS (M+1): 533.4 calc. for $C_{32}H_{44}N_4O_3$: 532.34. HPLC analytical method 1, Rt=2.69 min.
2-09: ESI-MS (M+1): 533.4 calc. for $C_{32}H_{44}N_4O_3$: 532.34. HPLC analytical method 1, Rt=2.71 min.

Preparation of Compound 2-11: 1-[4-[[9-methoxy-5-(5-methyl-2-furyl)-8-(3-pyrrolidin-1-ylpropoxy)-1,2,3,4-tetrahydrobenzo[h][1,6]naphthyridin-2-yl]methyl]-1-piperidyl]ethanone A mixture of compound 2-05 (30 mg, 58 µmol), $Et_3N$ (17 mg, 173 µmol) and acetyl chloride (6.81 mg, 86 µmol) in DCM (5 mL) was degassed and purged with $N_2$ for 3 times. Then, the mixture was stirred at 25° C. for 2 hours under $N_2$ atmosphere. Then, the reaction mixture was concentrated under vacuum and purified by prep-HPLC (General Procedure, Method 11) to give compound 2-11 (5.80 mg, 18%) as a yellow solid. ESI-MS (M+1): 561.4 calcd. For $C_{33}H_{44}N_4O_4$: 560.34. HPLC analytical method 2, Rt=2.13

Preparation of Compound 2-12: 2-[(1-cyclohexyl-4-piperidyl)methyl]-9-methoxy-5-(5-methyl-2-furyl)-8-(3-pyrrolidin-1-ylpropoxy)-1,2,3,4-tetrahydrobenzo[h][1,6]naphthyridine Compound 2-12 was obtained in an analogous manner to compound 2-06 using cyclohexanone. Purification by prep-HPLC (General Procedure, Method 11), 16% yield. ESI-MS (M+1): 601.5 calcd. For $C_{37}H_{52}N_4O_3$ 600.40. HPLC analytical method 2, Rt=1.79

Preparation of Compound 3-02: 9-methoxy-5-(5-methyl-2-furyl)-2-(4-piperidylmethyl)-8-(3-pyrrolidin-1-ylpropoxy)benzo[h][1,6]naphthyridine To a solution of compound intermediate I-11b (310.0 mg, 456 µmol) in $ClCH_2CH_2Cl$ (50 mL) was added $TiCl_4$ (216 mg, 1.14 mmol) slowly at 20° C. and the resulting mixture was stirred at 60° C. for 12 hours. Then, the reaction was quenched by adding $NH_4OH$ (12 mL, 25%) and then to afford the desired compound 3-02 (36.0 mg, 15%) as yellow solid. ESI-MS (M+1): 515.4 calc. for $C_{31}H_{38}N_4O_3$: 514.3. HPLC analytical method 1, Rt=2.92 min.

Preparation of Compound 3-03: 9-methoxy-5-(5-methyl-2-furyl)-2-[(1-methyl-4-piperidyl)methyl]-8-(3-pyrrolidin-1-ylpropoxy)benzo[h][1,6]naphthyridine To a mixture of compound 3-02 (36 mg, 70 μmol) and (HCHO)$_n$ (16.8 mg, 560 μmol) in MeOH (30 mL) were added NaBH$_3$CN (35.2 mg, 560 μmol) and AcOH (33.6 mg, 560 μmol) in one portion under N$_2$ and the mixture was stirred at 50° C. for 2 hours. Then, the mixture was cooled to 16° C., filtered and concentrated in vacuum. The residue was purified by prep-HPLC (General procedure, Method 1) to afford compound 3-03 (32.6 mg, 88%) as a yellow solid. ESI-MS (M+1): 529.4 calc. for $C_{32}H_{40}N_4O_3$: 528.3. HPLC analytical method 1, Rt=3.02 min.

Preparation of Intermediate I-11c: tert-butyl 4-(2-((2-(2,5-dimethylfuran-3-yl)-6-methoxy-7-(3-(pyrrolidin-1-yl)propoxy)quinolin-4-yl)amino)-3-(1,3-dioxolan-2-yl)propyl)piperidine-1-carboxylate A mixture of intermediate I-05e (1.00 g, 2.41 mmol), tert-butyl 4-[2-amino-3-(1,3-dioxolan-2-yl)propyl]piperidine-1-carboxylate (R-04b, 909.30 mg, 2.89 mmol), Cs$_2$CO$_3$ (1.57 g, 4.82 mmol), Pd$_2$(dba)$_3$ (221 mg, 241 μmol) and BINAP (150 mg, 241 μmol) in dioxane (50 mL) was degassed and purged with N$_2$ for 3 times. Then, the mixture was stirred at 120° C. for 12 hours under N$_2$ atmosphere. The mixture was cooled to 20° C. and concentrated in reduced pressure at 40° C. The residue was poured into water (50 mL) and extracted with ethyl acetate (50 mL×3). The combined organic phase was washed with brine (50 mL×2), dried with anhydrous Na$_2$SO$_4$, filtered and concentrated in vacuum. The residue was purified by prep-HPLC (General procedure, Method 13) to give intermediate I-11c. Then acidified to pH=8 with NaHCO$_3$(s) to give intermediate I-11c (500 mg, 30%) as a yellow solid. ESI-MS (M+1): 693.4 calc. for $C_{39}H_{56}N_4O_7$: 692.41.

Preparation of Compound 2-13: 9-methoxy-5-(2,5-dimethyl-3-furyl)-2-[(1-methyl-4-piperidyl)methyl]-8-(3-pyrrolidin-1-ylpropoxy)-1,2,3,4-tetrahydrobenzo[h][1,6]naphthyridine A mixture of intermediate I-11c (200 mg, 288.65 μmol), TiCl$_4$ (55 mg, 289.96 μmol) in ClCH$_2$CH$_2$Cl (10 mL) was degassed and purged with N$_2$ for 3 times, and then the mixture was stirred at 60° C. for 2 hours under N$_2$ atmosphere. Then, the reaction mixture was quenched by NH$_3$H$_2$O (1 mL, 25%) and Na$_2$SO$_4$ (2 g) was added, stirred at 15° C. for 1 hour, then filtered and concentrated to give the crude intermediate 5-(2,5-dimethyl-3-furyl)-9-methoxy-2-(4-piperidylmethyl)-8-(3-pyrrolidin-1-ylpropoxy)-1,2-dihydrobenzo[h][1,6]naphthyridine, which was purified by prep-HPLC (General procedure, Method 14) to obtain pure intermediate (50 mg, 27%) as a yellow solid. To a solution of this intermediate (40 mg, 62.04 μmol) in MeOH (10 mL) was added Pd/C (10%, 10 mg) under H$_2$ atmosphere. The suspension was degassed and purged with H$_2$ for 3 times. The mixture was stirred under H$_2$ (15 Psi) at 20° C. for 2 hours. Then, the reaction mixture was filtered and concentrated in reduced pressure at 40° C. to give crude intermediate 5-(2,5-dimethyl-3-furyl)-9-methoxy-2-(4-piperidylmethyl)-8-(3-pyrrolidin-1-ylpropoxy)-1,2,3,4-tetrahydrobenzo[h][1,6]naphthyridine (30 mg, 75%) as a yellow solid. A mixture of this intermediate (30 mg, 46.39 μmol), HCOOH (7 mg, 139.16 μmol), (HCHO)$_n$ (13 mg, 139.16 μmol) and NaBH$_3$CN (9 mg, 139.16 μmol) in MeOH (3 mL) was degassed and purged with N$_2$ for 3 times. Then, the mixture was stirred at 70° C. for 2 hours under N$_2$ atmosphere. The mixture was filtered and concentrated in vacuum to give the crude product which was purified by prep-HPLC (General procedure, Method 14) to afford the desired compound 2-13 (1.80 mg, 5.9%) as yellow solid. ESI-MS (M+1): 547.4 calc. for $C_{33}H_{46}N_4O_3$: 546.36. HPLC analytical method 3, Rt=1.57 min.

Preparation of Compound 3-04: 9-methoxy-5-(2,5-dimethyl-3-furyl)-2-[(1-methyl-4-piperidyl)methyl]-8-(3-pyrrolidin-1-ylpropoxy)benzo[h][1,6-]naphthyridine A mixture of intermediate I-11c (200 mg, 288.65 μmol), TiCl$_4$ (55 mg, 289.66 μmol) in ClCH$_2$CH$_2$Cl (30 mL) was degassed and purged with N$_2$ for 3 times, and then the mixture was stirred at 60° C. for 3 hours under N$_2$ atmosphere. Then, the reaction mixture was quenched by NH$_3$H$_2$O (3 mL, 25%) and Na$_2$SO$_4$ (10 g) was added, stirred at 15° C. for 1 hour, then filtered and concentrated to give the crude intermediate, which was purified by prep-HPLC (General procedure, Method 15) to obtain pure intermediate 5-(2,5-dimethyl-3-furyl)-9-methoxy-2-(4-piperidylmethyl)-8-(3-pyrrolidin-1-ylpropoxy)benzo[h][1,6]naphthyridine (40 mg, 21.56%) as a yellow solid. A mixture of this intermediate (40 mg, 62.24 μmol), HCOOH (9 mg, 186.72 μmol), (HCHO)$_n$ (17 mg, 186.72 μmol) and NaBH(OAc)$_3$ (40 mg, 186.72 μmol) in MeOH (5 mL) was degassed and purged with N$_2$ for 3 times, and then the mixture was stirred at 60° C. for 16 hours under N$_2$ atmosphere. The mixture was cooled to 20° C. and concentrated in reduced pressure at 40° C. The crude product was purified by prep-HPLC (General procedure, Method 16) to give compound 3-04 (3.00 mg, 7.32%) as yellow syrup. ESI-MS (M+1): 543.5 calc. for $C_{33}H_{42}N_4O_3$: 542.33. HPLC analytical method 3, Rt=2.93 min.

Synthetic Route 5

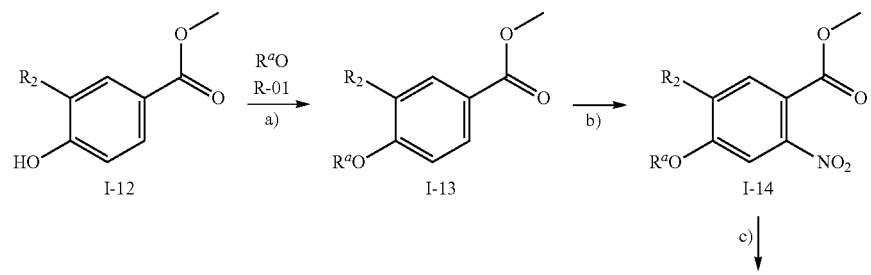

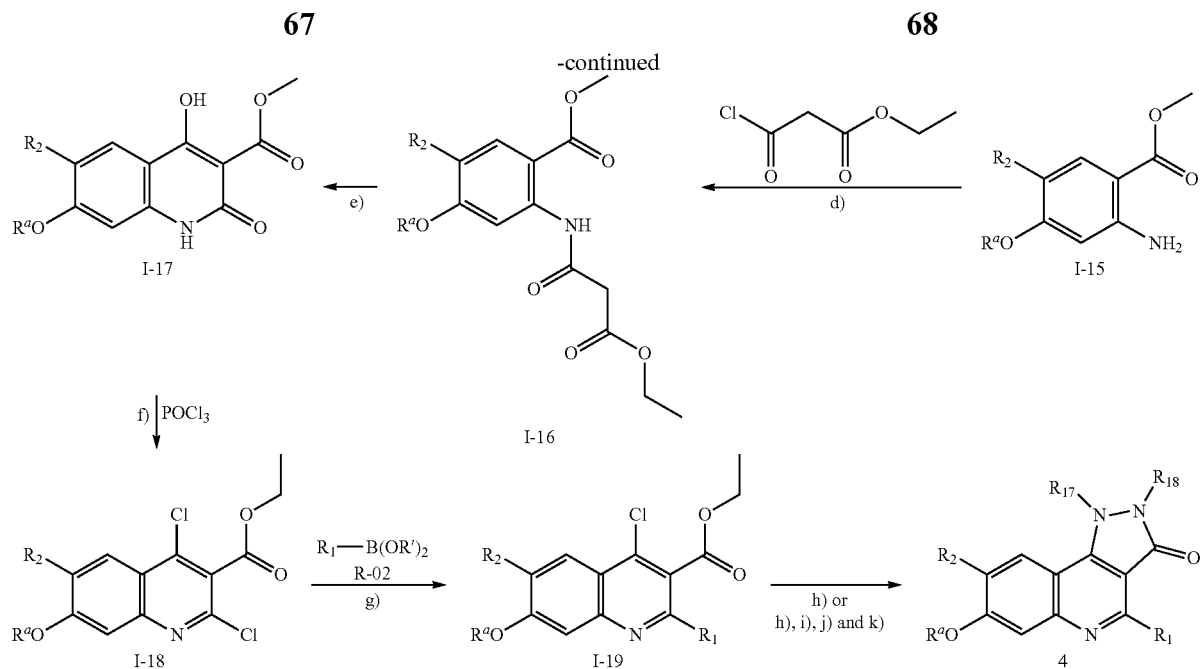

Conditions: a) DIAD (2.0 eq), R-01 (1.0 eq), PPh₃ (2.0 eq), THF, rt, 30 h; b) SnCl₄ (1.65 eq), HNO₃ (1.65 eq), DCM, -25° C., 2 h, then rt, 4 h; c) Pd/C, H₂, MeOH, rt, 30 h; d) pyridine (4.0 eq), DMAP (0.05 eq), DCM, 0° C., 1 h, then ethyl 3-chloro-3-oxo-propanoate (1.0 eq), rt, 15 h; e) KHMDS (4.0 eq), THF, -70° C., then rt overnight; f) POCl₃, 120° C., 15 h; g) R-02 (1.1 eq), Pd(PPh₃)₄ (0.1 eq), 1,4-dioxane, 85° C., 20 h; h) hydrazine hydrate or methylhydrazine (10 eq), DIEA (16 eq), EtOH, 100° C., MW, 6 h; i) tert-butyl 4-methylsulfonyloxypiperidine-1-carboxylate or tert-butyl 4-(methylsulfonyloxymethyl)piperidine-1-carboxylate (1.0-0.8eq), K₂CO₃ (2.5 eq), DMF, 60° C., 4 h; j) HCl/EtOAc (1.0 N), 22° C., 3 h; k) (HCHO)$_n$ (6.0 eq), AcOH (3.0 eq), NaBH(OAc)₃ (6.0 eq), MeOH, 60° C., 15 h.

In the scheme above $R_2$ is H or $O(C_1\text{-}C_6)$alkyl, $R_a$ is a hydrocarbon chain which contains nitrogen and/or oxygen atoms, $R_1$ is aryl or heteroaryl, $R_{17}$ and $R_{18}$ are H, a cycle (Cy) or a hydrocarbon chain which optionally contains nitrogen oxygen and/or fluor atoms, and R' is H, $(C_1\text{-}C_6)$ alkyl or, alternatively, two R' groups together with the B atom to which they are attached may form a cycle.

Preparation of Intermediate I-13a: methyl 3-methoxy-4-(3-pyrrolidin-1-ylpropoxy)benzoate To a solution of commercially available methyl 4-hydroxy-3-methoxy-benzoate (I-12a, 146 g, 800 mmol) in THF (4 L) was added DIAD (323 g, 1.60 mol), 3-pyrrolidin-1-ylpropan-1-ol (R-01a, 103 g, 800 mmol) and PPh₃ (419 g, 1.60 mol) at 0° C. and the solution was stirred at room temperature for 30 hours. Then, the reaction mixture was concentrated and extracted with EtOAc. The combined organic layers were washed with brine, dried over anhydrous Na₂SO₄ and concentrated to give the crude product which was purified by column chromatography to give intermediate I-13a (176 g, 75%). ESI-MS (M+1): 294.0 calc. for $C_{16}H_{23}NO_4$: 293.2.

Preparation of Intermediate I-14a: methyl 5-methoxy-2-nitro-4-(3-pyrrolidin-1-ylpropoxy)benzoate To a mixture of intermediate I-13a (53 g, 180 mmol) in CH₂Cl₂ (300 mL), was added a solution of SnCl₄ (77 g, 297 mmol) and HNO₃ (18.71 g, 297 mmol) in CH₂Cl₂ (300 mL) in dropwise at -25° C. The mixture was stirred at -25° C. for 2 hours and room temperature for 4 hours. Then, the reaction was quenched with water and extracted with EtOAc. The combined organic phase was washed with saturated brine, dried with anhydrous Na₂SO₄, filtered and concentrated in vacuum. The residue was purified by column chromatography to afford intermediate I-14a (58 g, 95%) as yellow oil. ESI-MS (M+1): 339.3 calc. for $C_{16}H_{22}N_2O_6$: 338.1.

Preparation of Intermediate I-15a: methyl 2-amino-5-methoxy-4-(3-pyrrolidin-1-ylpropoxy)benzoate To a solution of intermediate I-14a (58 g, 172 mmol) in MeOH (1000 mL) was added Pd/C (8.00 g, 74 mmol) and the mixture was stirred at room temperature for 30 hours under H₂ (45 Psi). Then, the solution was filtered, and the filtrate was concentrated to give the crude intermediate I-15a (55 g, 99% crude) as yellow liquid which was used directly for the next step. ESI-MS (M+1): 309.0 calc. for $C_{16}H_{24}N_2O_4$: 308.2.

Preparation of Intermediate I-16a: methyl 2-[(3-ethoxy-3-oxo-propanoyl)amino]-5-methoxy-4-(3-pyrrolidin-1-ylpropoxy)benzoate DMAP (348 mg, 2.85 mmol) and pyridine (15.8 g, 200 mmol) were added to a stirred suspension of intermediate I-15a (17.6 g, 57 mmol) in CH₂Cl₂ (60 mL) at 0° C. under nitrogen and the resulting solution was stirred at 0° C. for 1 hour. Then, ethyl 3-chloro-3-oxo-propanoate (9.02 g, 60 mmol) was added over a period of 10 minutes under nitrogen and the resulting solution was stirred at room temperature for 15 hours. The reaction was quenched with water and extracted with DCM. The combined organic phase was washed with saturated brine, dried over anhydrous Na₂SO₄, filtered and concentrated in vacuum. The residue was purified by column chromatography to give intermediate I-16a (14.3 g, 59%). ESI-MS (M+1): 423.0 calc. for $C_{21}H_{30}N_2O_7$: 422.2.

Preparation of Intermediate I-17a: ethyl 4-hydroxy-6-methoxy-2-oxo-7-(3-pyrrolidin-1-ylpropoxy)-1H-quinoline-3-carboxylate To a solution of intermediate I-16a (10 g, 23 mmol) in THF (120 mL) were successively added KHMDS (92 mL, 1.0 N in THF, 92 mmol) at −70° C. and the resulting mixture was stirred at room temperature overnight. Then, the solution was diluted with water and extracted with EtOAc. The organic layer was washed with water and brine, and then concentrated to give intermediate I-17a (10.0 g) which used directly in next step. ESI-MS (M+1): 391.2 calc. for $C_{20}H_{26}N_2O_6$: 390.2.

Preparation of Intermediate I-18a: ethyl 2,4-dichloro-6-methoxy-7-(3-pyrrolidin-1-ylpropoxy)quinoline-3-carboxylate A solution of intermediate I-17a (10 g, 25 mmol) in $POCl_3$ (100 mL) was stirred at 120° C. for 15 hours. Then, the mixture was concentrated to give the crude compound which was purified by column chromatography to obtain pure intermediate I-18a (2.77 g, 26%). ESI-MS (M+1): 427.1 calc. for $C_{20}H_{24}Cl_2N_2O_4$: 426.1.

Preparation of Intermediate I-19a: ethyl 4-chloro-6-methoxy-2-(5-methyl-2-furyl)-7-(3-pyrrolidin-1-ylpropoxy)quinoline-3-carboxylate To a solution of intermediate I-18a (3.45 g, 8.0 mmol) in 1,4-dioxane (50 mL) were successively added $Pd(PPh_3)_4$ (923 mg, 800 µmol) and 4,4,5,5-tetramethyl-2-(5-methyl-2-furyl)-1,3,2-dioxaborolane (R-02a, 1.83 g, 8.8 mmol). The resulting mixture was stirred at 85° C. for 20 hours. Then, the solution was diluted with water and extracted with EtOAc. The organic layer was washed with water and brine and then concentrated to get crude product which was purified by prep-HPLC (General procedure, Method 1) to obtain pure intermediate I-19a (1.52 g, 40%). ESI-MS (M+1): 473.3. calc. for $C_{25}H_{29}ClN_2O_5$: 472.2.

Preparation of Compound 4-01: 8-methoxy-2-methyl-4-(5-methyl-2-furyl)-7-(3-pyrrolidin-1-ylpropoxy)-1H-pyrazolo[4,3-c]quinolin-3-one To a solution of intermediate I-19a (50 mg, 105 µmol) in EtOH (10 mL) was added methylhydrazine (50 mg, 1.09 mmol, 50% in water) and DIEA (205 mg, 1.59 mmol) and the mixture was stirred at 100° C. under Microwave for 6 hours. Then, the solution was concentrated to give the crude product which was purified by prep-HPLC (General procedure, Method 1) to obtain pure compound 4-01 (9.1 mg, 20%) as a yellow solid. ESI-MS (M+1): 437.2 calc. for $C_{24}H_{28}N_4O_4$: 436.2. HPLC analytical method 1, Rt=2.66 min.

Preparation of Compound 4-02: 8-methoxy-4-(5-methyl-2-furyl)-7-(3-pyrrolidin-1-ylpropoxy)-1,2-dihydropyrazolo[4,3-c]quinolin-3-one Compound 4-02 was obtained in an analogous manner to compound 4-01 using hydrazine hydrate. The crude product was purified prep-HPLC (General procedure, Method 1) to obtain compound 4-02 as a yellow solid (58% yield). ESI-MS (M+1): 423.2 calc. for $C_{24}H_{28}N_4O_4$: 422.2. HPLC analytical method 2, Rt=1.66 min.

Preparation of Compound 4-03: 8-methoxy-4-(5-methyl-2-furyl)-2-(1-methyl-4-piperidyl)-7-(3-pyrrolidin-1-ylpropoxy)-1H-pyrazolo[4,3-c]quinolin-3-one To a solution of compound 4-02 (120 mg, 284 µmol) and tert-butyl 4-methylsulfonyloxypiperidine-1-carboxylate (63 mg, 227 µmol) in anhydrous DMF (15 mL) was added $K_2CO_3$ (98 mg, 710 µmol) and the mixture was stirred at 60° C. for 4 hours. Then, the reaction was quenched with water and extracted with EtOAc. The combined organic phase was washed with brine, dried over $Na_2SO_4$, filtered, concentrated and purified by prep-HPLC (General procedure, Method 1) to give intermediate tert-butyl 4-[8-methoxy-4-(5-methyl-2-furyl)-3-oxo-7-(3-pyrrolidin-1-ylpropoxy)-1H-pyrazolo[4,3-c]quinolin-2-yl]piperidine-1-carboxylate (128 mg, 74%) as a yellow solid. A solution of this intermediate (210 mg, 347 µmol) in HCl/EtOAc (40 mL, 1.0 N) was stirred at 22° C. for 3 hours. Then the mixture was concentrated to dryness to give the crude intermediate 8-methoxy-4-(5-methyl-2-furyl)-2-(4-piperidyl)-7-(3-pyrrolidin-1-ylpropoxy)-1H-pyrazolo[4,3-c]quinolin-3-one (192 mg, crude) which was used directly in next step without further purification. To a mixture of this intermediate (188 mg, 347 µmol) and $(HCHO)_n$ (187 mg, 2.08 mmol) in MeOH (20 mL) were added HCOOH (50 mg, 1.04 mmol) and $NaBH(OAc)_3$ (441 mg, 2.08 mmol) in one portion at 20° C. under $N_2$ and the mixture was stirred at 20° C. for 10 minutes, then heated to 60° C. and stirred for 15 hours. The mixture was cooled to 20° C., filtered and concentrated in vacuum. The residue was purified by prep-HPLC (General procedure, Method 1) to afford compound 4-03 (26.9 mg, 15%) as a yellow solid. ESI-MS (M+1): 520.3 calc. for $C_{29}H_{37}N_5O_4$: 519.3. HPLC analytical method 1, Rt=2.45 min.

Preparation of Compound 4-04: 8-methoxy-4-(5-methyl-2-furyl)-2-[(1-methyl-4-piperidyl)methyl]-7-(3-pyrrolidin-1-ylpropoxy)-1H-pyrazolo[4,3-c]quinolin-3-one To a solution of compound 4-02 (100 mg, 236 µmol) and tert-butyl 4-(methylsulfonyloxymethyl)piperidine-1-carboxylate (55 mg, 189 µmol) in anhydrous DMF (15 mL) was added $K_2CO_3$ (82 mg, 592 µmol) and the mixture was stirred at 60° C. for 4 hours. Then, the reaction was quenched with water and extracted with EtOAc. The combined organic phase was washed with brine, dried over $Na_2SO_4$, filtered, concentrated and purified by prep-HPLC (General procedure, Method 1) to give intermediate tert-butyl 4-[[8-methoxy-4-(5-methyl-2-furyl)-3-oxo-7-(3-pyrrolidin-1-ylpropoxy)-1H-pyrazolo[4,3-c]quinolin-2-yl]methyl]piperidine-1-carboxylate (83 mg, 57%) as a yellow solid. A solution of this intermediate (125 mg, 202 µmol) in HCl/EtOAc (40 mL, 1.0 N) was stirred at 22° C. for 3 hours. Then, the mixture was concentrated to dryness to give intermediate 8-methoxy-4-(5-methyl-2-furyl)-2-(4-piperidylmethyl)-7-(3-pyrrolidin-1-ylpropoxy)-1H-pyrazolo[4,3-c]quinolin-3-one (115 mg, crude) which was used for next step without further purification. To a mixture of this intermediate (112 mg, 202 µmol) and $(HCHO)_n$ (109 mg, 1.21 mmol) in MeOH (20 mL) were added HCOOH (29 mg, 605 µmol) and $NaBH(OAc)_3$ (256 mg, 1.21 mmol) in one portion at 20° C. under $N_2$. The mixture was stirred at 20° C. for 10 minutes and then heated to 60° C. and stirred for 15 hours. The mixture was filtered and the filtrate was concentrated under vacuum and purified by prep-HPLC (General procedure, Method 1) to afford compound 4-04 (15.8 mg, 15%) as a yellow solid. ESI-MS (M+1): 534.4 calc. for $C_{30}H_{39}N_5O_4$: 533.3. HPLC analytical method 1, Rt=2.65 min.

Preparation of Compound 4-05: 8-methoxy-4-(5-methyl-2-furyl)-1,2-bis[(1-methyl-4-piperidyl)methyl]-7-(3-pyrrolidin-1-ylpropoxy)pyrazolo[4,3-c]quinolin-3-one To a solution of compound 4-02 (50 mg, 118 µmol) and compound tert-butyl 4-(methylsulfonyloxymethyl)piperidine-1-carboxylate (39.5 mg, 142 µmol) in anhydrous DMF (15 mL) was added $K_2CO_3$ (41 mg, 296 µmol) and the mixture was stirred at 60° C. for 4 hours. Then, the reaction was quenched with water and extracted with EtOAc. The combined organic phase was washed with brine, dried over $Na_2SO_4$, filtered, concentrated and purified by prep-HPLC (General procedure, Method 1) to give intermediate tert-butyl 4-[[2-[(1-tert-butoxycarbonyl-4-piperidyl)methyl]-8-methoxy-4-(5-methyl-2-furyl)-3-oxo-7-(3-pyrrolidin-1-ylpropoxy)pyrazolo[4,3-c]quinolin-1-yl]methyl]piperidine-1-carboxylate (42 mg, 44%) as a yellow solid. A solution of this intermediate (183 mg, 224 µmol) in HCl/EtOAc (40 mL, 1.0 N) was stirred at 22° C. for 3 hours. Then, the mixture was concentrated to dryness to give the crude intermediate 8-methoxy-4-(5-methyl-2-furyl)-1,2-bis(4-piperidylmethyl)-7-(3-pyrrolidin-1-ylpropoxy)pyrazolo[4,3-c]quinolin-3-one (156 mg, crude) which was used for next step without further purification. To a mixture of this intermediate (138 mg, 224 µmol) and $(HCHO)_n$ (121 mg, 1.34 mmol) in MeOH (20 mL) were added HCOOH (32 mg, 672 µmol) and $NaBH(OAc)_3$ (285 mg, 1.34 mmol) in one portion at 22° C. under $N_2$. The mixture was stirred at 22° C. for 10 minutes and then heated to 60° C. and stirred for 15 hours. The mixture was cooled to 22° C. and filtered. The filtrate was concentrated under vacuum and purified by prep-HPLC (General procedure, Method 1) to give compound 4-05 (33 mg, 23%) as a yellow solid. ESI-MS (M+1): 645.5 calc. for $C_{37}H_{52}N_6O_4$: 644.4. HPLC analytical method 1, Rt=2.37 min.

Biological Tests

G9a Enzyme Activity Assay

The biochemical assay to measure G9a enzyme activity relies on time-resolved fluorescence energy transfer (TR-FRET) between europium cryptate (donor) and XL665 (acceptor). TR-FRET is observed when biotinylated histone monomethyl-H3K9 peptide is incubated with cryptate-labeled anti-dimethyl-histone H3K9 antibody (CisBio Cat#61KB2KAE) and streptavidin XL665 (CisBio Cat#610SAXLA), after enzymatic reaction of G9a.

The human G9a enzyme expressed in a baculovirus infected Sf9 cell expression system was obtained from BPS Biosciences (Cat. #51001). Enzyme activity assay was carried out in a white 384-well plate in a final volume of 20 µl, as follow:

4 µl of vehicle or studied compound 2.5× concentrated prepared in assay buffer (50 mM Tris-HCl, 10 mM NaCl, 4 mM DTT, 0.01% Tween-20 pH9). Final percentage of DMSO was 0.5%.

2 µl of 1 nM G9a enzyme diluted in assay buffer. Final concentration was 0.2 nM.

Start the reaction by adding 4 µl of substrate mixture containing 20 µM S-adenosylmethionine and 40 nM biotinylated histone monomethyl-H3K9 peptide.

Reaction was carried out during 1 hour at room temperature.

Enzyme activity was stopped by adding 5 µl of cryptate-labeled anti-dimethyl-histone H3K9 antibody. Final concentration 150 nM.

Then, add 5 µl of streptavidin XL665 beads. Final concentration of 16 µM.

Read the plate after 1 hour of incubation at room temperature.

For each well, fluorescence was measured at 620 nm and 665 nm. A ratio (665 nm/620 nm) was then calculated in order to minimize medium interferences. Positive control was obtained in the presence of the vehicle of the compounds. Negative control was obtained in the absence of G9a enzyme activity. Calculated $IC_{50}$ values were determined using GraphPrism using 4-parameters inhibition curve.

DNMT1 Enzyme Activity Assay

The biochemical assay to measure DNMT1 enzyme activity relies on time-resolved fluorescence energy transfer (TR-FRET) between lumi4-Tb (donor) and d2 (acceptor) using the EPIgeneous methyltransferase assay (CisBio Cat#62SAHPEB). TR-FRET is observed when antibody specific to S-adenosylhomocysteine labeled with Lumi4-Tb is incubated with d2-labeled S-adenosylhomocysteine. TR-FRET signal is inversely proportional to the concentration of SAH, product of DNMT1 enzyme activity, in the sample. The human DNMT1 was obtained from Reaction Biology Corp. (Cat# DMT-21-124).

Enzyme activity assay was carried out in a white 384-well plate in a final volume of 20 µl, as follow:

4 µl of vehicle or studied compound 2.5× concentrated prepared in assay buffer (50 mM Tris-HCl, 1 mM EDTA, 1 mM DTT, 0.1% Triton X-100, 5% glycerol pH 7.5). Final percentage of DMSO was 0.5%.

2 µl of 1 nM DNMT1 enzyme diluted in assay buffer. Final concentration was 20 nM.

Start the reaction by adding 4 µl of substrate mixture containing 1 µM S-adenosylmethionine and 1 µM poly-deoxy inosine poly-deoxy cytosine (pdI-pdC) DNA.

Reaction was carried out during 15 minutes at 37° C.

Enzyme activity was stopped by adding 2 µl of buffer one of the EPIgeneous methyltransferase assay.

After 10 minutes at room temperature, it was added 4 µl of antibody specific to S-adenosylhomocysteine labeled with Lumi4-Tb 50× diluted in buffer two of the EPIgeneous methyltransferase assay.

Add 4 µl of d2-labeled S-adenosylhomocysteine 31× diluted in buffer two of the EPIgeneous methyltransferase assay.

Read the plate after 1 hour of incubation at room temperature.

For each well, fluorescence was measured at 620 nm and 665 nm. A ratio (665 nm/620 nm) was then calculated in order to minimize medium interferences. Positive control was obtained in the presence of the vehicle of the compounds. Negative control was obtained in the absence of G9a enzyme activity. Calculated $IC_{50}$ values were determined using GraphPrism using 4-parameters inhibition curve.

Table 2 shows the inhibition values for G9a and DNMTs ($IC_{50}$) for selected compounds; where 1 µM≤$IC_{50}$≤10 µM (+), 500 nM≤$IC_{50}$≤1 µM (++), 100 nM≤$IC_{50}$<500 nM (+++), $IC_{50}$<100 nM (++++) and $IC_{50}$>10 µM (N.A. not active)

TABLE 2

| Compound | G9a IC$_{50}$ (M) | DNMT1 IC$_{50}$ (M) |
| --- | --- | --- |
| 1-02 | +++ | +++ |
| 1-03 | +++ | ++ |
| 1-04 | +++ | ++ |
| 1-05 | +++ | ++ |
| 1-06 | ++ | + |
| 2-01 | N.A. | + |
| 2-02 | + | ++ |
| 2-03 | ++++ | + |
| 2-04 | N.A. | ++ |
| 2-05 | ++++ | ++ |
| 2-06 | ++++ | +++ |
| 2-07 | ++++ | ++ |
| 2-08 | ++++ | ++ |
| 2-09 | ++++ | ++ |
| 2-10 | ++++ | ++ |
| 2-11 | ++++ | + |
| 2-12 | ++++ | ++ |
| 2-13 | ++++ | + |
| 3-01 | + | + |
| 3-02 | +++ | ++ |
| 3-03 | ++++ | + |
| 3-04 | +++ | N.A. |
| 4-03 | N.A. | + |
| 4-04 | N.A. | + |
| 4-05 | N.A. | + |

Cell Proliferation Assay

Cell proliferation was analyzed after 48 hours of in vitro treatment using the CellTiter 96 Aqueous One Solution Cell Proliferation Assay (Promega, Madison, W). This is a colorimetric method for determining the number of viable cells in proliferation.

For the assay, suspension cells were cultured by triplicate at a density of 1×10$^6$ cells/ml in 96-well plates (100.000 cells/well, 100 µl/well), except for OCI-Ly3 and OCI-Ly10 cell lines which were cultured at a density of 0.5×10$^6$ cells/ml (50,000 cells/well, 100 µl/well) and for HepG2, Hep3B and PLC/PRF/5 cell lines which were cultured at a density of 3000 cells/well, 100 µl/well). Adherent cells were obtained from 80-90% confluent flasks and 100 µl of cells were seeded at a density of 5000 cells/well in 96-well plates by triplicate. Before addition of the compounds, adherent cells were allowed to attach to the bottom of the wells for 12 hours. In all cases, only the 60 inner wells were used to avoid any border effects.

After 48 hours of treatment, plates with suspension cells were centrifuged at 800 g for 10 minutes and medium was removed. The plates with adherent cells were flicked to remove medium. Then, cells were incubated with 100 µl/well of medium and 20 µl/well of CellTiter 96 Aqueous One Solution reagent. After 1-3 hours of incubation at 37° C., absorbance was measured at 490 nm in a 96-well plate reader. The background absorbance was measured in wells with only cell line medium and solution reagent. Data was calculated as a percentage of total absorbance of treated cell/absorbance of non treated cells.

Table 3 shows the functional response of selected compounds on established cell lines and primary cultures (GI$_{50}$, which is concentration of compound for 50% of maximal inhibition of cell proliferation); where, GI$_{50}$≥10 µM (+), 1 µM≤GI$_{50}$<10 µM (++), 100 nM≤GI$_{50}$<1 µM (+++) and GI$_{50}$<100 nM (++++). These cancer cell lines and primary cultures correspond to acute lymphocytic leukemia (ALL), CEMO-1, to activated B-cell-like diffuse large B-cell lymphoma (ABC-DLBCL), OCI-Ly3 and OCI-Ly10 and to hepatocellular carcinoma cells (HCC), HepG2, Hep3B and PLC/PRF/5.

TABLE 3

| Example | CEMO-1 | OCI-Ly3 | OCI-Ly10 | HEPG2 | HEP3B | PLC/PRF/5 |
| --- | --- | --- | --- | --- | --- | --- |
| 1-02 | +++ | +++ | ++ | ++ | ++ | +++ |
| 1-03 | ++ |  |  | ++ | ++ | +++ |
| 1-04 | +++ |  |  | ++ | ++ | +++ |
| 2-03 | ++ |  |  |  |  |  |
| 2-06 | ++ |  |  | + | + | ++ |
| 2-07 | ++ |  |  | ++ | ++ | ++ |
| 2-08 | ++ |  |  | ++ | ++ | ++ |
| 2-12 | +++ |  |  | +++ | +++ |  |

Compounds in Table 3 inhibit proliferation of acute lymphocytic leukemia (ALL), activated B-cell-like diffuse large B-cell lymphoma (ABC-DLBCL) and hepatocarcinoma (HCC) cell lines.

REFERENCES CITED IN THE APPLICATION

Vilas-Zornoza A. et al., "Frequent and Simultaneous Epigenetic Inactivation of TP53 Pathway Genes in Acute Lymphoblastic Leukemia", PLoS ONE 2011. 6(2): p. e17012.

Neary, R. et al, "Epigenetics and the overhealing wound: the role of DNA methylation in fibrosis", Fibrogenesis & Tissue Repair, 2015, 8:18.

Lee S. et al., "DNA methyltransferase inhibition accelerates the immunomodulation and migration of human mesenchymal stem cells" Scientific Reports 2015, 5:8020.

Shankar S R. et al., "G9a, a multipotent regulator of gene expression", Epigenetics, 2013. 8(1): p. 16-22.

Esteve P O. et al., "Direct interaction between DNMT1 and G9a coordinates DNA and histone methylation during replication", Genes Dev 2006, 20:3089-3103.

Tachibana M. et al., "G9a/GLP complexes independently mediate H3K9 and DNA methylation to silence transcription", The EMBO Journal 2008, 27:2681-2690.

Wozniak R J. et al., "5-Aza-2'-deoxycytidine-mediated reductions in G9A histone methyltransferase and histone H3 K9 di-methylation levels are linked to tumor suppressor gene reactivation", Oncogene 2007, 26, 77-90.

Sharma S. et al., "Lysine methyltransferase G9a is not required for DNMT3A/3B anchoring to methylated nucleosomes and maintenance of DNA methylation in somatic cells", Epigenetics Chromatin 2012, 5, 3.

Chambers R D., et al., "Reactions involving fluoride ion. Part 42. Heterocyclic compounds from perfluoro-3,4-dimethylhexa-2,4-diene", Journal of the Chemical Society, Perkin Transactions 1: Organic and Bio-Organic Chemistry (1997), (10), 1457-1463.

US20080306049

CN1830978

Green and P. G. M. Wuts, Protective Groups in Organic Chemistry, Wiley, 3rd ed. 1999, Chapter 2, pp. 17-200 and Chapter 5, pp. 369-451.

The invention claimed is:

1. A compound of formula (I), or a pharmaceutically or veterinary acceptable salt thereof, or any stereoisomer or mixtures thereof, either of the compound of formula (I) or of any of its pharmaceutically or veterinary acceptable salts

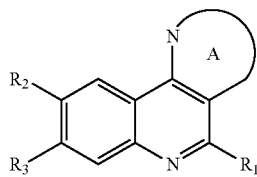

(I)

which is selected from the group consisting of compounds of formula (Ib), (Ia), (Ic), and (Id):

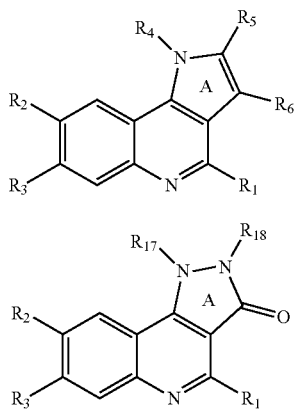

wherein
$R_1$ is $Cy^1$ and is attached to the quinoline through a carbon atom;
$Cy^1$ is a known ring system selected from the group consisting of:
  (i) phenyl;
  (ii) 5- or 6-membered heteroaromatic ring;
  (iii) 3- to 7-membered carbocyclic or heterocyclic monocyclic ring, which is saturated or partially unsaturated;
  (iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
  (v) phenyl fused to a 6- to 14-membered saturated or partially unsaturated carbocyclic or heterocyclic bicyclic ring, wherein the rings of the bicyclic ring are spiro-fused; and
  (vi) 5- to 6-membered heteroaromatic ring fused to a 6- to 14-membered saturated or partially unsaturated carbocyclic or heterocyclic bicyclic ring, wherein the rings of the bicyclic ring are spiro-fused;
wherein $Cy^1$ is optionally substituted with:
  a) one $Cy^2$ or one $Cy^3$, and/or
  b) one or more substituents $R^c$, and/or
  c) one or more substituents $Z^1$ optionally substituted with one or more substituents $R^c$ and/or one $Cy^2$;
    wherein $Cy^2$ or $Cy^3$ are optionally substituted with one or more substituents independently selected from $R^c$, and $Z^2$ optionally substituted with one or more substituents $R^c$;
$R_2$ is selected from the group consisting of H, $R^g$, halogen, $-NO_2$, $-CN$, $-OR^{g'}$, $-OC(O)R^{g'}$, $-OC(O)OR^{g'}$, $-OC(O)NR^{g'}R^{g'}$, $-NR^{g'}R^{g'}$, $-NR^{g'}C(O)R^{g'}$, $-NR^{g'}C(O)OR^{g'}$, $-NR^{g'}C(O)NR^{g'}R^{g'}$, $-NR^{g'}S(O)_2R^{g'}$, $-NR^{g'}SO_2NR^{g'}R^{g'}$, $-SR^{g'}$, $-S(O)R^{g'}$, $-S(O)OR^{g'}$, $-SO_2R^{g'}$, $-SO_2(OR^{g'})$, $-SO_2NR^{g'}R^{g'}$, $-SC(O)NR^{g'}R^{g'}$, $-C(O)R^{g'}$, $-C(O)OR^{g'}$, $-C(O)NR^{g'}R^{g'}$, and $-C(O)NR^{g'}OR^{g'}$, and $-C(O)NR^{g'}SO_2R^{g'}$;
$R_3$ is $-OR^d$;
$R_4$, $R_{17}$, $R_{18}$ are independently H or $R^d$;
$R_5$ is selected from the group consisting of H, $R^e$, $OR^f$, $-NR^{f'}R^{g'}$, $NR^{a'}COR^f$, and $R^f$;
$R_6$ is selected from the group consisting of H, $R^a$, and one or more halogen atoms;
each $R^a$ is independently selected from the group consisting of $(C_1\text{-}C_6)$alkyl, $(C_2\text{-}C_6)$alkenyl, $(C_2\text{-}C_6)$alkynyl, $(C_2\text{-}C_6)$hydrocarbon chain having one or more double bonds and one or more triple bonds, wherein each $R^a$ is optionally substituted with one or more halogen atoms,
each $R^{a'}$ is independently H or $R^a$;
each $R^c$ is independently selected from halogen, $-NO_2$, $-CN$, $-OR^{g'}$, $-OC(Y)R^{g'}$, $-OC(Y)OR^{g'}$, $-OC(Y)NR^{g'}R^{g'}$, $-NR^{g'}R^{g'}$, $-NR^{g'}C(Y)R^{g'}$, $-NR^{g'}C(Y)OR^{g'}$, $-NR^{g'}C(Y)NR^{g'}R^{g'}$, $-NR^{g'}S(O)_2R^{g'}$, $-NR^{g'}SO_2NR^{g'}R^{g'}$, $-SR^{g'}$, $-S(O)R^{g'}$, $-S(O)OR^{g'}$, $-SO_2R^{g'}$, $-SO_2(OR^{g'})$, $-SO_2NR^{g'}R^{g'}$, $-SC(Y)NR^{g'}R^{g'}$, $-C(Y)R^{g'}$, $-C(Y)OR^{g'}$, $-C(Y)NR^{g'}R^{g'}$, $-C(Y)NR^{g'}OR^{g'}$, and $-C(O)NR^{g'}SO_2R^{g'}$;
each $R^d$ is independently $R^e$ or $R^f$;
each $R^e$ is independently $Cy^5$ optionally substituted with:
  a) one $Cy^7$; and/or
  b) one or more substituents $R^c$, and/or
  c) one or more substituents $Z^4$ optionally substituted with one or more substituents $R^c$ and/or one $Cy^7$;
    wherein $Cy^7$ is optionally substituted with one or more substituents independently selected from $R^c$, and $Z^5$ optionally substituted with one or more substituents $R^c$; and
each $R^f$ is independently $Z^3$ optionally substituted with one or more substituents $R^c$ and/or one $Cy^6$; wherein $Cy^6$ is optionally substituted with:
  a) one $Cy^8$; and/or
  b) one or more substituents $R^c$, and/or
  c) one or more substituents $Z^6$ optionally substituted with one or more substituents $R^c$ and/or one $Cy^8$;
wherein $Cy^8$ is optionally substituted with one or more substituents independently selected from $R^c$, and $Z^7$ optionally substituted with one or more substituents $R^c$;
each $R^{f'}$ is independently H or $R^f$;
each $R^g$ is independently selected from the group consisting of $(C_1\text{-}C_6)$alkyl, $(C_2\text{-}C_6)$alkenyl, $(C_2\text{-}C_6)$alkynyl, $(C_2\text{-}C_6)$hydrocarbon chain having one or more double bonds and one or more triple bonds, and 3- to 7-membered saturated or partially unsaturated or aromatic carbocyclic or heterocyclic monocyclic ring, wherein each $R^g$ is optionally substituted with one or more halogen atoms,
each $R^{g'}$ is independently H or $R^g$;
Y is O, S, or $NR^{g'}$;
$Z^1\text{-}Z^7$ are independently selected from the group consisting of $(C_1\text{-}C_{12})$alkyl, $(C_2\text{-}C_{12})$alkenyl, $(C_2\text{-}C_{12})$alkynyl, and $(C_2\text{-}C_6)$hydrocarbon chain having one or more double bonds and one or more triple bonds;
$Cy^2$, $Cy^7$ and $Cy^8$ are independently a known ring system selected from the group consisting of phenyl; 3- to 7-membered carbocyclic or heterocyclic monocyclic ring, saturated or partially unsaturated; and 5- or 6-membered heteroaromatic ring;

77

Cy³, Cy⁵ and Cy⁶ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N($C_1$-$C_4$)alkyl].

2. The compound of formula (I) according to claim 1, which is a compound of formula (Ia).

3. The compound of formula (I) according to claim 1, wherein $Cy^1$ is a known ring system attached to the quinoline through a carbon atom selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
wherein $Cy^1$ is optionally substituted as defined in claim 1.

4. The compound of formula (I) according to claim 3, wherein $Cy^1$ is a 5- to 6-membered heteroaromatic monocyclic ring attached to the quinoline through a carbon atom.

5. The compound of formula (I) according to claim 1, wherein $R_2$ is selected from H, halogen, —CN and —$OR^{g'}$.

6. The compound of formula (I) according to claim 5, wherein $R_2$ is H or —$OR^g$.

7. The compound of formula (I) according to claim 1, wherein $R^d$ in $R^3$ is a moiety which contains at least one N atom.

8. The compound of formula (I) according to claim 7, wherein $R^d$ is $Z^3$, wherein $Z^3$ is ($C_1$-$C_6$)alkyl substituted with one or more substituents as defined in claim 1.

9. The compound of formula (I) according to claim 1, wherein $R_3$ is a moiety of formula (XL):

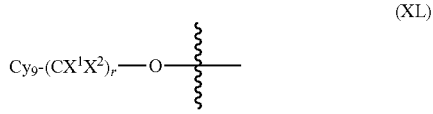

(XL)

wherein
$Cy_9$ is a 3- to 7-membered saturated or partially unsaturated or aromatic carbocyclic or heterocyclic monocyclic ring or a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring, and Cy9 is optionally substituted with one or more substituents selected from halogen and ($C_1$-$C_3$)alkyl optionally substituted with one or more halogen atoms,
$X^1$ and $X^2$ are independently H or halogen, and
r is a value selected from 0 to 6.

10. The compound of formula (I) according to claim 1, wherein $R_4$-$R_6$, $R_{17}$ and $R_{18}$ are H.

78

11. The compound of formula (I) according to claim 1, wherein $R_6$ is H;
one of $R_4$-$R_5$, and one of $R_{17}$ and $R_{18}$ are independently a ($C_1$-$C_{12}$)alkyl substituted with $Cy^6$ optionally substituted with one o more substituents selected from the group consisting of:
halogen,
—C(O) $R^{g'}$,
—($C_1$-$C_6$)alkyl optionally substituted with one or more halogen atoms; and
a 3- to 7-membered saturated carbocyclic monocyclic ring;
wherein $Cy^6$ is a 3- to 7-membered carbocyclic or heterocyclic saturated or partially unsaturated monocyclic ring; or a 3- to 7-membered saturated carbocyclic or heterocyclic monocyclic ring, which is spiro-fused to a 3- to 7-membered saturated carbocyclic or heterocyclic monocyclic ring, and
$R^{g'}$ is H or ($C_1$-$C_6$)alkyl optionally substituted with one or more halogen atoms; and
the other ones of $R_4$-$R_5$, and $R_{17}$ and $R_{18}$ are H.

12. A pharmaceutical or veterinary composition which comprises a therapeutically effective amount of a compound of formula (I) as defined in claim 1, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

13. A method for the treatment of fibrosis, comprising administering an effective amount of a compound of formula (I) as defined in claim 1, and one or more pharmaceutically or veterinary acceptable excipients or carriers, in a subject in need thereof, including a human.

14. A method for the treatment of cancer, comprising administering an effective amount of a compound of formula (I) as defined in claim 1, and one or more pharmaceutically or veterinary acceptable excipients or carriers, in a subject in need thereof, including a human; wherein the cancer is selected from the group consisting of Acute Lymphocytic Leukemia (ALL), Diffuse Large B-cell lymphoma (DLBCL), bladder cancer, breast cancer, cervical cancer, colorectal cancer, glioblastoma, hepatocarcinoma, melanoma, pancreatic cancer, prostate cancer, renal cancer, small-cell lung cancer, non small-cell lung cancer, acute myeloid leukemia, mantle cell lymphoma and multiple myeloma.

15. The compound of formula (I) according to claim 1, wherein $Cy^1$ is a known ring system attached to the quinoline through a carbon atom selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;
wherein $Cy^1$ is optionally substituted as defined in claim 1; $R_2$ is selected from H, halogen, —CN and —$OR^{g'}$; and $R^d$ in $R^3$ is a moiety which contains at least one N atom.

16. The compound of formula (I) according to claim 1, wherein $Cy^1$ is a known ring system attached to the quinoline through a carbon atom selected from the group consisting of:
(i) phenyl;
(ii) 5- or 6-membered heteroaromatic ring;
(iii) 3- to 7-membered carbocyclic or heterocyclic monocyclic ring, which is saturated or partially unsaturated;

wherein $Cy^1$ is optionally substituted as defined in claim 1; $R_2$ is selected from H, halogen, —CN and —OR$^{g'}$; and $R_3$ is a moiety of formula (XL):

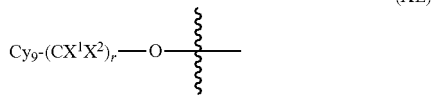

(XL)

wherein $Cy_9$ is a 3- to 7-membered saturated or partially unsaturated or aromatic carbocyclic or heterocyclic monocyclic ring or a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring, and $Cy_9$ is optionally substituted with one or more substituents selected from halogen and $(C_1\text{-}C_3)$alkyl optionally substituted with one or more halogen atoms, $X^1$ and $X^2$ are independently H or halogen, and r is a value selected from 0 to 6.

17. The compound of formula (I) according to claim 1, which is a compound of formula (Ia), wherein $Cy^1$ is a known ring system attached to the quinoline through a carbon atom selected from the group consisting of:
   (i) phenyl;
   (ii) 5- or 6-membered heteroaromatic ring;
   (iii) 3- to 7-membered carbocyclic or heterocyclic monocyclic ring, which is saturated or partially unsaturated;
   wherein $Cy^1$ is optionally substituted as defined in claim 1; $R_2$ is selected from H, halogen, —CN and —OR$^{g'}$; and $R^d$ in $R^3$ is a moiety which contains at least one N atom.

18. The compound of formula (I) according to claim 1, wherein $R_5$ is selected from the group consisting of H, $R_e$, and $R_f$.

* * * * *